United States Patent
Li et al.

(10) Patent No.: US 10,316,064 B2
(45) Date of Patent: Jun. 11, 2019

(54) TEICOPLANIN ANALOGS AND USES THEREOF

(71) Applicant: Academia Sinica, Taipei (TW)

(72) Inventors: Tsung-Lin Li, Taipei (TW); Syue-Yi Lyu, Taipei (TW); Yu-CHen Liu, Taipei (TW); Chin-Yuan Chang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/115,179

(22) PCT Filed: Jan. 26, 2015

(86) PCT No.: PCT/US2015/012914
§ 371 (c)(1),
(2) Date: Jul. 28, 2016

(87) PCT Pub. No.: WO2015/116537
PCT Pub. Date: Aug. 6, 2015

(65) Prior Publication Data
US 2016/0347795 A1    Dec. 1, 2016
US 2017/0327542 A9    Nov. 16, 2017

Related U.S. Application Data

(60) Provisional application No. 61/932,325, filed on Jan. 28, 2014.

(51) Int. Cl.
*C07K 9/00* (2006.01)
*C12P 19/60* (2006.01)
*A61K 38/00* (2006.01)

(52) U.S. Cl.
CPC .............. *C07K 9/008* (2013.01); *C12P 19/60* (2013.01); *A61K 38/00* (2013.01); *Y02A 50/473* (2018.01); *Y02A 50/481* (2018.01)

(58) Field of Classification Search
None
See application file for complete search history.

(56) References Cited

U.S. PATENT DOCUMENTS

| | | | | |
|---|---|---|---|---|
| 5,085,990 | A * | 2/1992 | Lancini | C07K 9/008 435/252.6 |
| 2007/0287663 | A1 | 12/2007 | Mathiesen et al. | |
| 2012/0108498 | A1* | 5/2012 | Li | C07K 9/008 514/2.6 |
| 2013/0288955 | A1 | 10/2013 | Li et al. | |

FOREIGN PATENT DOCUMENTS

EP    0 306 645 B1    3/1989

OTHER PUBLICATIONS

Liu, Yu-Chen et al, "Interception of teicoplanin oxidation intermediates yields new antimicrobial scaffolds." Nat. Chem. Biol. (2011) 7 p. 304-400.*

Zanol, M. et al, "Isolation and structure determination of minor components of teicoplanin." Chromatographia (1988) 26 p. 234-236.*

Kruger et al., Tailoring of glycopeptide scaffolds by the acyltransferases from the teicoplanin and A-40,926 biosynthetic operons. Chem Biol. Jan. 2005;12(1):131-40.

Lyu et al., Multiple complexes of long aliphatic N-acyltransferases lead to synthesis of 2,6-diacylated/2-acyl-substituted glycopeptide antibiotics, effectively killing vancomycin-resistant enterococcus. J Am Chem Soc. Aug. 6, 2014;136(31):10989-95. doi: 10.1021/ja504125v. Epub Jul. 25, 2014.

Howard-Jones et al., Kinetic analysis of teicoplanin glycosyltransferases and acyltransferase reveal ordered tailoring of aglycone scaffold to reconstitute mature teicoplanin. J Am Chem Soc. Aug. 22, 2007;129(33):10082-3. Epub Jul. 28, 2007.

Li et al., Biosynthetic gene cluster of the glycopeptide antibiotic teicoplanin: characterization of two glycosyltransferases and the key acyltransferase. Chem Biol. Jan. 2004;11(1):107-19.

Li et al., Combining biocatalysis and chemoselective chemistries for glycopeptide antibiotics modification. Curr Opin Chem Biol. Apr. 2012;16(1-2):170-8. doi: 10.1016/j.cbpa.2012.01.017. Epub Feb. 13, 2012.

* cited by examiner

*Primary Examiner* — Fred H Reynolds
(74) *Attorney, Agent, or Firm* — Wolf, Greenfield & Sacks, P.C.

(57) ABSTRACT

Described herein are compounds of Formula (I), or pharmaceutically acceptable salts thereof, and pharmaceutical compositions thereof. Compounds of the present invention are useful for inhibiting bacterial growth. Methods of using the compounds for treating and/or preventing bacterial infection as well as methods of preparing the compounds are also described

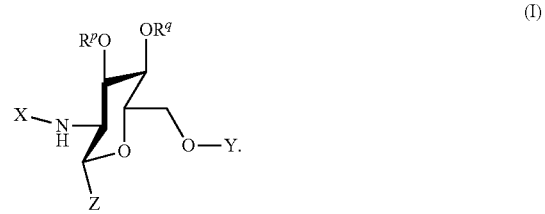

(I)

21 Claims, 61 Drawing Sheets

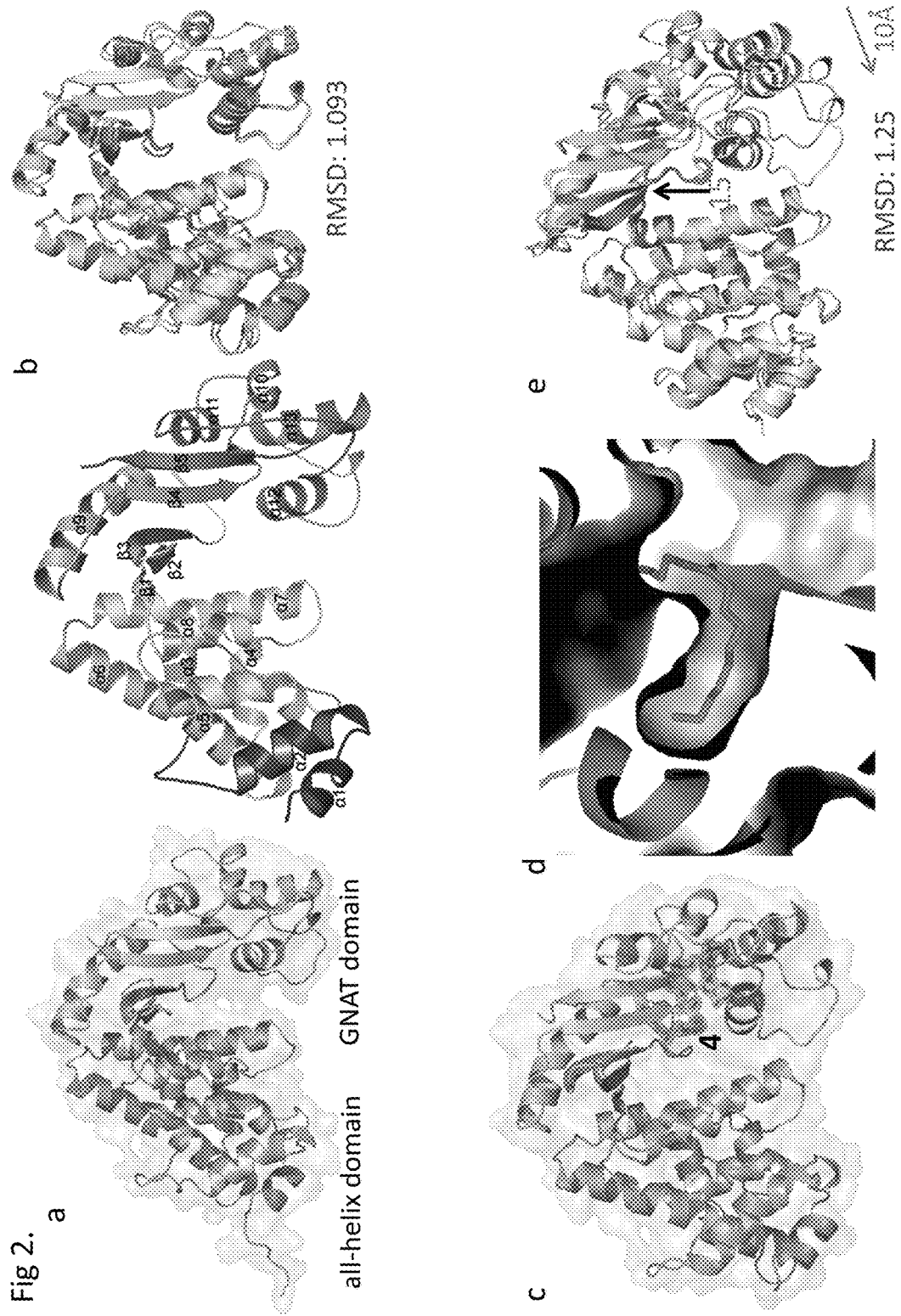

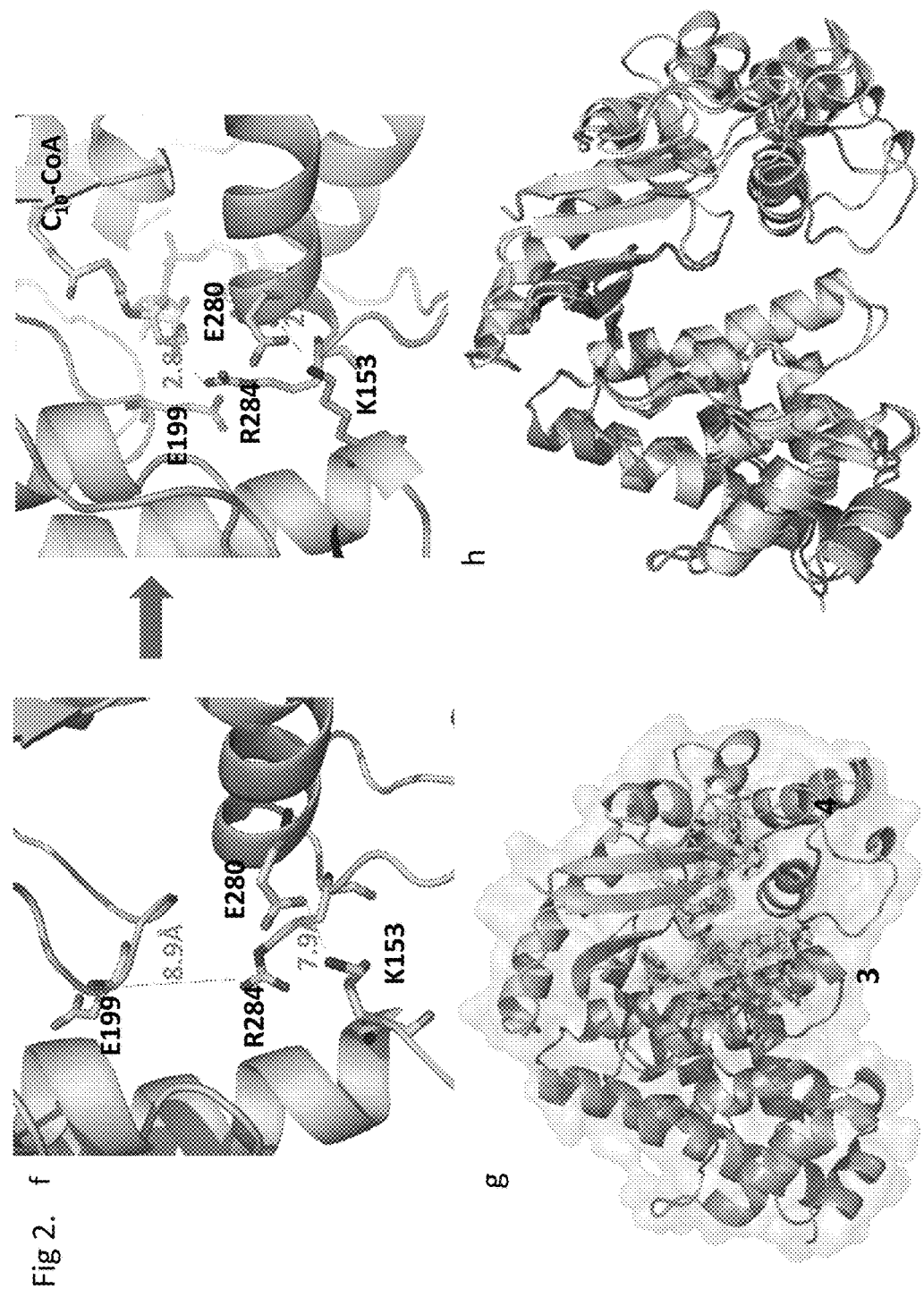

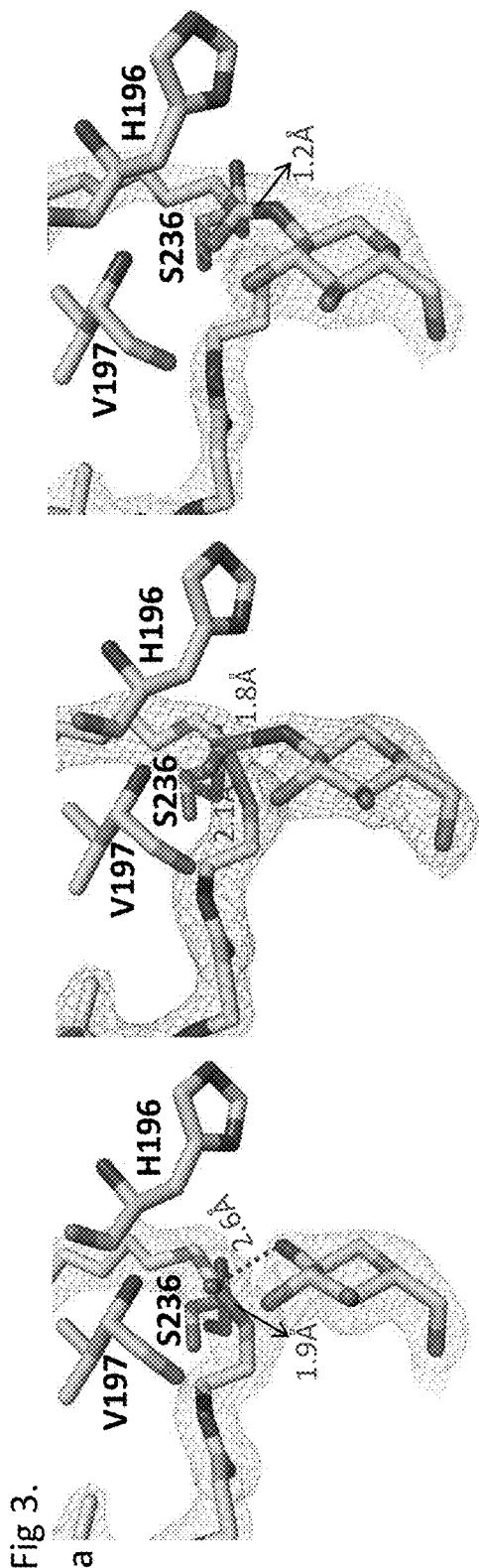
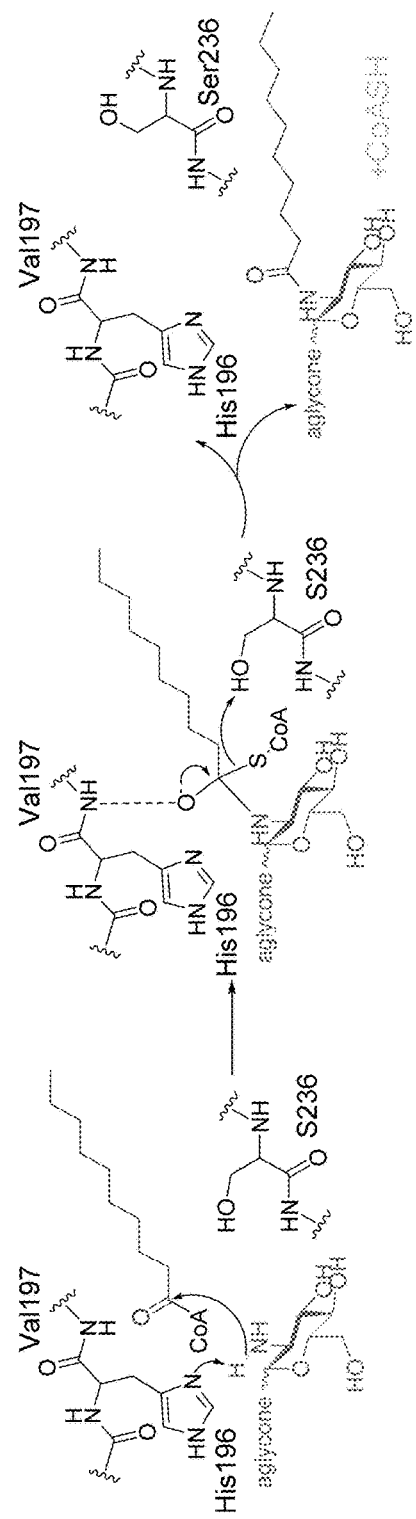
Fig 3.
a

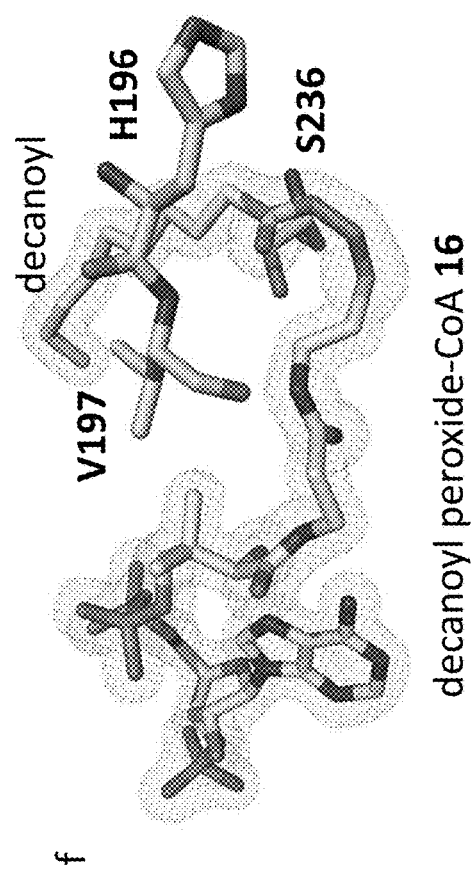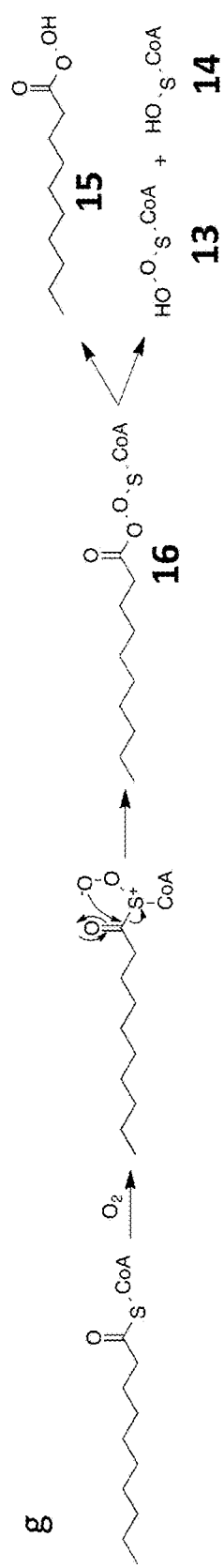
Figure 5 (continued)

Figure 7

Orf11*

| No. | Chain | Z | rmsd | lali | nres | %id | PDB | Description |
|---|---|---|---|---|---|---|---|---|
| 1: | 2ookA | 5.0 | 3.7 | 93 | 163 | 11 | PDB | MOLECULE: PROBABLE ACETYLTRANSFERASE; |
| 2: | 2x7bA | 4.9 | 3.7 | 95 | 152 | 5 | PDB | MOLECULE: HUMAN MAK3 HOMOLOG; |
| 3: | 1s8kA | 4.7 | 3.9 | 95 | 164 | 11 | PDB | MOLECULE: PROBABLE ACETYLTRANSFERASE; |
| 4: | 1s8kB | 4.7 | 4.0 | 95 | 164 | 11 | PDB | MOLECULE: PROBABLE ACETYLTRANSFERASE; |
| 5: | 1rxnC | 4.7 | 4.0 | 91 | 170 | 10 | PDB | MOLECULE: SIMILAR TO PHOSPHINOTHRICIN ACETYLTRANSFERASE; |
| 6: | 2jlmA | 4.7 | 0.8 | 86 | 145 | 14 | PDB | MOLECULE: GLYPHOSATE N-ACETYLTRANSFERASE; |
| 7: | 1s8kA | 4.7 | 4.1 | 92 | 164 | 10 | PDB | MOLECULE: PROBABLE ACETYLTRANSFERASE; |
| 8: | 2bsmA | 4.6 | 3.1 | 86 | 145 | 15 | PDB | MOLECULE: GLYPHOSATE N-ACETYLTRANSFERASE; |
| 9: | 2j7tA | 4.6 | 4.0 | 94 | 171 | 9 | PDB | MOLECULE: ACETYLTRANSFERASE, GNAT FAMILY; |
| 10: | 2ff7A | 4.6 | 4.1 | 94 | 168 | 5 | PDB | MOLECULE: ACETYLTRANSFERASE, GNAT FAMILY; |
| 11: | 2bsmA | 4.6 | 2.8 | 86 | 145 | 14 | PDB | MOLECULE: GLYPHOSATE N-ACETYLTRANSFERASE; |
| 12: | 2bssA | 4.6 | 3.7 | 95 | 155 | 6 | PDB | MOLECULE: N-ACETYLTRANSFERASE 13; |
| 13: | 2gn4A | 4.6 | 4.1 | 96 | 162 | 4 | PDB | MOLECULE: LACTOCOCCAL BROPHAGE P35 PROTEIN U5; |
| 14: | 2i4eA | 4.5 | 3.8 | 92 | 165 | 10 | PDB | MOLECULE: SIMILAR TO PHOSPHINOTHRICIN ACETYLTRANSFERASE; |
| 15: | 1i12A | 4.5 | 4.1 | 94 | 171 | 9 | PDB | MOLECULE: ACETYLTRANSFERASE, GNAT FAMILY; |

N-terminal all helix domain

| No. | Chain | Z | rmsd | lali | nres | %id | PDB | Description |
|---|---|---|---|---|---|---|---|---|
| 1: | 3ondA | 3.6 | 3.2 | 80 | 159 | 6 | PDB | MOLECULE: PUTATIVE ATPASE, AAA FAMILY; |
| 2: | 3s4lC | 3.6 | 4.5 | 94 | 319 | 3 | PDB | MOLECULE: DNA POLYMERASE ACCESSORY PROTEIN 44; |
| 3: | 1xhlI | 3.5 | 3.9 | 90 | 317 | 4 | PDB | MOLECULE: ACTIVATOR 1 95 KDA SUBUNIT; |
| 4: | 3pv5A | 3.5 | 3.4 | 85 | 426 | 6 | PDB | MOLECULE: REPLICATION-ASSOCIATED RECOMBINATION PROTEIN A; |
| 5: | 3ondA | 3.5 | 3.1 | 79 | 158 | 6 | PDB | MOLECULE: PUTATIVE ATPASE, AAA FAMILY; |
| 6: | 3m4wA | 3.5 | 3.1 | 61 | 163 | 5 | PDB | MOLECULE: PREDICTED ATPASE; |
| 7: | 3s4lD | 3.5 | 3.2 | 83 | 319 | 2 | PDB | MOLECULE: DNA POLYMERASE ACCESSORY PROTEIN 44; |
| 8: | 1sxjC | 3.5 | 5.1 | 94 | 326 | 4 | PDB | MOLECULE: ACTIVATOR 1 95 KDA SUBUNIT; |
| 9: | 3m5lB | 3.5 | 3.6 | 90 | 294 | 4 | PDB | MOLECULE: DNA POLYMERASE ACCESSORY PROTEIN 44; |
| 10: | 3u6lB | 3.5 | 3.3 | 84 | 320 | 2 | PDB | MOLECULE: DNA POLYMERASE ACCESSORY PROTEIN 44; |
| 11: | 3u6lA | 3.5 | 4.9 | 92 | 320 | 3 | PDB | MOLECULE: DNA POLYMERASE ACCESSORY PROTEIN 44; |
| 12: | 3a8lC | 3.4 | 3.4 | 78 | 319 | 4 | PDB | MOLECULE: DNA POLYMERASE ACCESSORY PROTEIN 44; |
| 13: | 3m4wA | 3.4 | 9.1 | 64 | 305 | 4 | PDB | MOLECULE: DNA POLYMERASE ACCESSORY PROTEIN 44; |
| 14: | 3m4wA | 3.3 | 3.3 | 80 | 163 | 5 | PDB | MOLECULE: PREDICTED ATPASE; |
| 15: | 3pv5B | 3.3 | 4.0 | 85 | 417 | 5 | PDB | MOLECULE: REPLICATION-ASSOCIATED RECOMBINATION PROTEIN A; |

¹³C NMR spectrum for compound 7

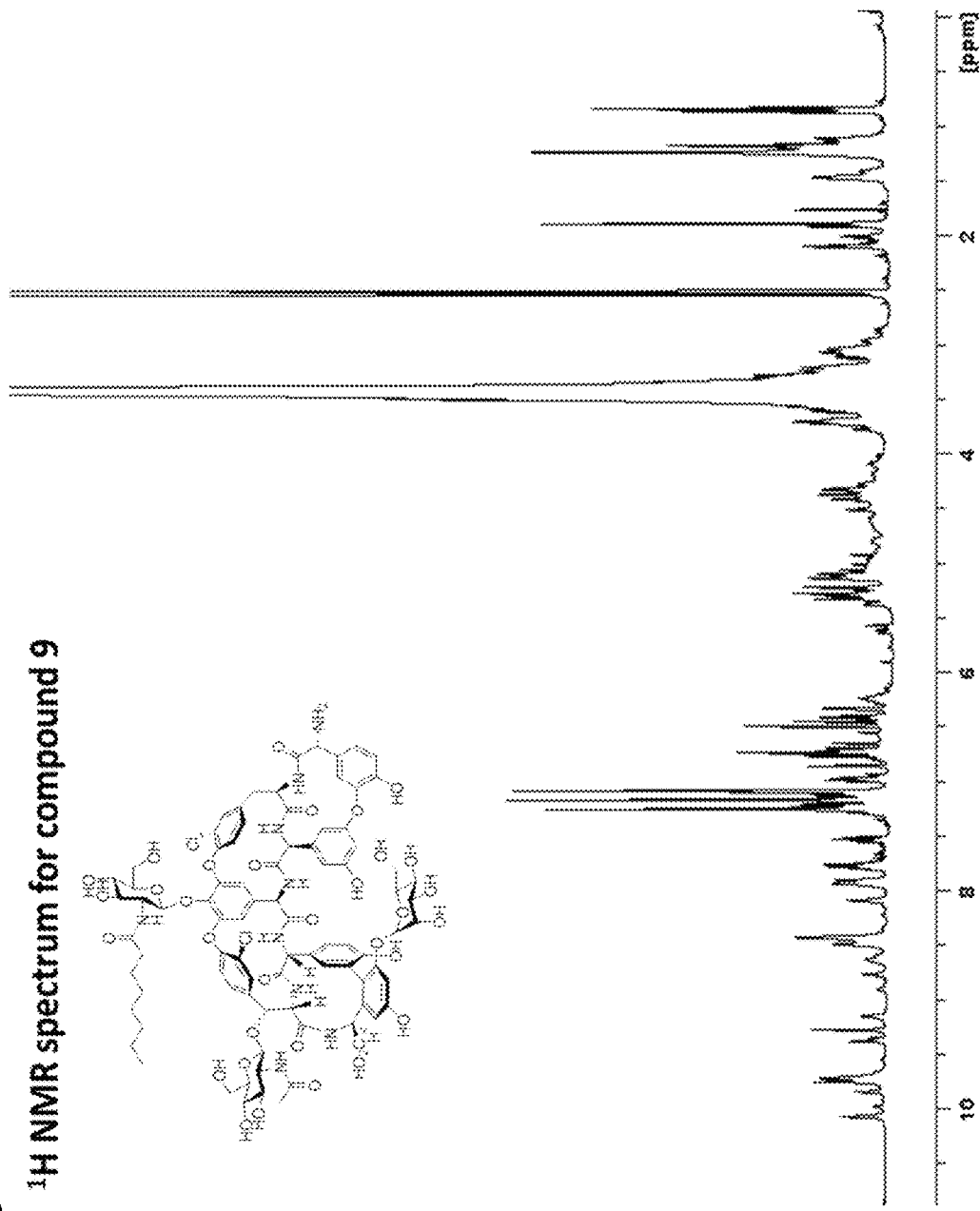
Figure 16. ¹H NMR spectrum for compound 9

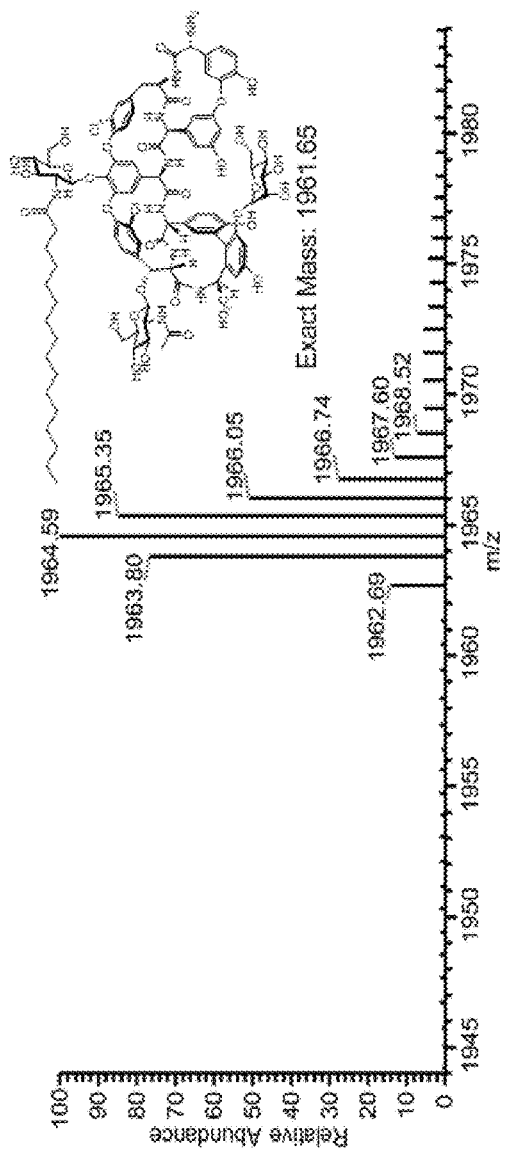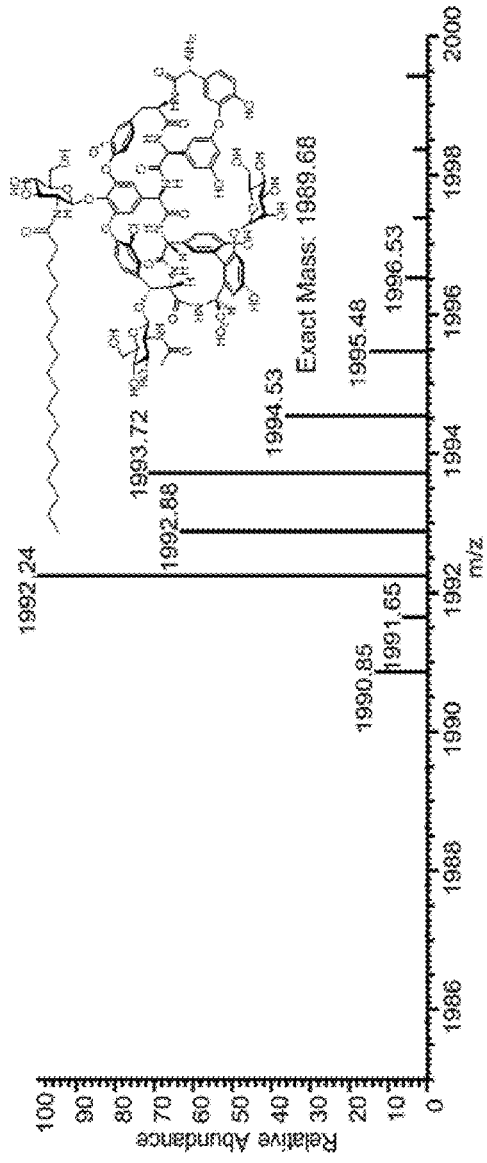
Figure 18 (continued)

Figure 19

Table 1

| | Se-Orf11* | Orf11*H196A/ decanoyl-CoA | Dbv8/ decanoyl-CoA | Orf11*H196A/ decanoyl-CoA/ Tei pseudoaglycone | Orf11*H196A/ decanoyl-CoA/ Tei pseudoaglycone |
|---|---|---|---|---|---|
| Data collection | | | | | |
| Space group | $P6_2$ | $P6_5$ | $P2_12_12_1$ | $P6_5$ | $P6_5$ |
| Cell dimensions | | | | | |
| $a, b, c$ (Å) | 105.5, 105.5, 133.9 | 133.4, 133.4, 49.5 | 53.7, 68.5, 95.1 | 133.6, 133.6, 49.3 | 133.7, 133.7, 49.4 |
| $\alpha, \beta, \gamma$ (°) | 90.0, 90.0, 120.0 | 90.0, 90.0, 120.0 | 90.0, 90.0, 90.0 | 90.0, 90.0, 120.0 | 90.0, 90.0, 120.0 |
| Wavelength | 0.97893 | 0.97622 | 0.97622 | 1.00000 | 1.00000 |
| Resolution (Å) | 30.0-2.90(3.00-2.90) | 30.0-1.90(1.97-1.90) | 30.0-2.10(2.18-2.10) | 30.0-1.90(1.97-1.90) | 30.0-2.15(2.23-2.15) |
| $R_{sym}$ or $R_{merge}$ | 8.6(69.0) | 9.3(54.8) | 14.2(57.2) | 5.1(56.8) | 7.8(58.2) |
| $I/\sigma I$ | 33.3(5.1) | 16.3(3.5) | 13.5(2.3) | 38.7(3.9) | 25.5(5.3) |
| Completeness (%) | 98.8(99.6) | 100.0(100.0) | 99.6(97.2) | 100.0(100.0) | 99.9(100.0) |
| Redundancy | 12.6(12.4) | 5.9(6.0) | 7.4(5.6) | 5.9(6.0) | 7.0(7.4) |
| Refinement | | | | | |
| Resolution (Å) | 2.9 | 1.90 | 2.10 | 1.90 | 2.15 |
| No. reflections | 17598 | 37919 | 19900 | 37841 | 26394 |
| $R_{work}/R_{free}$ | 18.0/22.9 | 16.4/20.2 | 18.9/25.7 | 17.4/21.1 | 17.7/21.7 |
| No. atoms | | | | | |
| Protein | 2643 | 2671 | 2586 | 2670 | 2699 |
| Ligand/ion | -/- | 59/0 | 59/0 | 180/10 | 180/0 |
| Water | 53 | 464 | 272 | 363 | 255 |
| B-factors | | | | | |
| Protein | 67.0 | 27.6 | 24.9 | 31.8 | 38.2 |
| Ligand/ion | -/- | 25.3/0 | 25.1/0 | 63.7/0 | 71.8/0 |
| Water | 50.9 | 40.5 | 31.9 | 42.8 | 47.4 |
| R.m.s deviations | | | | | |
| Bond lengths (Å) | 0.0087 | 0.0119 | 0.0118 | 0.0101 | 0.0122 |
| Bond angles (°) | 1.4367 | 1.3934 | 1.5415 | 1.302 | 1.555 |

Figure 19 (continued)

Table 1 (continued)

| | Orf11*H196A/ CoA/ 10C-teicoplanin | Orf11*H196A/ sulfenyl-CoA/ decanoic acid | Orf11*H196A/ sulfuperoxide-CoA/ decanoic acid | Orf11*/ CoA-disulfide/ decanoic acid | Orf11*H196A/ sulfuperoxide-CoA/ decanoylperoxide |
|---|---|---|---|---|---|
| Data collection | | | | | |
| Space group | P6$_5$ | P6$_5$ | P6$_5$ | P6$_5$ | P6$_5$ |
| Cell dimensions | | | | | |
| $a, b, c$ (Å) | 133.6, 133.6, 49.3 | 133.5, 133.5, 49.3 | 133.5, 133.5, 49.1 | 133.4, 133.4, 49.3 | 133.5, 133.5, 48.9 |
| $\alpha, \beta, \gamma$ (°) | 90.0, 90.0, 120.0 | 90.0, 90.0, 120.0 | 90.0, 90.0, 120.0 | 90.0, 90.0, 120.0 | 90.0, 90.0, 120.0 |
| Wavelength | 1.00000 | 1.00000 | 1.00000 | 0.90000 | 0.90000 |
| Resolution (Å) | 30.0-2.00(2.07-2.00) | 30.0-2.25(2.33-2.25) | 30.0-1.85(1.92-1.85) | 30.0-1.86(1.93-1.86) | 30.0-2.00(2.07-2.00) |
| $R_{sym}$ or $R_{merge}$ | 5.8(59.5) | 11.9(64.2) | 5.6(53.7) | 8.1(54.5) | 7.4(52.9) |
| $I/\sigma I$ | 34.4(3.6) | 17.6(3.2) | 31.6(3.4) | 23.7(3.8) | 23.1(4.0) |
| Completeness (%) | 100.0(100.0) | 100.0(100.0) | 99.9(99.9) | 100.0(100.0) | 100.0(100.0) |
| Redundancy | 7.5(7.5) | 7.4(7.2) | 7.0(5.7) | 7.3(7.0) | 7.4(7.4) |
| Refinement | | | | | |
| Resolution (Å) | 2.00 | 2.25 | 1.85 | 1.86 | 2.00 |
| No. reflections | 32571 | 22882 | 40812 | 40268 | 32161 |
| $R_{work}/R_{free}$ | 17.3/21.7 | 18.0/23.1 | 17.6/20.6 | 16.9/20.0 | 19.1/23.1 |
| No. atoms | | | | | |
| Protein | 2658 | 2659 | 2664 | 2675 | 2635 |
| Ligand/ion | 180/0 | 61/0 | 62/0 | 108/10 | 63/0 |
| Water | 311 | 292 | 404 | 404 | 286 |
| B-factors | | | | | |
| Protein | 35.3 | 29.3 | 28.2 | 25.3 | 36.0 |
| Ligand/ion | 45.5/0 | 28.2/0 | 26.9/0 | 41.4/0 | 42.4/0 |
| Water | 43.9 | 37.9 | 39.3 | 36.3 | 43.7 |
| R.m.s deviations | | | | | |
| Bond lengths (Å) | 0.0105 | 0.0088 | 0.0116 | 0.0109 | 0.0115 |
| Bond angles (°) | 1.456 | 1.250 | 1.4294 | 1.4332 | 1.4011 |

Figure 19 (continued)

Table 1 (continued)

| | Orf11*H196A/ decanoyl peroxide-CoA | Orf11*/ octyl peroxide-CoA | Orf11*/ octyl peroxide-CoA/ glucose |
|---|---|---|---|
| Data collection | | | |
| Space group | $P6_5$ | $P6_5$ | $P6_5$ |
| Cell dimensions | | | |
| $a, b, c$ (Å) | 132.9, 132.9, 49.3 | 132.5, 132.5, 48.8 | 132.6, 132.6, 48.7 |
| $\alpha, \beta, \gamma$ (°) | 90.0, 90.0, 120.0 | 90.0, 90.0, 120.0 | 90.0, 90.0, 120.0 |
| Wavelength | 0.90000 | 1.00000 | 1.54178 |
| Resolution (Å) | 30.0-1.65(1.71-1.65) | 30.0-1.90(1.97-1.90) | 30.0-1.70(1.76-1.70) |
| $R_{sym}$ or $R_{merge}$ | 5.7(57.3) | 7.2(49.7) | 6.4(80.4) |
| $I/\sigma I$ | 24.3(2.1) | 20.7(3.0) | 23.7(2.0) |
| Completeness (%) | 99.2(96.4) | 99.8(100.0) | 96.6(88.1) |
| Redundancy | 5.3(3.5) | 4.3(4.2) | 5.5(5.4) |
| Refinement | | | |
| Resolution (Å) | 1.65 | 1.90 | 1.70 |
| No. reflections | 56481 | 36890 | 49788 |
| $R_{work}/R_{free}$ | 17.7/21.2 | 16.9/20.4 | 16.9/19.5 |
| No. atoms | | | |
| Protein | 2702 | 2678 | 2763 |
| Ligand/ion | 61/0 | 58/0 | 81/0 |
| Water | 569 | 498 | 425 |
| B-factors | | | |
| Protein | 22.9 | 23.0 | 22.3 |
| Ligand/ion | 21.1/0 | 22.0/0 | 23.6/0 |
| Water | 38.9 | 37.5 | 35.2 |
| R.m.s deviations | | | |
| Bond lengths (Å) | 0.0108 | 0.0101 | 0.0114 |
| Bond angles (°) | 1.4271 | 1.4165 | 1.4750 |

Figure 20
Table 2
| Acyl-CoA donor | Acyl group | Activity of Orf11* |
|---|---|---|
| acetyl-CoA (C$_2$), 20 |  | + |
| butyryl-CoA (C$_4$), 21 |  | + |
| hexanoyl-CoA (C$_6$), 22 |  | + |
| octyl-CoA (C$_8$), 23 |  | + |
| decanoyl-CoA (C$_{10}$), 1 |  | + |
| lauroyl-CoA (C$_{12}$), 24 |  | + |
| myristoyl-CoA (C$_{14}$), 25 |  | + |
| palmitoyl-CoA (C$_{16}$), 26 |  | + |
| stearoyl-CoA (C$_{18}$), 27 |  | + |

Figure 20 (continued)

Table 2 (continued)

| Acyl-CoA donor | Acyl group | Activity of Orf11* |
|---|---|---|
| malonyl-CoA | | - |
| acetoacetyl-CoA, 28 | | + |
| β-hydroxybutyl-CoA, 29 | | + |
| isobutyryl-CoA | | - |
| isovaleryl-CoA, 30 | | + |
| succinyl-CoA, 31 | | + |
| glutaryl-CoA, 32 | | + |
| methylmalonyl-CoA | | - |
| benzoyl-CoA | | - |
| phenylacetyl-CoA, 33 | | + |
| 4-biphenyl acetyl-CoA, 34 | | + |
| 3-naphthlen propionyl-CoA, 35 | | + |

Figure 21

Table 3

| Mutant | Relative activity[a] (%) | Expected functions |
|---|---|---|
| H196A | 5 | an active site residue (general base) |
| S236A | 10 | an active site residue (general acid) |
| H196A/S236A | 0 | active site residues |
| W163S | 38 | a sugar binding site residue (r4-glucosamine of pseudoaglycone) |
| W164S | 46 | a sugar binding site residue (r4-glucosamine of pseudoaglycone) |
| E145A | 79 | a residue for salt bridge formation |
| W237A | 8 | an acyl-CoA binding site residue (decanoyl-CoA) |
| F281S | 2 | a sugar binding site residue (r4-glucosamine of pseudoaglycone) |

Table 4

| Position | 13C-NMR (δ ppm) | 1H-NMR (δ ppm) |
|---|---|---|
| C-1 | 14.4 | 0.85 m |
| C-2 | 22.5 | 1.28 m |
| C-3 | 31.6 | 1.20 m |
| C-4 | 29.5 | 1.23 m |
| C-5 | 28.8 | 1.21 m |
| C-6 | 24.8 | 1.47 m |
| C-7 | 33.9 | 2.20 m |
| C-8 | 173.4 | — |
| C-9 | 63.6 | 3.28 m |

Table 5

| Position | $^{13}$C-NMR (δ ppm) | $^1$H-NMR (δ ppm) |
|---|---|---|
| C-1 | 17.2 | 0.83 m |
| C-2 | 25.3 | 1.22 m |
| C-3 | 34.4 | 1.20 m |
| C-4 | 31.7 | 1.10 m |
| C-5 | 32.0 | 1.23 m |
| C-6 | 28.2 | 1.46 m |
| C-7 | 39.07 | 2.08 m |
| C-8 | 175.4 | — |

Table 6

| Position | 11 | | reference 1 (teicoplanin A2-2) | |
|---|---|---|---|---|
| | 13C-NMR (δ ppm) | 1H-NMR (δ ppm) | 13C-NMR (δ ppm) | 1H-NMR (δ ppm) |
| C-1 | 22.5 | | | 0.82 d (J 6.6) |
| C-2 | 27.4 | | | 1.46 m |
| C-3 | 38.5 | | | 1.07 m |
| C-4 | 26.6 | | | 1.16 m |
| C-5 | 29.2 | | | 1.13 m |
| C-6 | 28.5 | | | 1.23 m |
| C-7 | 24.5 | | | 1.47 m |
| C-8 | 33.7 | | | 2.22 m |
| C-9 | 172.33 | | | --- |
| C-1' | 13.9 | | | 0.85 m |
| C-2' | 22.1 | | | 1.25 m |
| C-3' | 31.2 | | | 1.22 m |
| C-4' | 26.7 | | | 1.08 m |
| C-5' | 29.9 | | | 1.10 m |
| C-6' | 25.2 | | | 1.38 m |
| C-7' | 35.8 | | | 2.00 m |
| C-8' | 169.61 | | | --- |
| C-9' | 63.12 | | | 3.35 m |

TEICOPLANIN ANALOGS AND USES THEREOF

RELATED APPLICATIONS

This application is a national stage filing under 35 U.S.C. § 371 of international PCT application PCT/US2015/012914, filed Jan. 26, 2015, which claims priority under 35 U.S.C. § 119(e) to U.S. Provisional Patent Application Ser. No. 61/932,325, filed Jan. 28, 2014. Each of the prior applications is incorporated by reference in its entirety.

BACKGROUND

Teicoplanin (Tei) is a glycopeptide antibiotic that has bactericidal activity against Gram positive aerobic and anaerobic bacteria. It inhibits the growth of susceptible organisms by interfering with the biosynthesis of the cell-wall at a site different from that affected by beta-lactam antibiotics. Teicoplanin is a mixture of glycopeptide components which, on the basis of high performance liquid chromatography (HPLC) separation, are currently classified into six main subcomponents (as individual or as a group) according to their alkyl side chain and therefore by their polarity in elution in the referenced chromatographic system.

Bacteria have the ability to generate resistance to antibiotics through lateral gene transfer, mutation of enzymes, or the expression of enzymes which actively pump the antibiotic out of the cell or break it down. Over the past 10 years, resistance to existing antibiotics has become a significant problem. In practice, strains such as methicillin-resistant *Staphylococcus Aureus* (MRSA), methicillin-resistant *Staphylococcus Epidermidis* (MRSE), penicillin-resistant *Streptococcus pneumonia*, quinolone-resistant *Staphylococcus Aureus* (QRSA), vancomycin-resistant *Staphylococcus Aureus* (VRSA), vancomycin-resistant *Enterococci* (VRE), and multi-drug resistant *Mycobacterium tuberculosis* show resistance to most antibiotics in use. Glycopeptide is generally the last line antibiotic to treat multidrug-resistant gram-positive pathogens MRSA and VRE. This class of antibiotics is empowered by the N-acyltransferase, attaching a long aliphatic chain on the glucosamine moiety at the central residue of glycopeptide pseudoaglycone. Thus, it is urgently demanded to develop new antibiotics and new mechanism of action to treat and/or prevent bacterial infections, in particular, to overcome the bacterial resistance problem.

SUMMARY

The present invention provides compounds of Formula (I) and pharmaceutical compositions thereof, which are useful in inhibiting bacterial growth (e.g. Gram positive aerobic and anaerobic bacteria). The present invention further provides methods of using the compounds described herein, or a pharmaceutically acceptable salt, solvate, hydrate, polymorph, co-crystal, tautomer, stereoisomer, isotopically labeled derivative, or prodrug thereof, and pharmaceutical compositions thereof, to inhibit bacterial growth. The present invention further provides methods of using the compounds described herein, or a pharmaceutically acceptable salt, solvate, hydrate, polymorph, co-crystal, tautomer, stereoisomer, isotopically labeled derivative, or prodrug thereof, and pharmaceutical compositions thereof, to treat or prevent bacterial infections.

In one aspect, this invention features compounds of the following formula:

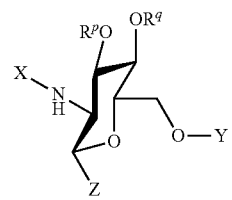

(I)

or a pharmaceutically acceptable salt thereof,
wherein
  X is of Formula (i):

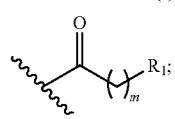

(i)

Y is hydrogen or of Formula (ii):

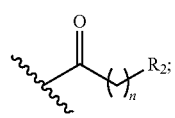

(ii)

and
  Z is of Formula (iii):

(iii)

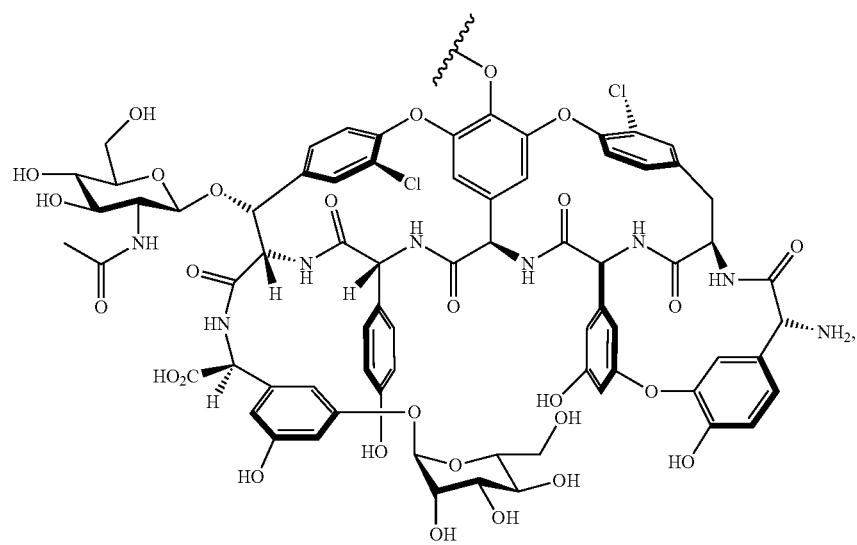

or a derivative thereof;

each instance of $R_1$ and $R_2$ is, independently, optionally substituted alkyl, optionally substituted alkenyl, optionally substituted alkynyl, optionally substituted carbocyclyl, optionally substituted heterocyclyl, optionally substituted aryl, optionally substituted heteroaryl, or —C(=O)$R^C$;

each instance of $R^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or —O$R^O$;

each instance of $R^O$ is independently hydrogen, optionally substituted alkyl, or an oxygen protecting group;

each of $R^p$ and $R^q$ is independently hydrogen, optionally substituted $C_{1-6}$ alkyl, an optionally substituted carbohydrate, or an oxygen protecting group;

m is 0 or an integer of 1 to 15, inclusive; and n is 0 or an integer of 1 to 15, inclusive;

provided that when Y is hydrogen, X is not of the formula

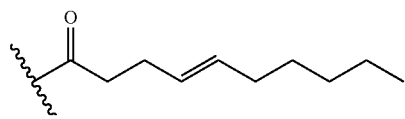

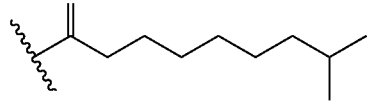

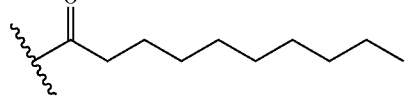

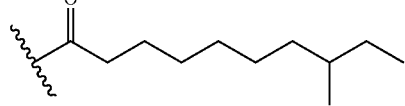

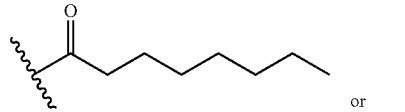

or

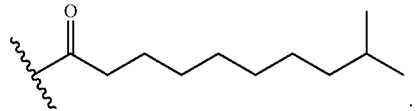

In certain embodiments, a provided compound is of Formula (I-a):

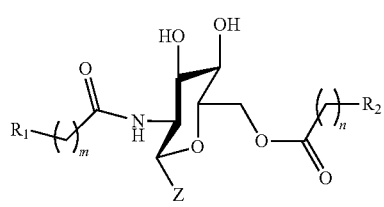

(I-a)

or a pharmaceutically acceptable salt thereof, wherein $R_1$, m, Z, n, and $R_2$ are as defined herein.

In some embodiments of Formula (I-a), it is provided that when

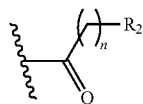

is of the formula

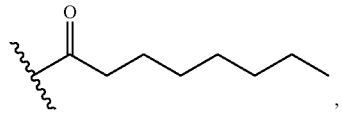 [SMILES: *C(=O)CCCCCCC]

then

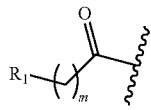

is not of the formula

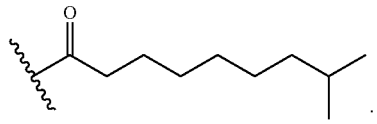 [SMILES: *C(=O)CCCCCCC(C)C]

In certain embodiments, a provided compound is of Formula (I-b):

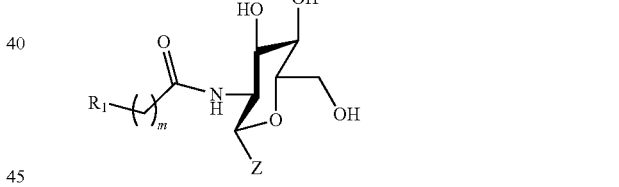

(I-b)

or a pharmaceutically acceptable salt thereof, wherein $R_1$, m, and Z are as defined herein.

As generally defined herein, $R^p$ is hydrogen, optionally substituted $C_{1-6}$ alkyl, an optionally substituted carbohydrate, or an oxygen protecting group. In certain embodiments, $R^p$ is hydrogen. In certain embodiments, $R^p$ is optionally substituted $C_{1-6}$ alkyl, an optionally substituted carbohydrate, or an oxygen protecting group.

As generally defined herein, $R^q$ is hydrogen, optionally substituted $C_{1-6}$ alkyl, an optionally substituted carbohydrate, or an oxygen protecting group. In certain embodiments, $R^q$ is hydrogen. In certain embodiments, $R^q$ is optionally substituted $C_{1-6}$ alkyl, an optionally substituted carbohydrate, or an oxygen protecting group.

As generally defined herein, $R_1$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or —C(=O)$R^C$, wherein $R^C$ is as defined herein.

In certain embodiments, $R_1$ is optionally substituted alkyl. In certain embodiments, $R_1$ is optionally substituted $C_{1-15}$ alkyl. In certain embodiments, $R_1$ is optionally substituted $C_{1-10}$ alkyl. In certain embodiments, $R_1$ is optionally substituted $C_{1-6}$ alkyl. In certain embodiments, $R_1$ is substituted alkyl. In certain embodiments, $R_1$ is substituted $C_{1-15}$ alkyl. In certain embodiments, $R_1$ is optionally substituted $C_{1-15}$ alkylaryl, substituted $C_{1-15}$ alkylalkynyl, or optionally substituted $C_{1-15}$ alkylhydroxyl.

In certain embodiments, $R_1$ is substituted $C_{1-10}$ alkyl. In certain embodiments, $R_1$ is substituted $C_{1-6}$ alkyl. In certain embodiments, $R_1$ is unsubstituted alkyl. In certain embodiments, $R_1$ is unsubstituted $C_{1-15}$ alkyl. In certain embodiments, $R_1$ is unsubstituted $C_{1-10}$ alkyl. In certain embodiments, $R_1$ is unsubstituted $C_{1-6}$ alkyl.

In some embodiments, $R_1$ is optionally substituted alkenyl. In some embodiments, $R_1$ is optionally substituted $C_{2-15}$ alkenyl. In some embodiments, $R_1$ is optionally substituted $C_{2-10}$ alkenyl. In some embodiments, $R_1$ is substituted $C_{2-15}$ alkenyl. In some embodiments, $R_1$ is substituted $C_{2-10}$ alkenyl. In some embodiments, $R_1$ is unsubstituted $C_{2-15}$ alkenyl. In some embodiments, $R_1$ is unsubstituted $C_{2-10}$ alkenyl.

In some embodiments, $R_1$ is optionally substituted alkynyl. In some embodiments, $R_1$ is optionally substituted $C_{2-15}$ alkynyl. In some embodiments, $R_1$ is optionally substituted $C_{2-10}$ alkynyl.

In some embodiments, $R_1$ is optionally substituted carbocyclyl, optionally substituted heterocyclyl, optionally substituted aryl, optionally substituted heteroaryl, or $-C(=O)R^C$. In some embodiments, $R_1$ is optionally substituted $C_{3-6}$ carbocyclyl, optionally substituted 3- to 6-membered heterocyclyl, optionally substituted aryl, optionally substituted heteroaryl, or $-C(=O)R^C$. In some embodiments, $R_1$ is optionally substituted carbocyclyl. In some embodiments, $R_1$ is optionally substituted $C_{3-6}$ carbocyclyl. In some embodiments, $R_1$ is optionally substituted heterocyclyl. In some embodiments, $R_1$ is optionally substituted 3- to 6-membered heterocyclyl. In some embodiments, $R_1$ is optionally substituted 6-membered heterocyclyl with one heteroatom selected from the group consisting of N, O, and S. In some embodiments, $R_1$ is optionally substituted 6-membered heterocyclyl with two heteroatoms each independently selected from the group consisting of N, O, and S. In some embodiments, $R_1$ is optionally substituted 6-membered heterocyclyl with three heteroatoms each independently selected from the group consisting of N, O, and S. In some embodiments, $R_1$ is optionally substituted 5-membered heterocyclyl with one heteroatom selected from the group consisting of N, O, and S. In some embodiments, $R_1$ is optionally substituted 5-membered heterocyclyl with two heteroatoms each independently selected from the group consisting of N, O, and S. In some embodiments, $R_1$ is optionally substituted aryl. In some embodiments, $R_1$ is optionally substituted phenyl. In some embodiments, $R_1$ is phenyl. In some embodiments, $R_1$ is optionally substituted heteroaryl. In some embodiments, $R_1$ is optionally substituted 6-membered heteroaryl with one heteroatom selected from the group consisting of N, O, and S. In some embodiments, $R_1$ is optionally substituted 6-membered heteroaryl with two heteroatoms each independently selected from the group consisting of N, O, and S. In some embodiments, $R_1$ is optionally substituted 5-membered heteroaryl with one heteroatom selected from the group consisting of N, O, and S. In some embodiments, $R_1$ is optionally substituted 5-membered heteroaryl with two heteroatoms each independently selected from the group consisting of N, O, and S.

In some embodiments, $R_1$ is $-C(=O)R^C$, wherein each instance of $R^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or $OR^O$; wherein each instance of $R^O$ is independently hydrogen, optionally substituted alkyl, or an oxygen protecting group. In some embodiments, $R_1$ is $-C(=O)R^C$, wherein $R^C$ is optionally substituted alkyl. In some embodiments, $R_1$ is $-C(=O)R^C$, wherein $R^C$ is optionally substituted $C_{1-15}$ alkyl. In some embodiments, $R_1$ is $-C(=O)R^C$, wherein $R^C$ is optionally substituted $C_{1-10}$ alkyl. In some embodiments, $R_1$ is $-C(=O)R^C$, wherein $R^C$ is optionally substituted $C_{1-6}$ alkyl. In some embodiments, $R_1$ is $-C(=O)R^C$, wherein $R^C$ is methyl, ethyl, n-propyl, or iso-propyl. In some embodiments, $R_1$ is $-C(=O)R^C$, wherein $R^C$ is $OR^O$; and $R^O$ is independently hydrogen, optionally substituted alkyl, or an oxygen protecting group. In some embodiments, $R_1$ is $-C(=O)R^C$, wherein $R^C$ is OH. In some embodiments, $R_1$ is $-C(=O)R^C$, wherein $R^C$ is $OR^O$; and $R^O$ is optionally substituted alkyl. In some embodiments, $R_1$ is $-C(=O)R^C$, wherein $R^C$ is $OR^O$; and $R^O$ is optionally substituted $C_{1-15}$ alkyl. In some embodiments, $R_1$ is $-C(=O)R^C$, wherein $R^C$ is $OR^O$; and $R^O$ is optionally substituted $C_{1-10}$ alkyl. In some embodiments, $R_1$ is $-C(=O)R^C$, wherein $R^C$ is $OR^O$; and $R^O$ is optionally substituted $C_{1-6}$ alkyl. In some embodiments, $R_1$ is $-C(=O)R^C$, wherein $R^C$ is $OR^O$; and $R^O$ is methyl, ethyl, n-propyl, or iso-propyl. In some embodiments, $R_1$ is $-C(=O)R^C$, wherein $R^C$ is $OR^O$; and $R^O$ is an oxygen protecting group.

In certain embodiments, $R_1$ is of one of the following formulae:

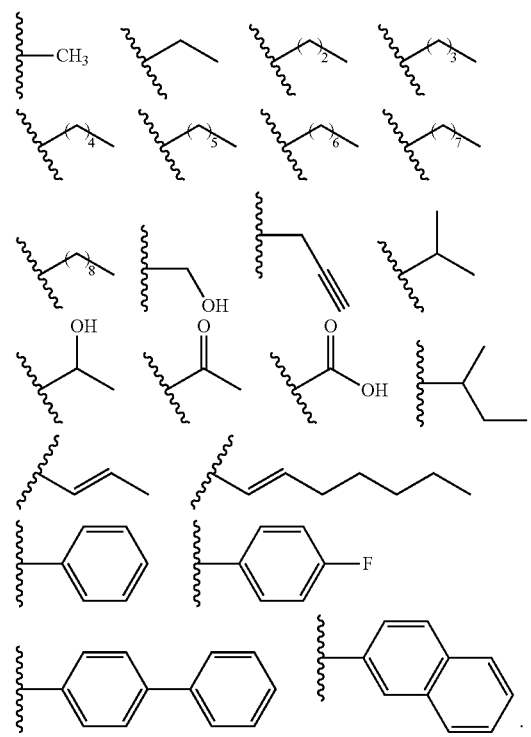

As generally defined herein, $R_2$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or —C(=O)R$^C$, wherein R$^C$ is as defined herein. In certain embodiments, R$_2$ is optionally substituted alkyl. In certain embodiments, R$_2$ is optionally substituted C$_{1-15}$ alkyl. In certain embodiments, R$_2$ is optionally substituted C$_{1-10}$ alkyl. In certain embodiments, R$_2$ is optionally substituted C$_{1-6}$ alkyl. In certain embodiments, R$_2$ is substituted alkyl. In certain embodiments, R$_2$ is substituted C$_{1-15}$ alkyl. In some embodiments, R$_2$ is optionally substituted C$_{1-15}$ alkylaryl, substituted C$_{1-15}$ alkylalkynyl, or optionally substituted C$_{1-15}$ alkylhydroxyl. In certain embodiments, R$_2$ is substituted C$_{1-10}$ alkyl. In certain embodiments, R$_2$ is substituted C$_{1-6}$ alkyl. In certain embodiments, R$_2$ is unsubstituted alkyl. In certain embodiments, R$_2$ is unsubstituted C$_{1-15}$ alkyl. In certain embodiments, R$_2$ is unsubstituted C$_{1-10}$ alkyl. In certain embodiments, R$_2$ is unsubstituted C$_{1-6}$ alkyl.

In some embodiments, R$_2$ is optionally substituted alkenyl. In some embodiments, R$_2$ is optionally substituted C$_{2-15}$ alkenyl. In some embodiments, R$_2$ is optionally substituted C$_{2-10}$ alkenyl. In some embodiments, R$_2$ is substituted C$_{2-15}$ alkenyl. In some embodiments, R$_2$ is substituted C$_{2-10}$ alkenyl. In some embodiments, R$_2$ is unsubstituted C$_{2-15}$ alkenyl. In some embodiments, R$_2$ is unsubstituted C$_{2-10}$ alkenyl.

In some embodiments, R$_2$ is optionally substituted alkynyl. In some embodiments, R$_2$ is optionally substituted C$_{2-15}$ alkynyl. In some embodiments, R$_2$ is optionally substituted C$_{2-10}$ alkynyl.

In some embodiments, R$_2$ is optionally substituted carbocyclyl, optionally substituted heterocyclyl, optionally substituted aryl, optionally substituted heteroaryl, or —C(=O)R$^C$. In some embodiments, R$_2$ is optionally substituted C$_{3-6}$ carbocyclyl, optionally substituted 3- to 6-membered heterocyclyl, optionally substituted aryl, optionally substituted heteroaryl, or —C(=O)R$^C$. In some embodiments, R$_2$ is optionally substituted carbocyclyl. In some embodiments, R$_2$ is optionally substituted C$_{3-6}$ carbocyclyl. In some embodiments, R$_2$ is optionally substituted heterocyclyl. In some embodiments, R$_2$ is optionally substituted 3- to 6-membered heterocyclyl. In some embodiments, R$_2$ is optionally substituted 6-membered heterocyclyl with one heteroatom selected from the group consisting of N, O, and S. In some embodiments, R$_2$ is optionally substituted 6-membered heterocyclyl with two heteroatoms each independently selected from the group consisting of N, O, and S. In some embodiments, R$_2$ is optionally substituted 6-membered heterocyclyl with three heteroatoms each independently selected from the group consisting of N, O, and S. In some embodiments, R$_2$ is optionally substituted 5-membered heterocyclyl with one heteroatom selected from the group consisting of N, O, and S. In some embodiments, R$_2$ is optionally substituted 5-membered heterocyclyl with two heteroatoms each independently selected from the group consisting of N, O, and S. In some embodiments, R$_2$ is optionally substituted aryl. In some embodiments, R$_2$ is optionally substituted phenyl. In some embodiments, R$_2$ is phenyl. In some embodiments, R$_2$ is optionally substituted heteroaryl. In some embodiments, R$_2$ is optionally substituted 6-membered heteroaryl with one heteroatom selected from the group consisting of N, O, and S. In some embodiments, R$_2$ is optionally substituted 6-membered heteroaryl with two heteroatoms each independently selected from the group consisting of N, O, and S. In some embodiments, R$_2$ is optionally substituted 5-membered heteroaryl with one heteroatom selected from the group consisting of N, O, and S. In some embodiments, R$_2$ is optionally substituted 5-membered heteroaryl with two heteroatoms each independently selected from the group consisting of N, O, and S.

In some embodiments, R$_2$ is —C(=O)R$^C$, wherein each instance of R$^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or OR$^O$; wherein each instance of R$^O$ is independently hydrogen, optionally substituted alkyl, or an oxygen protecting group. In some embodiments, R$_2$ is —C(=O)R$^C$, wherein R$^C$ is optionally substituted alkyl. In some embodiments, R$_2$ is —C(=O)R$^C$, wherein R$^C$ is optionally substituted C$_{1-15}$ alkyl. In some embodiments, R$_2$ is —C(=O)R$^C$, wherein R$^C$ is optionally substituted C$_{1-10}$ alkyl. In some embodiments, R$_2$ is —C(=O)R$^C$, wherein R$^C$ is optionally substituted C$_{1-6}$ alkyl. In some embodiments, R$_2$ is —C(=O)R$^C$, wherein R$^C$ is methyl, ethyl, n-propyl, or iso-propyl. In some embodiments, R$_2$ is —C(=O)R$^C$, wherein R$^C$ is OR$^O$; and R$^O$ is independently hydrogen, optionally substituted alkyl, or an oxygen protecting group. In some embodiments, R$_2$ is —C(=O)R$^C$, wherein R$^C$ is OH. In some embodiments, R$_2$ is —C(=O)R$^C$, wherein R$^C$ is OR$^O$; and R$^O$ is optionally substituted alkyl. In some embodiments, R$_2$ is —C(=O)R$^C$, wherein R$^C$ is OR$^O$; and R$^O$ is optionally substituted C$_{1-15}$ alkyl. In some embodiments, R$_2$ is —C(=O)R$^C$, wherein R$^C$ is OR$^O$; and R$^O$ is optionally substituted C$_{1-10}$ alkyl. In some embodiments, R$_2$ is —C(=O)R$^C$, wherein R$^C$ is OR$^O$; and R$^O$ is optionally substituted C$_{1-6}$ alkyl. In some embodiments, R$_2$ is —C(=O)R$^C$, wherein R$^C$ is OR$^O$; and R$^O$ is methyl, ethyl, n-propyl, or iso-propyl. In some embodiments, R$_2$ is —C(=O)R$^C$, wherein R$^C$ is OR$^O$; and R$^O$ is an oxygen protecting group.

In some embodiments, R$_2$ is one of the following formulae:

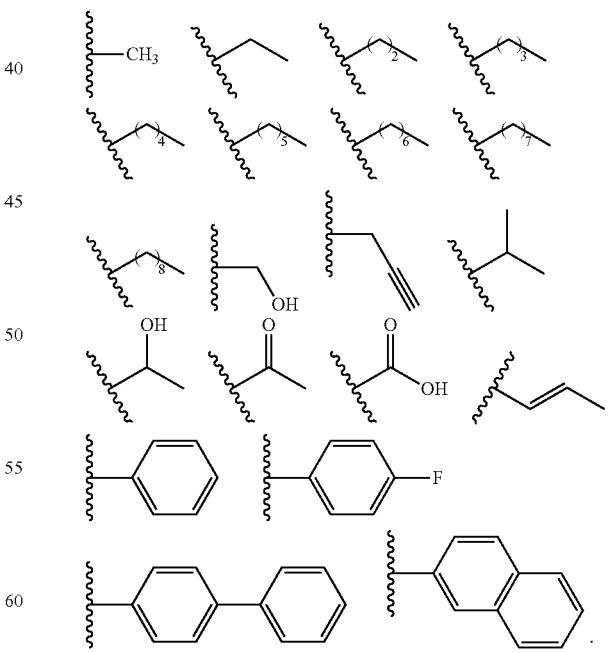

As generally defined herein, m is 0 or an integer of 1 to 15, inclusive. In certain embodiments, m is 0. In certain embodiments, m is an integer of 1 to 15, inclusive. In certain embodiments, m is an integer of 5 to 15, inclusive. In certain embodiments, m is an integer of 5 to 10, inclusive. In certain embodiments, m is an integer of 10 to 15, inclusive. In certain embodiments, m is an integer of 1 to 10, inclusive. In certain embodiments, m is an integer of 1 to 5, inclusive.

As generally defined herein, n is 0 or an integer of 1 to 15, inclusive. In certain embodiments, n is 0. In certain embodiments, n is an integer of 1 to 15, inclusive. In certain embodiments, n is an integer of 5 to 15, inclusive. In certain embodiments, n is an integer of 5 to 10, inclusive. In certain embodiments, n is an integer of 10 to 15, inclusive. In certain embodiments, n is an integer of 1 to 10, inclusive. In certain embodiments, n is an integer of 1 to 5, inclusive.

As generally defined herein, Y is hydrogen or of Formula (ii):

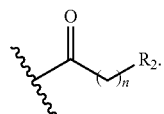

In certain embodiments, Y is hydrogen. In certain embodiments, Y is hydrogen or of Formula (ii):

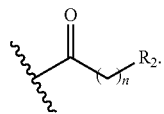

In certain embodiments, Formula (i)

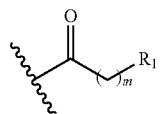

is of one of the following formulae:

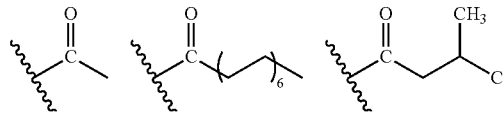

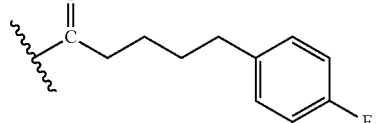

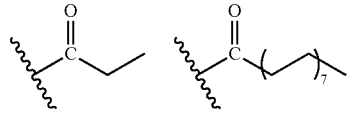

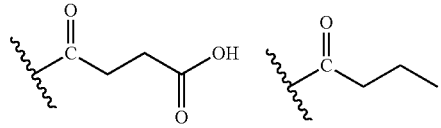

-continued

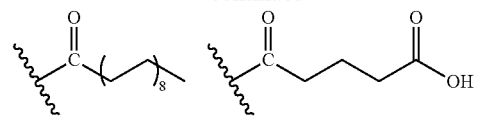

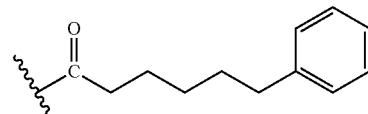

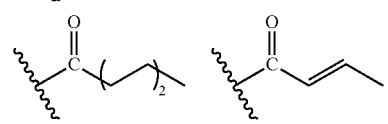

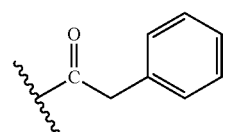

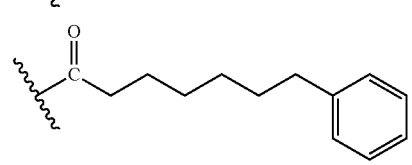

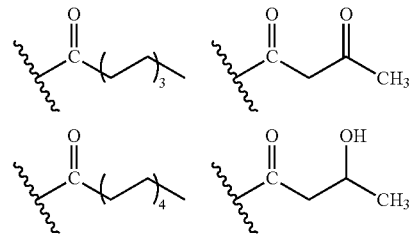

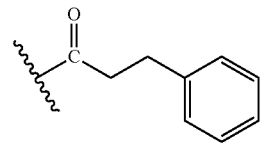

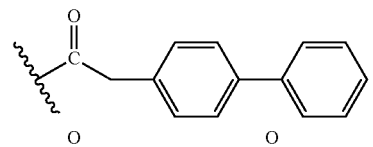

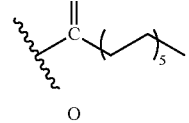

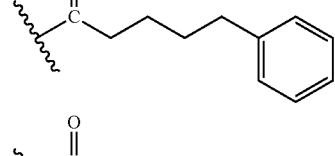

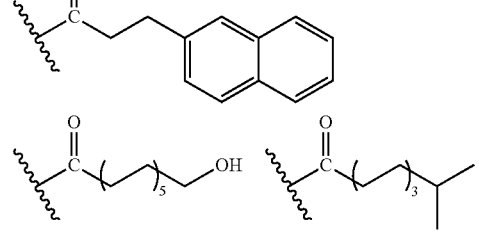

-continued
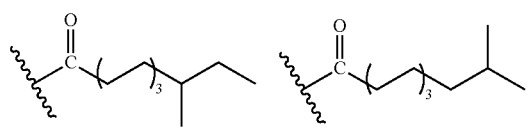
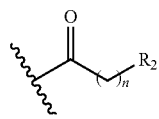
In certain embodiments, Formula (ii)
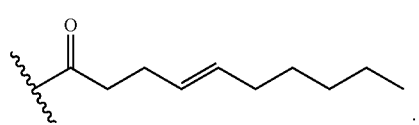
(ii)
is of one of the following formulae:
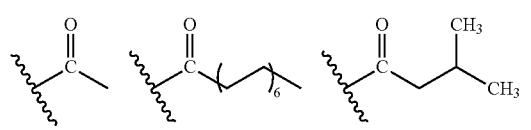
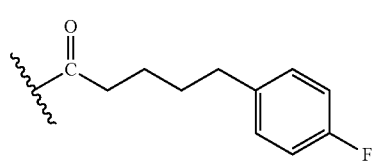
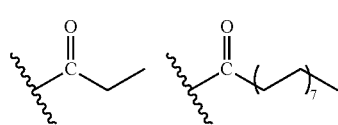
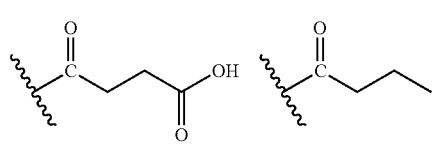
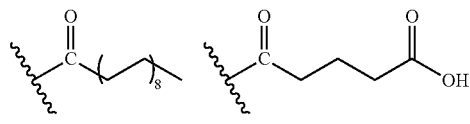
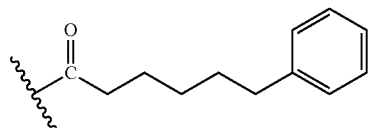
-continued
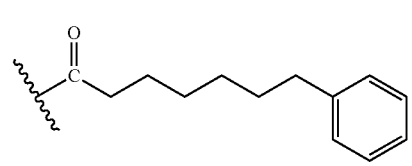
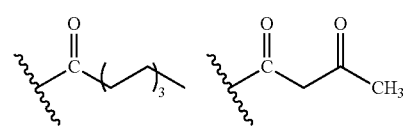
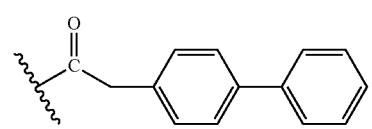
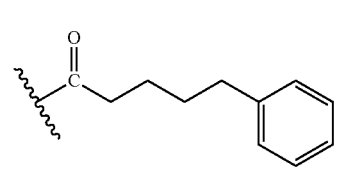
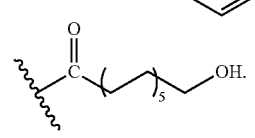

As generally defined herein, Z is of Formula (iii):

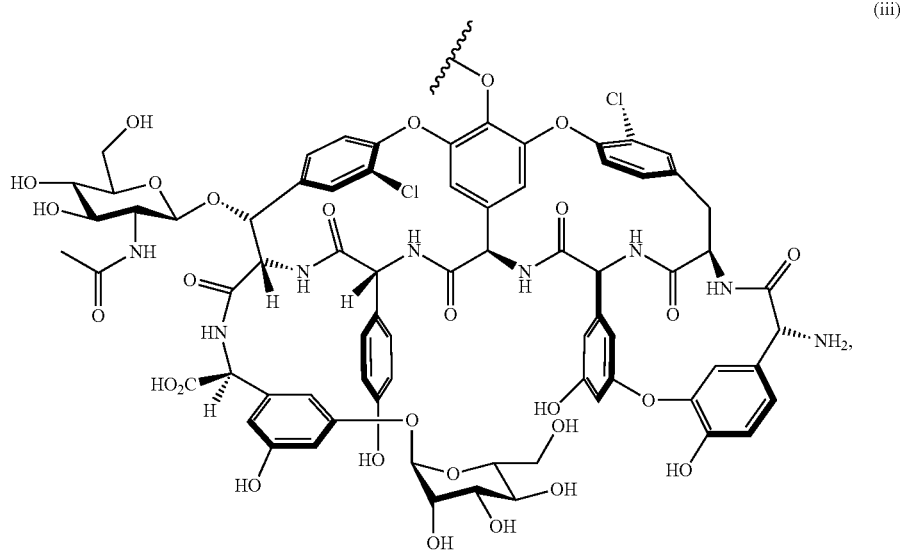

or a derivative thereof. As used herein, a derivative of Formula (iii) refers to a compound with one or more suitable substitutions (e.g., protecting groups) on any hydrogen, and/or any functional group (e.g., hydroxyl, amino, and/or carboxylic acid groups) in Formula (iii).

As used herein, amino protecting groups (also nitrogen protecting groups) include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein.

Hydroxyl and carboxylic acid protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, each instance of R$^{aa}$ is, independently, selected from $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; and each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S.

In certain embodiments, a provided compound is one of the compounds in Table A1.

TABLE A1

Exemplified Compounds

| Cpd No. | Structure |
|---|---|
| 20 | 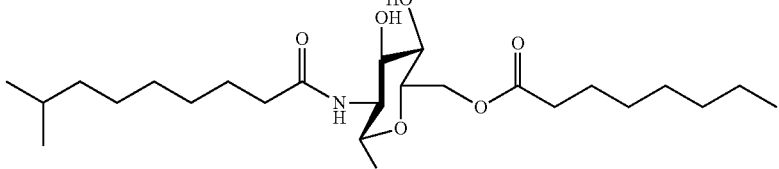 |
| 21 | 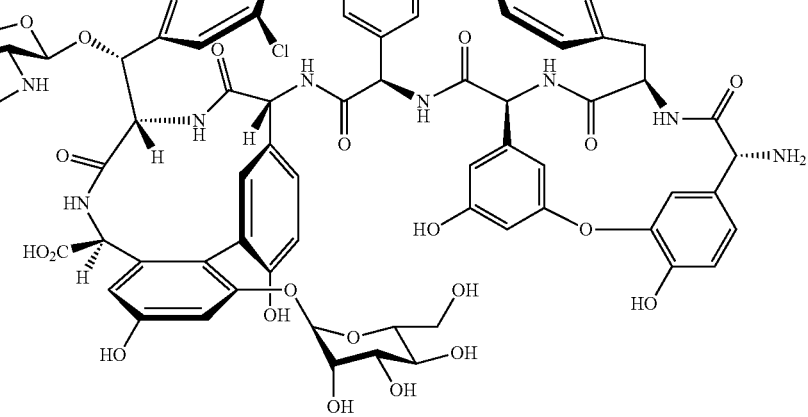 |

TABLE A1-continued
Exemplified Compounds
| Cpd No. | Structure |
|---|---|
| 22 | 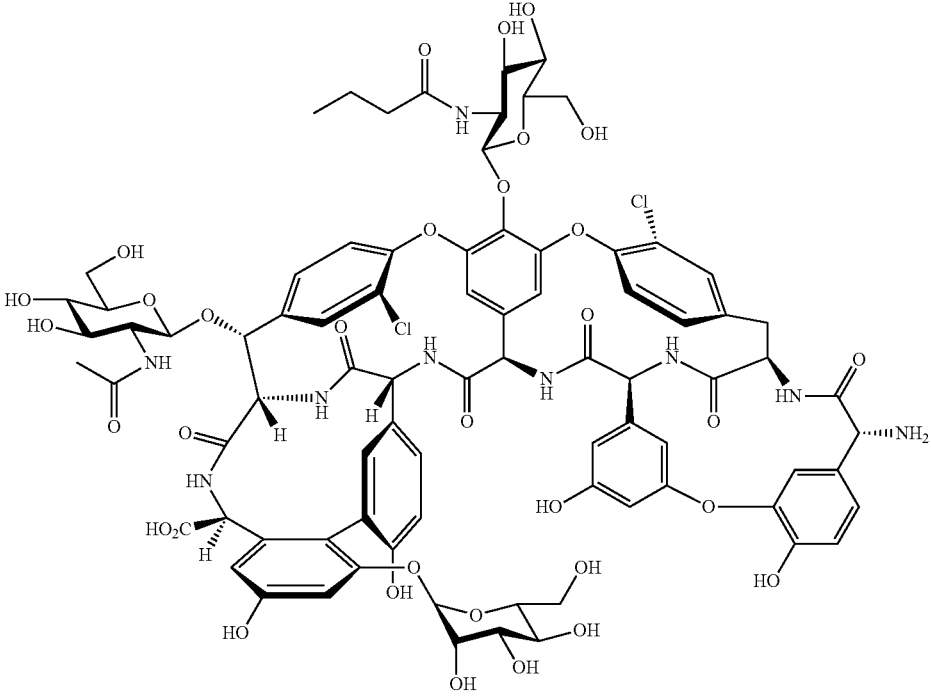 |
| 23 | 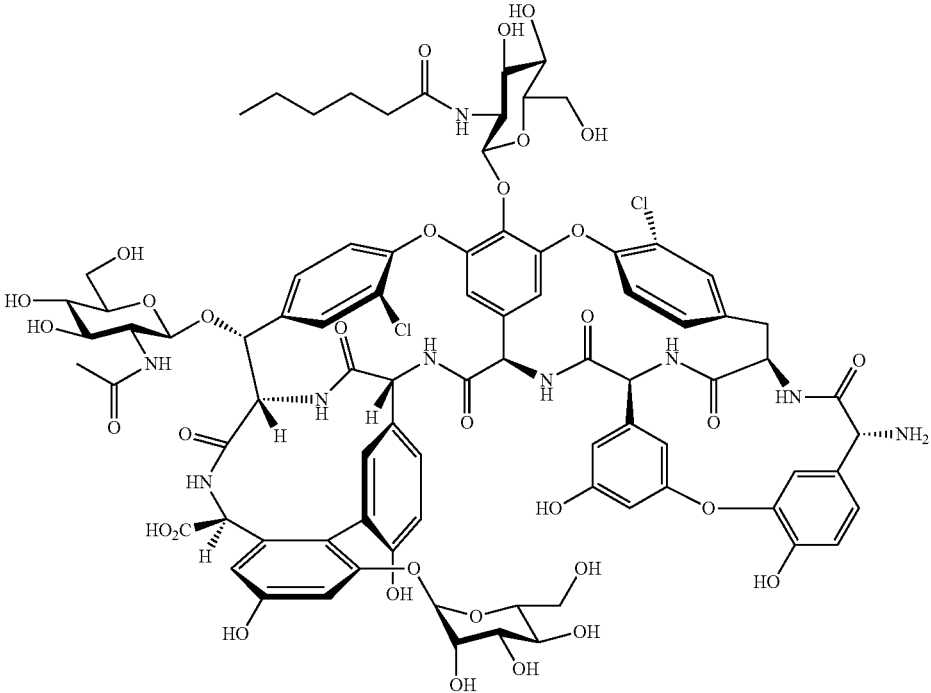 |

TABLE A1-continued
Exemplified Compounds
| Cpd No. | Structure |
|---|---|
| 24 | 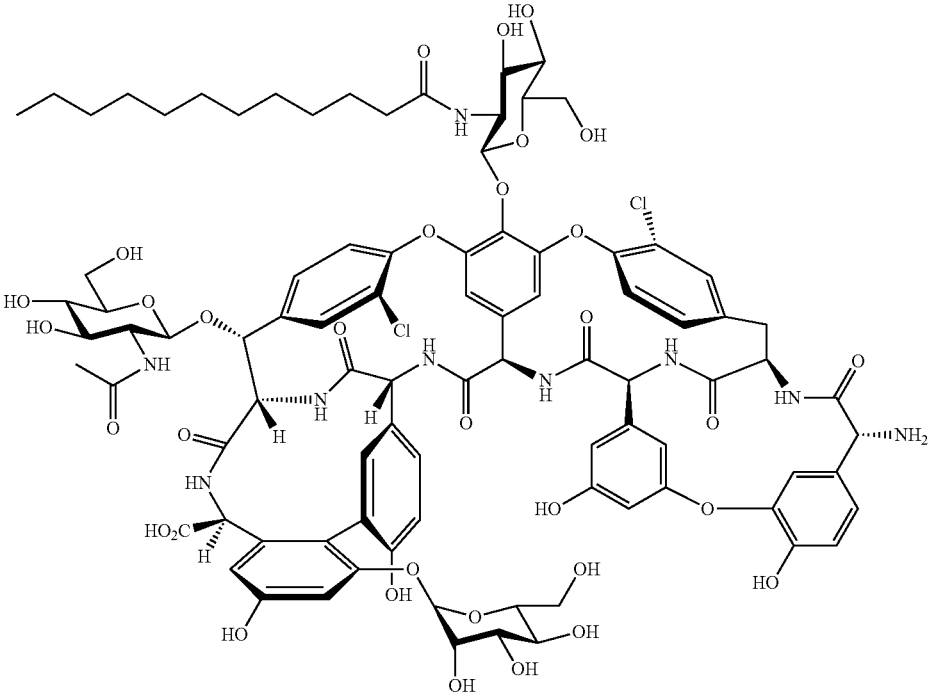 |
| 25 | 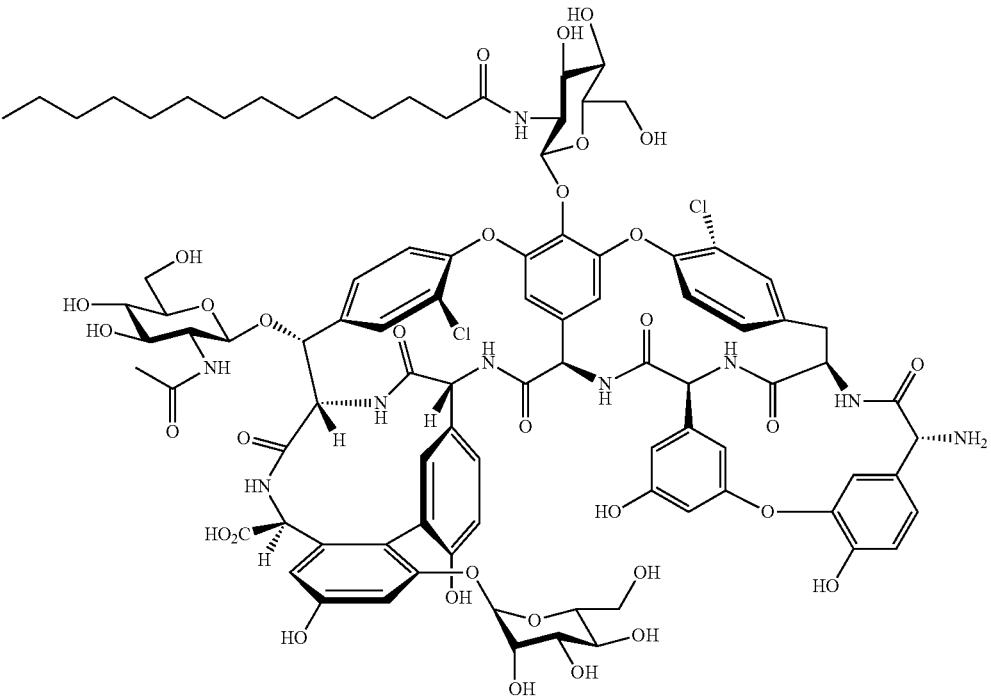 |

TABLE A1-continued
Exemplified Compounds
| Cpd No. | Structure |
|---|---|
| 26 | 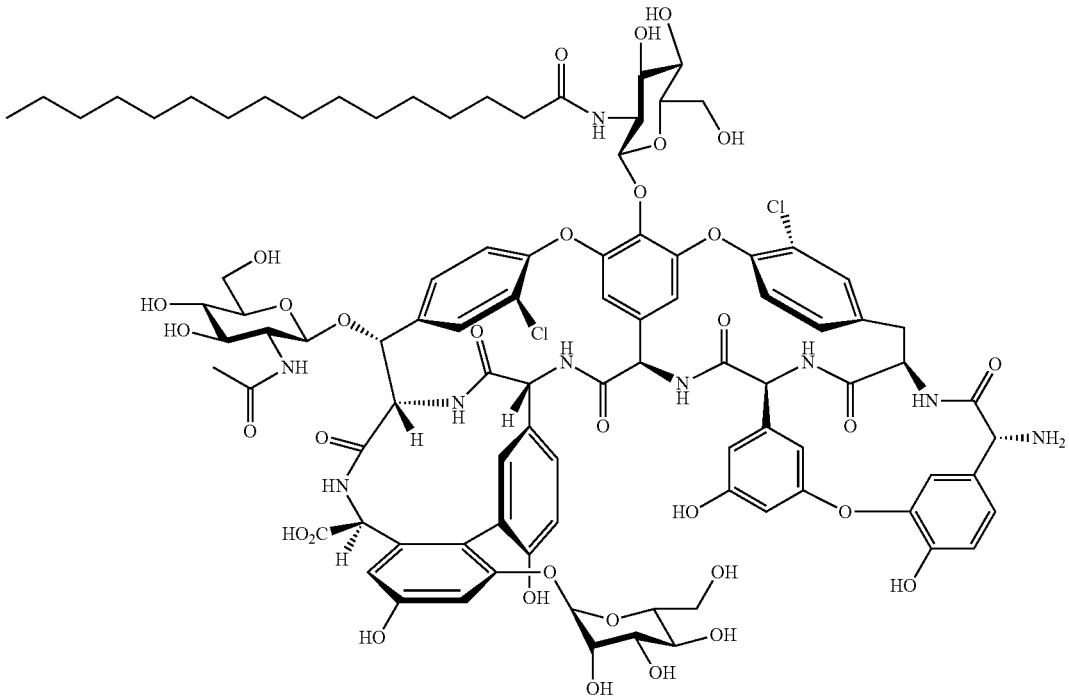 |
| 27 | 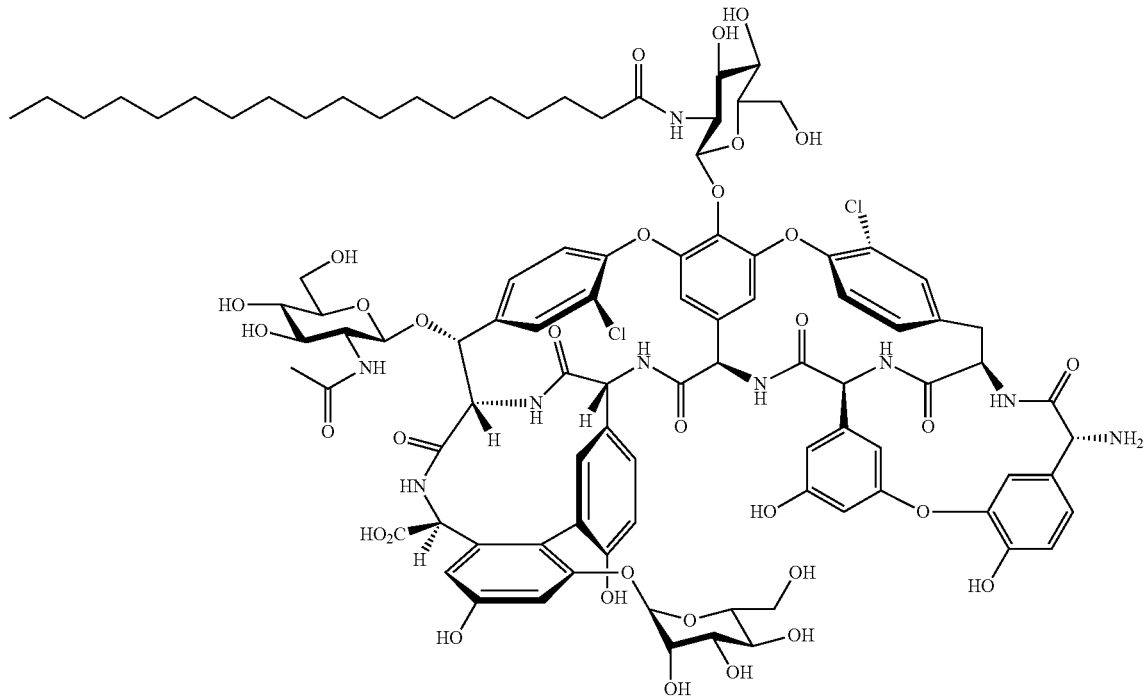 |

TABLE A1-continued

Exemplified Compounds

| Cpd No. | Structure |
|---|---|
| 28 | *(chemical structure)* |
| 29 | *(chemical structure)* |

TABLE A1-continued
Exemplified Compounds
| Cpd No. | Structure |
|---|---|
| 30 | 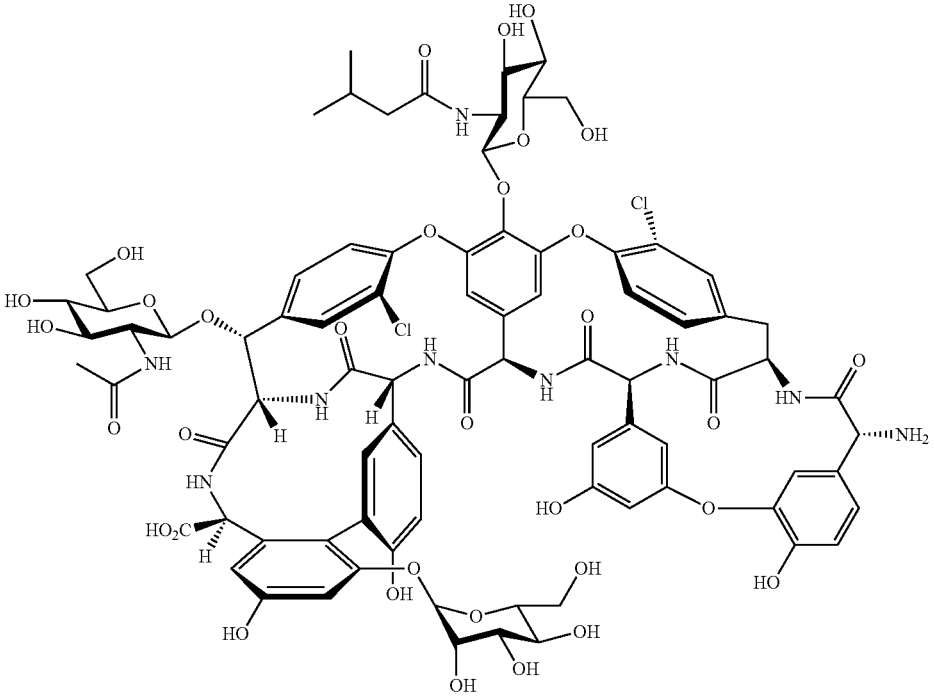 |
| 31 | 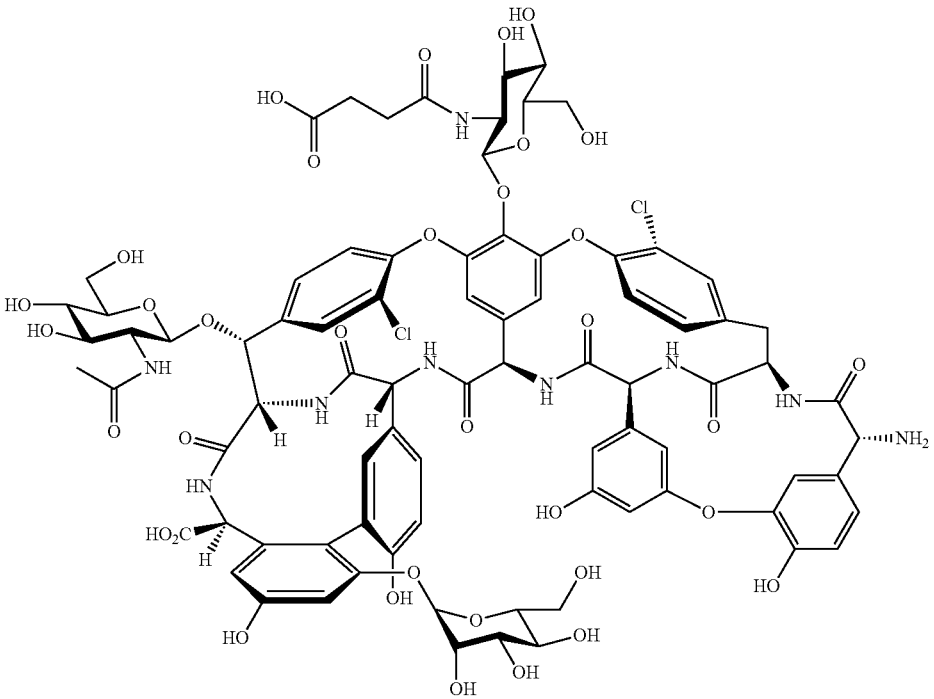 |

TABLE A1-continued
Exemplified Compounds
| Cpd No. | Structure |
|---|---|
| 32 | 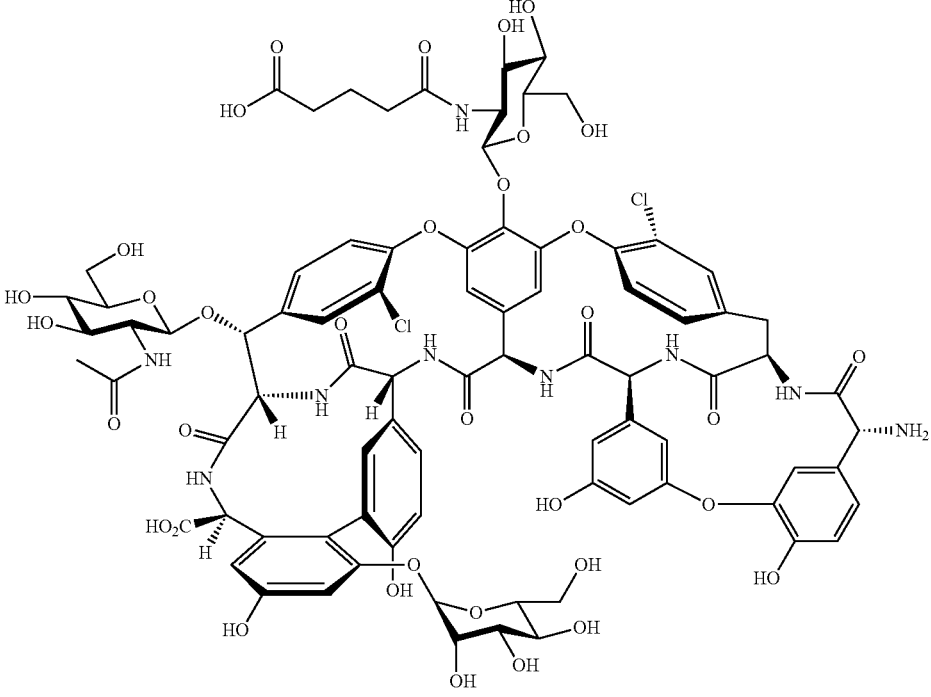 |
| 33 | 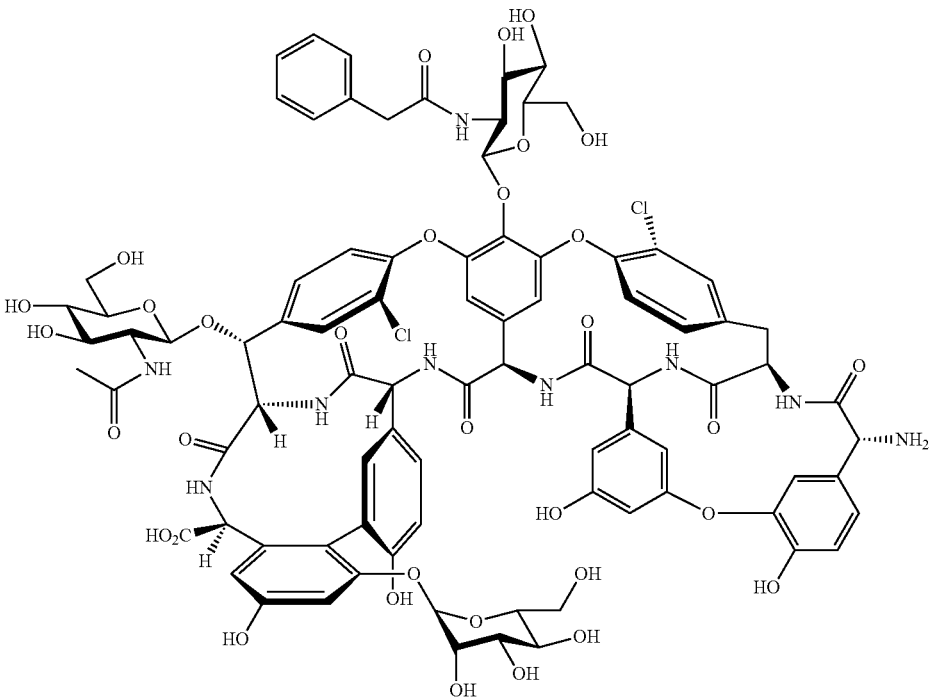 |

TABLE A1-continued
Exemplified Compounds
| Cpd No. | Structure |
|---|---|
| 34 | 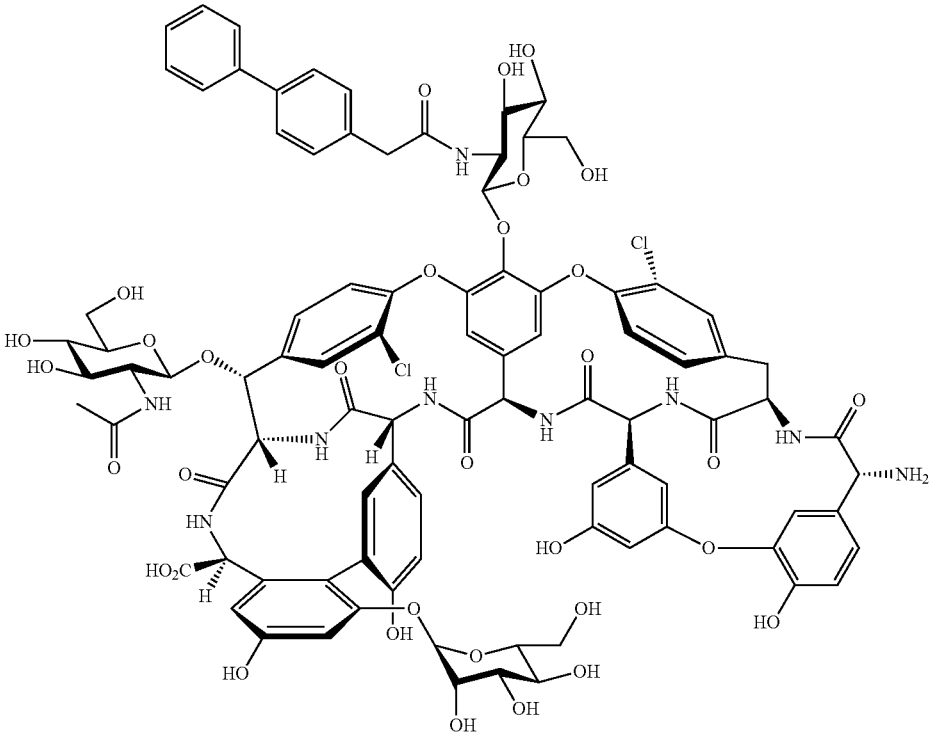 |
| 35 | 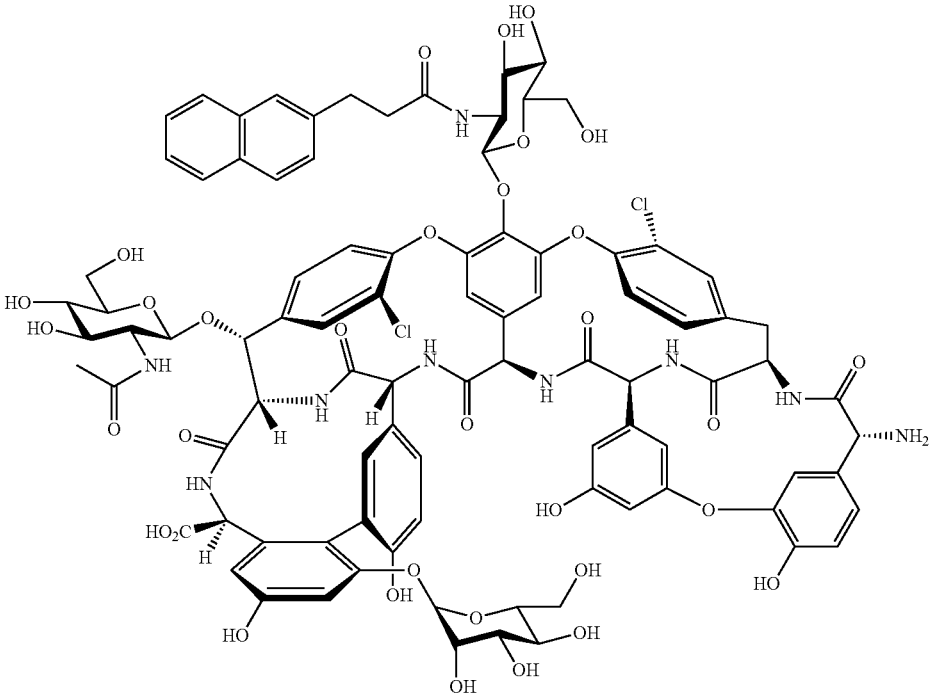 |

TABLE A1-continued

Exemplified Compounds

| Cpd No. | Structure |
|---|---|
| | 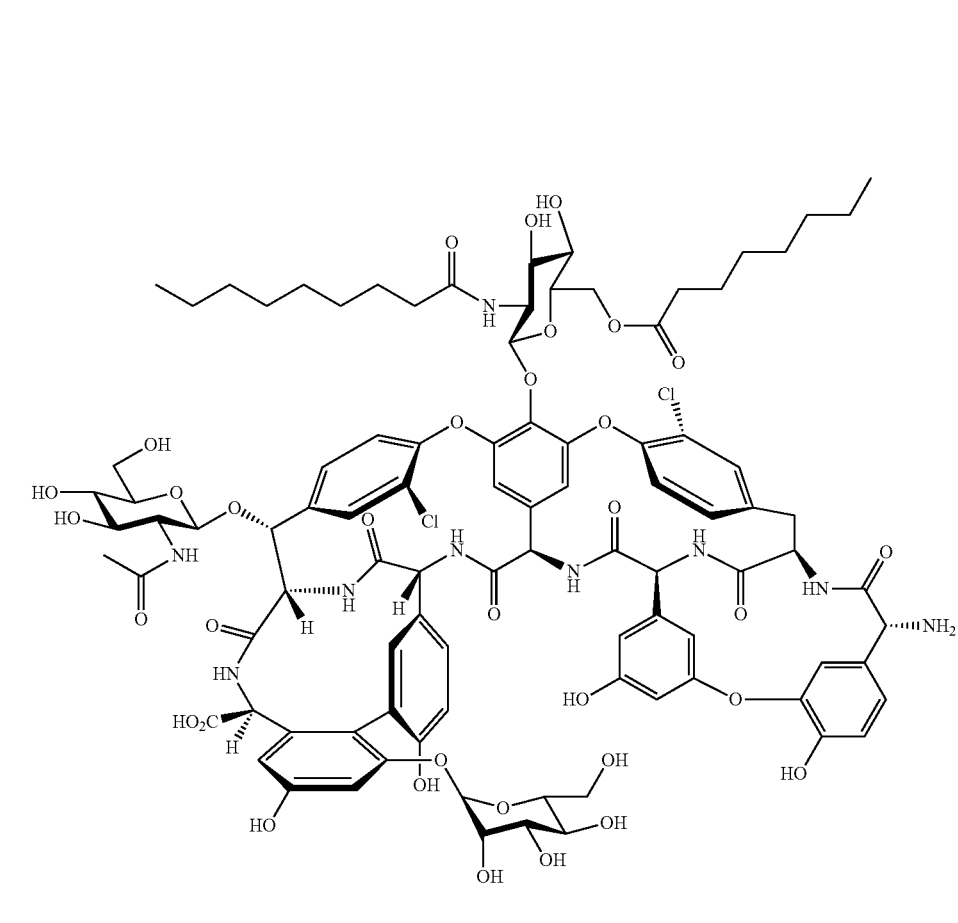 |

Another aspect of the present invention provides a method of preparing a teicoplanin analog, comprising incubating a mixture comprising a long-chain acyltransferase, an acyl-acceptor, and an acyl-donor under suitable conditions allowing for occurrence of the enzymatic reaction catalyzed by the long-chain acyltransferase to produce the teicoplanin analog, wherein:

the acyl-acceptor is of Formula (I-c)

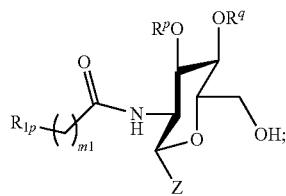

(I-c)

the acyl-donor is of Formula (S-i) or (S-ii)

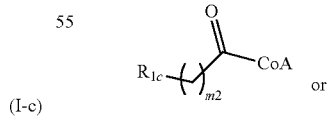

(S-i)

(S-ii)

Z is of the formula

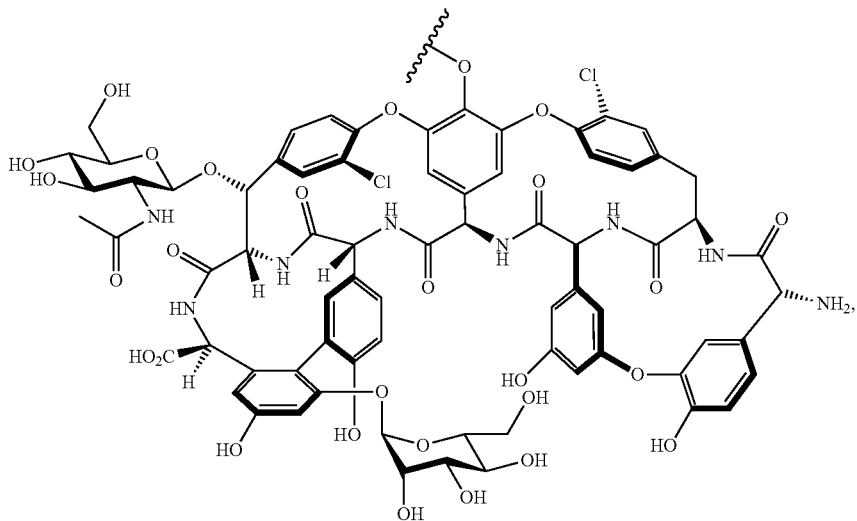

or a derivative thereof;

each instance of $R_{1p}$ and $R_{1c}$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or $-C(=O)R^C$;

each instance of $R^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or $-OR^O$;

each instance of $R^O$ is independently hydrogen, optionally substituted alkyl, or an oxygen protecting group;

each of $R^p$ and $R^q$ is independently hydrogen, optionally substituted $C_{1-6}$ alkyl, an optionally substituted carbohydrate, or an oxygen protecting group; and each of m1 and m2 is independently 0 or an integer of 1 to 15, inclusive.

In certain embodiments of the provided preparation methods, the acyl-donor is of Formula (iii) and the mixture further comprises free CoA.

In certain embodiments, the mixture has a pH of about 6 to about 10. In certain embodiments, the mixture has a pH of about 8 to about 10. In certain embodiments, the mixture has a pH of about 6 to about 8.

As used herein, the term "acyltransferase" refers to a type of transferase enzyme that catalyze the transfer of an acyl group from one substance to another. In certain embodiments, the acyltransferase is a long-chain-alcohol O-fatty-acyltransferase that catalyzes the chemical reaction:

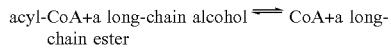

In certain embodiments, the acyltransferase is a long-chain-amino acyltransferase that catalyzes the chemical reaction:

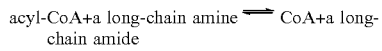

As used herein, long-chain alcohols (or named fatty alcohols) or long-chain amines (or named fatty amines) are usually high-molecular-weight aliphatic alcohols or high-molecular-weight aliphatic amines. In certain embodiments, the "long chain" refers to an aliphatic chain having over six carbons. In certain embodiments, the long chain has over eight carbons. In certain embodiments, the long chain has over ten carbons. In certain embodiments, the long chain has over twelve carbons. In certain embodiments, the long chain has over fourteen carbons. In certain embodiments, the long chain has over sixteen carbons.

In certain embodiments, the long-chain acyltransferase is N-acyl transferase. In certain embodiments, the long-chain acyltransferase is Orf11b or DBv8. In certain embodiments, the long-chain acyltransferase is Orf1 1b. In certain embodiments, the long-chain acyltransferase is DBv8.

As used herein, Orf11b or DBv8 includes both wide type and derivative proteins obtained from Orf11b or DBv8 genes. In certain embodiments, Orf11b or DBv8 encompasses mutants having amino acid sequences by substitution of one or more amino acids in the wide types for one or more different amino acids. The mutation can be conservative mutations or point mutations.

In certain embodiments, the acyltransferase includes one, two, three, four, or five point mutations. In certain embodiments, these point mutations may be conservative changes (e.g., mutation of a serine to a threonine). In certain embodiments, the acyltransferase includes one, two, three, four, five, or more additional amino acids. In certain embodiments, the acyltransferase has one, two, three, four, or five amino acids removed from the sequence. In certain embodiments, the resulting amino acid sequence is at least 90%, at least 95%, at least 97%, at least 98%, or at least 99% homologous or identical to the wild type sequence.

Also described herein are methods of using the natural teicoplanin mixtures and one or more acyl transferases, and optionally free CoA, as the substrates under catalysis of Orf11b or DBv8 to generate new single uniform teicoplanin analogs (e.g. 2-acylated teicoplanin analogs) or double acylated teicoplanin analogs (2-,6-diacylted teicoplanin analogs) in a one-step reaction. In certain embodiments, the provided methods use the natural teicoplanin mixtures and acyl-CoAs/acyl-NAC, and optionally free CoA, as the substrates under catalysis of Orf11b or DBv8 to generate new single uniform teicoplanin analogs (e.g. 2-acylated teicoplanin analogs) or double acylated teicoplanin analogs (2-,6-diacylted teicoplanin analogs) in a one-step reaction. In certain embodiments, the provided methods use the natural teicoplanin mixtures and acyl-CoAs, and optionally free CoA, as the substrates under catalysis of Orf11b or DBv8 to generate new single uniform teicoplanin analogs (e.g. 2-acylated teicoplanin analogs) or double acylated teicoplanin analogs (2-,6-diacylted teicoplanin analogs) in a one-step reaction. In certain embodiments, the provided methods use the natural teicoplanin mixtures and acyl-NAC, and optionally free CoA, as the substrates under catalysis of Orf11b or DBv8 to generate new single uniform teicoplanin analogs (e.g. 2-acylated teicoplanin analogs) or double acylated teicoplanin analogs (2-,6-diacylted teicoplanin analogs) in a one-step reaction. In certain embodiments, the provided method is carried out at a pH of about 6.0 to 8.0 to generate a mono-acylated teicoplanin analog (e.g. Compound 9). In certain embodiments, the provided method is carried out at a pH of about 8.0 to 10.0 (e.g. pH of 9.0) to generate a diacylated teicoplanin analog (e.g. Compound 11). The provided synthetic methods avoid the tedious preparation/purification of teicoplanin precursors such as teicoplanin aglycon or teicoplanin pseudoaglycone as shown in the art, for example, Kruger, R. G. et al. Tailoring of glycopeptide scaffolds by the acyltransferases from the teicoplanin and A-40,926 biosynthetic operons. Chem Biol 12, 131-140,doi: 10.1016/j.chembiol.2004.12.005 (2005); Kahne, D., Leimkuhler, C., Lu, W. & Walsh, C. Glycopeptide and lipoglycopeptide antibiotics. Chem Rev., 105, 425-448, doi: 10.1021/cr030103a (2005).

As generally defined herein, $R_{1p}$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or —C(=O)$R^C$, wherein $R^C$ is as defined herein. In certain embodiments, $R_{1p}$ is optionally substituted alkyl. In certain embodiments, $R_{1p}$ is optionally substituted $C_{1-15}$ alkyl. In certain embodiments, $R_{1p}$ is optionally substituted $C_{1-15}$ alkylaryl, substituted $C_{1-15}$ alkylalkynyl, or optionally substituted $C_{1-15}$ alkylhydroxyl. In certain embodiments, $R_{1p}$ is optionally substituted $C_{1-10}$ alkyl. In certain embodiments, $R_{1p}$ is optionally substituted $C_{1-6}$ alkyl. In certain embodiments, $R_{1p}$ is substituted alkyl. In certain embodiments, $R_{1p}$ is substituted $C_{1-15}$ alkyl. In certain embodiments, $R_{1p}$ is substituted $C_{1-10}$ alkyl. In certain embodiments, $R_{1p}$ is substituted $C_{1-6}$ alkyl. In certain embodiments, $R_{1p}$ is unsubstituted alkyl. In certain embodiments, $R_{1p}$ is unsubstituted $C_{1-15}$ alkyl. In certain embodiments, $R_{1p}$ is unsubstituted $C_{1-10}$ alkyl. In certain embodiments, $R_{1p}$ is unsubstituted $C_{1-6}$ alkyl.

In some embodiments, $R_{1p}$ is optionally substituted alkenyl. In some embodiments, $R_{1p}$ is optionally substituted $C_{2-15}$ alkenyl. In some embodiments, $R_{1p}$ is optionally substituted $C_{2-10}$ alkenyl. In some embodiments, $R_{1p}$ is substituted $C_{2-15}$ alkenyl. In some embodiments, $R_{1p}$ is substituted $C_{2-10}$ alkenyl. In some embodiments, $R_{1p}$ is unsubstituted $C_{2-15}$ alkenyl. In some embodiments, $R_{1p}$ is unsubstituted $C_{2-10}$ alkenyl.

In some embodiments, $R_{1p}$ is optionally substituted alkynyl. In some embodiments, $R_{1p}$ is optionally substituted $C_{2-15}$ alkynyl.

In some embodiments, $R_{1p}$ is optionally substituted $C_{2-10}$ alkynyl. In some embodiments, $R_{1p}$ is optionally substituted carbocyclyl, optionally substituted heterocyclyl, optionally substituted aryl, optionally substituted heteroaryl, or —C(=O)$R^C$. In some embodiments, $R_{1p}$ is optionally substituted $C_{3-6}$ carbocyclyl, optionally substituted 3- to 6-membered heterocyclyl, optionally substituted aryl, optionally substituted heteroaryl, or —C(=O)$R^C$. In some embodiments, $R_{1p}$ is optionally substituted carbocyclyl. In some embodiments, $R_{1p}$ is optionally substituted $C_{3-6}$ carbocyclyl. In some embodiments, $R_{1p}$ is optionally substituted heterocyclyl. In some embodiments, $R_{1p}$ is optionally substituted 3- to 6-membered heterocyclyl. In some embodiments, $R_{1p}$ is optionally substituted 6-membered heterocyclyl with one heteroatom selected from the group consisting of N, O, and S. In some embodiments, $R_{1p}$ is optionally substituted 6-membered heterocyclyl with two heteroatoms each independently selected from the group consisting of N, O, and S. In some embodiments, $R_{1p}$ is optionally substituted 6-membered heterocyclyl with three heteroatoms each independently selected from the group consisting of N, O, and S. In some embodiments, $R_{1p}$ is optionally substituted 5-membered heterocyclyl with one heteroatom selected from the group consisting of N, O, and S. In some embodiments, $R_{1p}$ is optionally substituted 5-membered heterocyclyl with two heteroatoms each independently selected from the group consisting of N, O, and S. In some embodiments, $R_{1p}$ is optionally substituted aryl. In some embodiments, $R_{1p}$ is optionally substituted phenyl. In some embodiments, $R_{1p}$ is phenyl. In some embodiments, $R_{1p}$ is optionally substituted heteroaryl. In some embodiments, $R_{1p}$ is optionally substituted 6-membered heteroaryl with one heteroatom selected from the group consisting of N, O, and S. In some embodiments, $R_{1p}$ is optionally substituted 6-membered heteroaryl with two heteroatoms each independently selected from the group consisting of N, O, and S. In some embodiments, $R_{1p}$ is optionally substituted 5-membered heteroaryl with one heteroatom selected from the group consisting of N, O, and S. In some embodiments, $R_{1p}$ is optionally substituted 5-membered heteroaryl with two heteroatoms each independently selected from the group consisting of N, O, and S.

In some embodiments, $R_{1p}$ is —C(=O)$R^C$, wherein each instance of $R^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or O$R^O$; wherein each instance of $R^O$ is independently hydrogen, optionally substituted alkyl, or an oxygen protecting group. In some embodiments, $R_{1p}$ is —C(=O)$R^C$, wherein $R^C$ is optionally substituted alkyl. In some embodiments, $R_{1p}$ is —C(=O)$R^C$, wherein $R^C$ is optionally substituted $C_{1-15}$ alkyl. In some embodiments, $R_{1p}$ is —C(=O)$R^C$, wherein $R^C$ is optionally substituted $C_{1-10}$ alkyl. In some embodiments, $R_{1p}$ is —C(=O)$R^C$, wherein $R^C$ is optionally substituted $C_{1-6}$ alkyl. In some embodiments, $R_{1p}$ is —C(=O)$R^C$, wherein $R^C$ is methyl, ethyl, n-propyl, or iso-propyl. In some embodiments, $R_{1p}$ is —C(=O)$R^C$, wherein $R^C$ is O$R^O$; and $R^O$ is independently hydrogen, optionally substituted alkyl, or an oxygen protecting group. In some embodiments, $R_{1p}$ is —C(=O)$R^C$, wherein $R^C$ is OH. In some embodiments, $R_{1p}$ is —C(=O)$R^C$, wherein $R^C$ is O$R^O$; and $R^O$ is optionally substituted alkyl. In some embodiments, $R_{1p}$ is —C(=O)$R^C$, wherein $R^C$ is O$R^O$; and $R^O$ is optionally substituted $C_{1-15}$ alkyl. In some embodiments, $R_{1p}$ is —C(=O)$R^C$, wherein $R^C$ is O$R^O$; and $R^O$ is optionally substituted $C_{1-10}$ alkyl. In some embodiments, $R_{1p}$ is —C(=O)$R^C$, wherein $R^C$ is O$R^O$; and $R^O$ is optionally substituted $C_{1-6}$ alkyl. In some embodiments, $R_{1p}$ is —C(=O)$R^C$, wherein $R^C$ is O$R^O$; and $R^O$ is methyl, ethyl, n-propyl, or iso-propyl. In some embodiments, $R_{1p}$ is —C(=O)$R^C$, wherein $R^C$ is O$R^O$; and $R^O$ is an oxygen protecting group.

In some embodiments, $R_{1p}$ is of one of the following formulae:

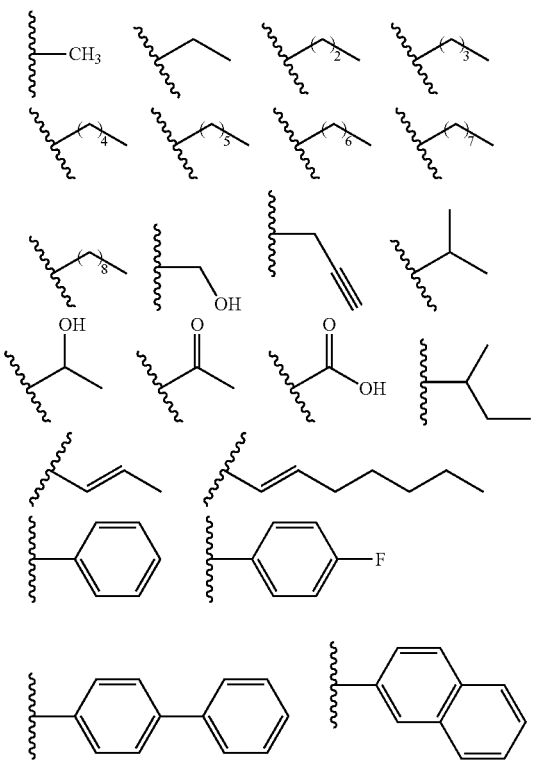

As generally defined herein, $R_{1c}$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or —C(=O)R$^C$, wherein R$^C$ is as defined herein. In certain embodiments, $R_{1c}$ is optionally substituted alkyl. In certain embodiments, $R_{1c}$ is optionally substituted $C_{1-15}$ alkyl.

In certain embodiments, $R_{1c}$ is optionally substituted $C_{1-15}$ alkylaryl, substituted $C_{1-15}$ alkylalkynyl, or optionally substituted $C_{1-15}$ alkylhydroxyl. In certain embodiments, $R_{1c}$ is optionally substituted $C_{1-10}$ alkyl. In certain embodiments, $R_{1c}$ is optionally substituted $C_{1-6}$ alkyl. In certain embodiments, $R_{1c}$ is substituted alkyl. In certain embodiments, $R_{1c}$ is substituted $C_{1-15}$ alkyl. In certain embodiments, $R_{1c}$ is substituted $C_{1-10}$ alkyl. In certain embodiments, $R_{1c}$ is substituted $C_{1-6}$ alkyl. In certain embodiments, $R_{1c}$ is unsubstituted alkyl. In certain embodiments, $R_{1c}$ is unsubstituted $C_{1-15}$ alkyl. In certain embodiments, $R_{1c}$ is unsubstituted $C_{1-10}$ alkyl. In certain embodiments, $R_{1c}$ is unsubstituted $C_{1-6}$ alkyl.

In some embodiments, $R_{1c}$ is optionally substituted alkenyl. In some embodiments, $R_{1c}$ is optionally substituted $C_{2-15}$ alkenyl. In some embodiments, $R_{1c}$ is optionally substituted $C_{2-10}$ alkenyl. In some embodiments, $R_{1c}$ is substituted $C_{2-15}$ alkenyl. In some embodiments, $R_{1c}$ is substituted $C_{2-10}$ alkenyl. In some embodiments, $R_{1c}$ is unsubstituted $C_{2-15}$ alkenyl. In some embodiments, $R_{1c}$ is unsubstituted $C_{2-10}$ alkenyl.

In some embodiments, $R_{1c}$ is optionally substituted alkynyl. In some embodiments, $R_{1c}$ is optionally substituted $C_{2-15}$ alkynyl. In some embodiments, $R_{1c}$ is optionally substituted $C_{2-10}$ alkynyl.

In some embodiments, $R_{1c}$ is optionally substituted carbocyclyl, optionally substituted heterocyclyl, optionally substituted aryl, optionally substituted heteroaryl, or —C(=O)R$^C$. In some embodiments, $R_{1c}$ is optionally substituted $C_{3-6}$ carbocyclyl, optionally substituted 3- to 6-membered heterocyclyl, optionally substituted aryl, optionally substituted heteroaryl, or —C(=O)R$^C$. In some embodiments, $R_{1c}$ is optionally substituted carbocyclyl. In some embodiments, $R_{1c}$ is optionally substituted $C_{3-6}$ carbocyclyl. In some embodiments, $R_{1c}$ is optionally substituted heterocyclyl. In some embodiments, $R_{1c}$ is optionally substituted 3- to 6-membered heterocyclyl. In some embodiments, $R_{1c}$ is optionally substituted 6-membered heterocyclyl with one heteroatom selected from the group consisting of N, O, and S. In some embodiments, $R_{1c}$ is optionally substituted 6-membered heterocyclyl with two heteroatoms each independently selected from the group consisting of N, O, and S. In some embodiments, $R_{1c}$ is optionally substituted 6-membered heterocyclyl with three heteroatoms each independently selected from the group consisting of N, O, and S. In some embodiments, $R_{1c}$ is optionally substituted 5-membered heterocyclyl with one heteroatom selected from the group consisting of N, O, and S. In some embodiments, $R_{1c}$ is optionally substituted 5-membered heterocyclyl with two heteroatoms each independently selected from the group consisting of N, O, and S. In some embodiments, $R_{1c}$ is optionally substituted aryl. In some embodiments, $R_{1c}$ is optionally substituted phenyl. In some embodiments, $R_{1c}$ is phenyl. In some embodiments, $R_{1c}$ is optionally substituted heteroaryl. In some embodiments, $R_{1c}$ is optionally substituted 6-membered heteroaryl with one heteroatom selected from the group consisting of N, O, and S. In some embodiments, $R_{1c}$ is optionally substituted 6-membered heteroaryl with two heteroatoms each independently selected from the group consisting of N, O, and S. In some embodiments, $R_{1c}$ is optionally substituted 5-membered heteroaryl with one heteroatom selected from the group consisting of N, O, and S. In some embodiments, $R_{1c}$ is optionally substituted 5-membered heteroaryl with two heteroatoms each independently selected from the group consisting of N, O, and S.

In some embodiments, $R_{1c}$ is —C(=O)R$^C$, wherein each instance of R$^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or OR$^O$; wherein each instance of R$^O$ is independently hydrogen, optionally substituted alkyl, or an oxygen protecting group. In some embodiments, $R_{1c}$ is —C(=O)R$^C$, wherein R$^C$ is optionally substituted alkyl. In some embodiments, $R_{1c}$ is —C(=O)R$^C$, wherein R$^C$ is optionally substituted $C_{1-15}$ alkyl. In some embodiments, $R_{1c}$ is —C(=O)R$^C$, wherein R$^C$ is optionally substituted $C_{1-10}$ alkyl. In some embodiments, $R_{1c}$ is —C(=O)R$^C$, wherein R$^C$ is optionally substituted $C_{1-6}$ alkyl. In some embodiments, $R_{1c}$ is —C(=O)R$^C$, wherein R$^C$ is methyl, ethyl, n-propyl, or iso-propyl. In some embodiments, $R_{1c}$ is —C(=O)R$^C$, wherein R$^C$ is OR$^O$; and R$^O$ is independently hydrogen, optionally substituted alkyl, or an oxygen protecting group. In some embodiments, $R_{1c}$ is —C(=O)R$^C$, wherein R$^C$ is OH. In some embodiments, $R_{1c}$ is —C(=O)R$^C$, wherein R$^C$ is OR$^O$; and R$^O$ is optionally substituted alkyl. In some embodiments, $R_{1c}$ is —C(=O)R$^C$, wherein R$^C$ is OR$^O$; and R$^O$ is optionally substituted $C_{1-15}$ alkyl. In some embodiments, $R_{1c}$ is —C(=O)R$^C$, wherein R$^C$ is OR$^O$; and R$^O$ is optionally substituted $C_{1-10}$ alkyl. In some embodiments, $R_{1c}$ is —C(=O)R$^C$, wherein R$^C$ is OR$^O$; and R$^O$ is optionally substituted $C_{1-6}$ alkyl. In some embodiments, $R_{1c}$ is —C(=O)R$^C$, wherein R$^C$ is OR$^O$; and R$^O$ is methyl, ethyl, n-propyl, or iso-propyl. In some embodiments, $R_{1c}$ is —C(=O)$R^C$, wherein $R^C$ is O$R^O$; and $R^O$ is an oxygen protecting group.

In some embodiments, $R_{1c}$ is of one of the following formulae:

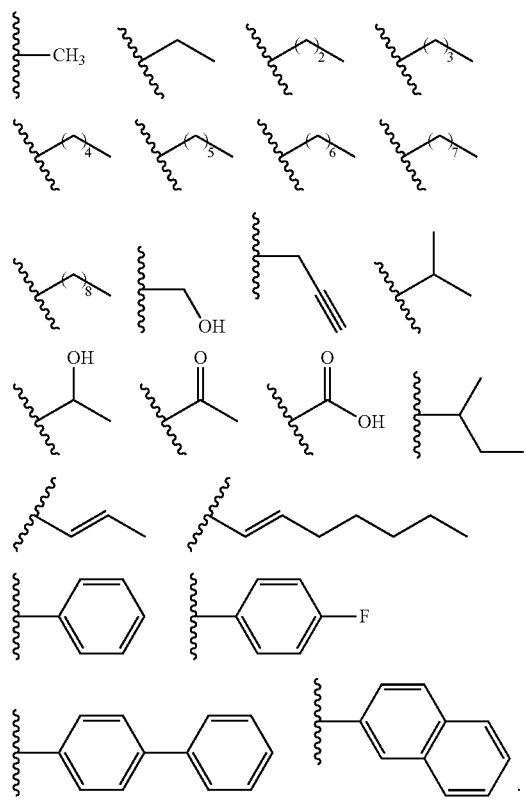

As generally defined herein, m1 is 0 or an integer of 1 to 15, inclusive. In certain embodiments, m1 is 0. In certain embodiments, m1 is an integer of 1 to 15, inclusive. In certain embodiments, m1 is an integer of 5 to 15, inclusive. In certain embodiments, m1 is an integer of 5 to 10, inclusive. In certain embodiments, m1 is an integer of 10 to 15, inclusive. In certain embodiments, m1 is an integer of 1 to 10, inclusive. In certain embodiments, m1 is an integer of 1 to 5, inclusive.

As generally defined herein, m2 is 0 or an integer of 1 to 15, inclusive. In certain embodiments, m2 is 0. In certain embodiments, m2 is an integer of 1 to 15, inclusive. In certain embodiments, m2 is an integer of 5 to 15, inclusive. In certain embodiments, m2 is an integer of 5 to 10, inclusive. In certain embodiments, m2 is an integer of 10 to 15, inclusive. In certain embodiments, m2 is an integer of 1 to 10, inclusive. In certain embodiments, m2 is an integer of 1 to 5, inclusive.

In certain embodiments,

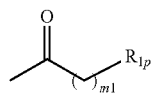

is of one of the following formulae:

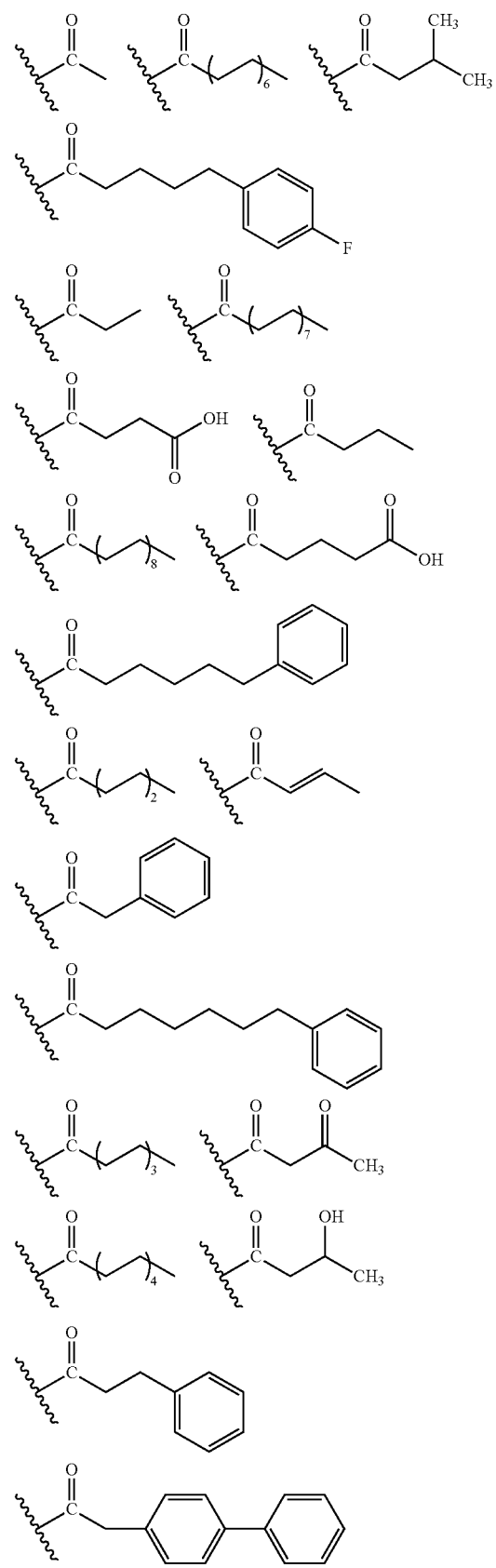

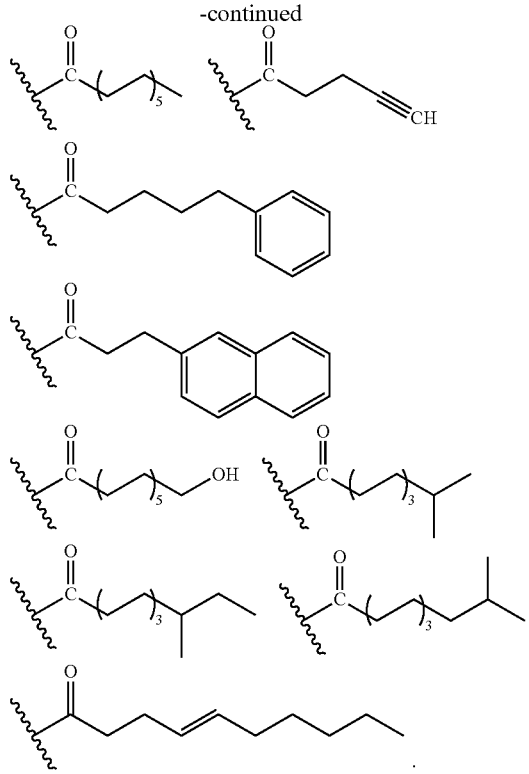
In certain embodiments,
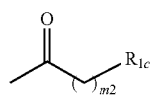
is of one of the following formulae:
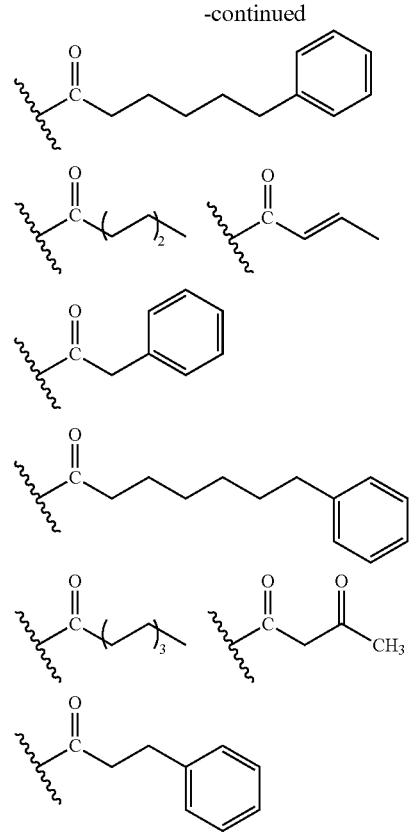
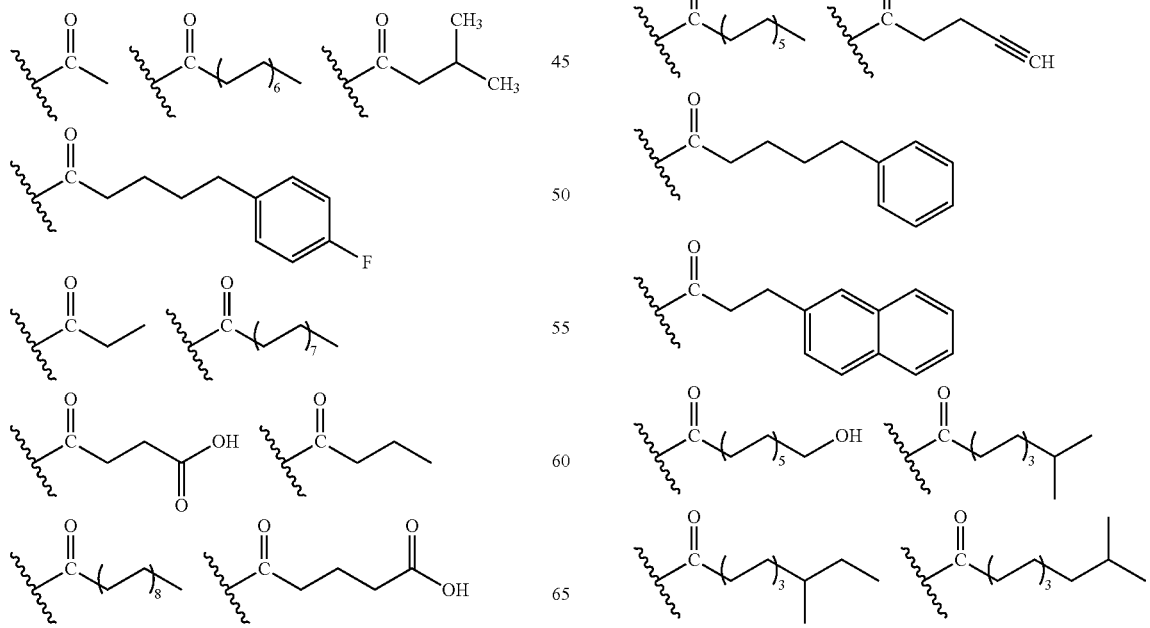

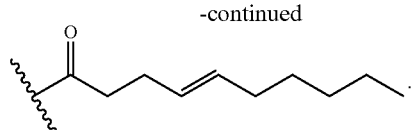

As used herein, CoA refers to coenzyme A (CoA, CoASH, or HSCoA), a coenzyme, notable for its role in the synthesis and oxidation of fatty acids, and the oxidation of pyruvate in the citric acid cycle. The structure of free CoA is as follows:

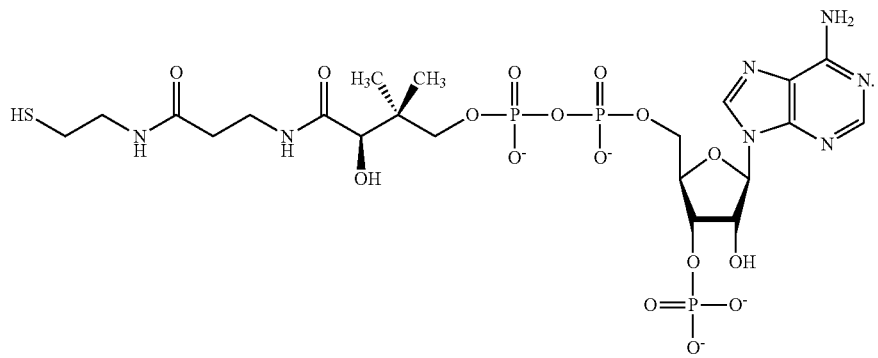

When CoA is attached to an acyl group, the point of attachment on CoA is at the thiol group. In certain embodiments, the acyl-donor of Formula (S-i) is of Formula (S-i-a)

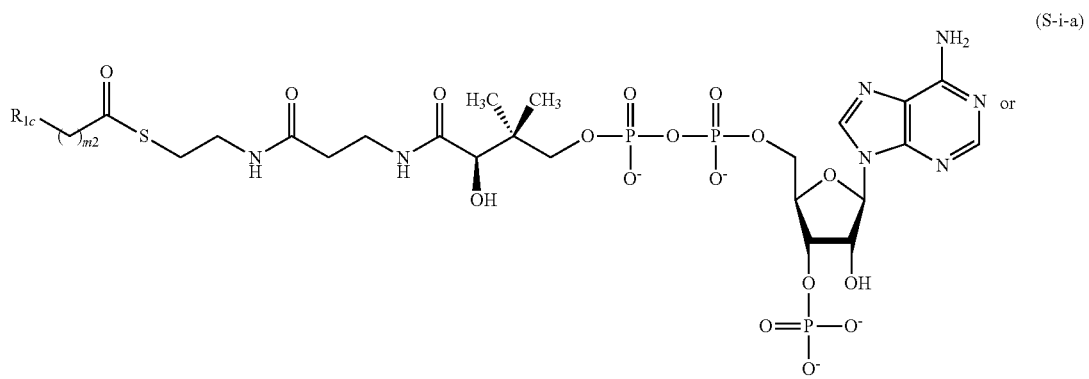

derivative thereof.

As used herein, NAC refers to acetylcysteamine (also known as N-acetylcysteamine). When NAC is attached to an acyl group, the point of attachment on NAC is at the thiol group. In certain embodiments, the acyl-donor of Formula (S-ii) is of the Formula (S-ii-a)

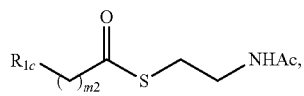

(S-ii-a)

wherein m2 is as defined herein.

In certain embodiments, the provided method generates a teicoplanin analog is of Formula (I):

(I)

$$\text{[structure shown]}$$

or a pharmaceutically acceptable salt thereof, wherein

X is of Formula (i):

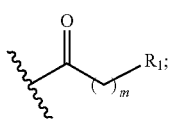

Y is hydrogen or of Formula (ii):

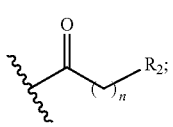

and

Z is of Formula (iii):

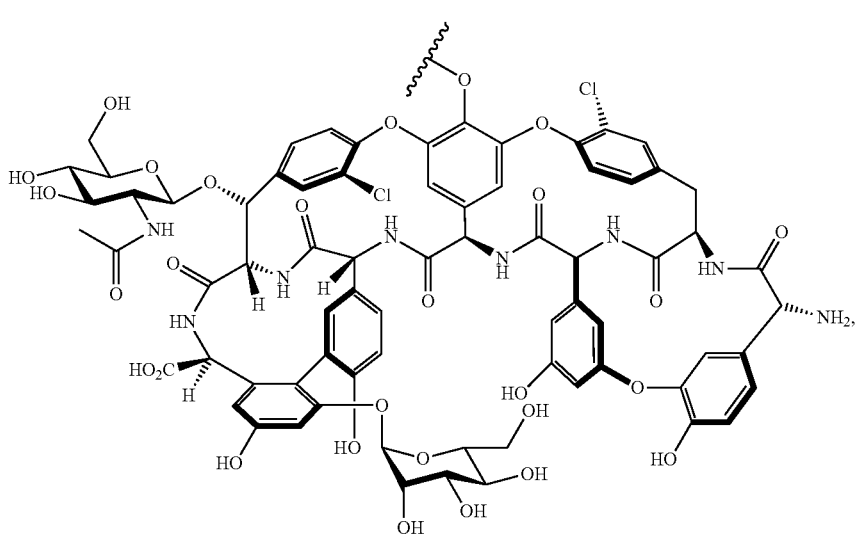

or a derivative thereof;

each instance of $R_1$ and $R_2$ is, independently, optionally substituted alkyl, optionally substituted alkenyl, optionally substituted alkynyl, optionally substituted carbocyclyl, optionally substituted heterocyclyl, optionally substituted aryl, optionally substituted heteroaryl, or —C(=O)$R^C$;

each instance of $R^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or —O$R^O$;

each instance of $R^O$ is independently hydrogen, optionally substituted alkyl, or an oxygen protecting group;

each of $R^p$ and $R^q$ is independently hydrogen, optionally substituted $C_{1-6}$ alkyl, an optionally substituted carbohydrate, or an oxygen protecting group;

m is 0 or an integer of 1 to 15, inclusive; and n is 0 or an integer of 1 to 15, inclusive.

In certain embodiments, the provided method generates a teicoplanin analog of Formula (I-a):

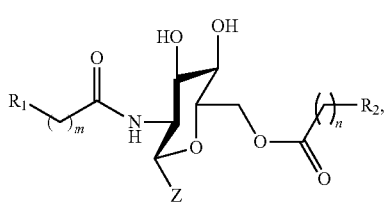

wherein $R_1$, $R_2$, m, and Z are as defined herein.

In certain embodiments, the provided method generates a teicoplanin analog of Formula (I-b):

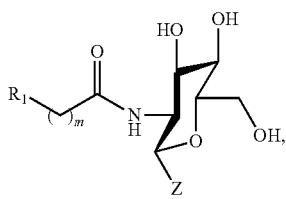

wherein R1, R2, m, and Z are as defined herein.

In certain embodiments, the provided method generates a teicoplanin analog of Formula (I) wherein Y is hydrogen and X is one of the following formulae:

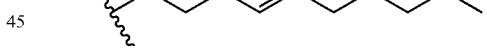

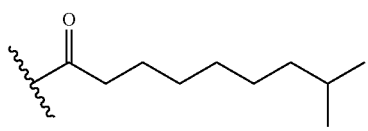

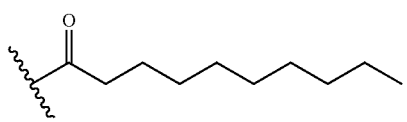

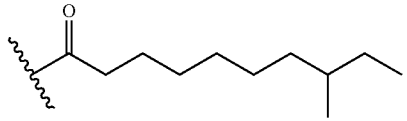

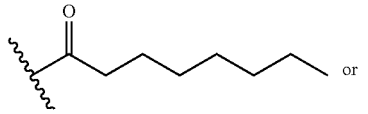 or

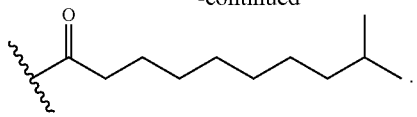

In certain embodiments, the provided method generates a teicoplanin analog of any one of compounds listed in Table A1.

As used herein, the term "alkyl" refers to a straight-chained or branched alkyl group containing 1 to 6 carbon atoms. Examples of alkyl groups include methyl, ethyl, n-propyl, isopropyl, tert-butyl, and n-pentyl. Similarly, the term "alkenyl" or "alkynyl" refers to a straight-chained or branched alkenyl or alkynyl group containing 2 to 6 carbon atoms. The term "alkyloxyl" refers to an —O-alkyl radical.

The term "aryl" refers to a hydrocarbon ring system (mono-cyclic or bi-cyclic) having at least one aromatic ring. Examples of aryl moieties include, but are not limited to, phenyl, naphthyl, and pyrenyl.

The term "heteroaryl" refers to a hydrocarbon ring system (mono-cyclic or bi-cyclic) having at least one aromatic ring which contains at least one heteroatom such as O, N, or S as part of the ring system and the reminder being carbon. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl.

The terms "cyclyl" and "heterocyclyl" refer to a partially or fully saturated mono-cyclic or bi-cyclic ring system having from 4 to 14 ring atoms. A heterocyclyl ring contains one or more heteroatoms (e.g., O, N, or S) as part of the ring system and the remainder being carbon. Exemplary cyclyl and heterocyclyl rings are cyclohexane, piperidine, piperazine, morpholine, thiomorpholine, and 1,4-oxazepane.

Unless specifically pointed out, alkyl, alkenyl, alkynyl, aryl, heteroaryl, cyclyl, and heterocyclyl mentioned herein include both substituted and unsubstituted moieties. The term "substituted" refers to one or more substituents (which may be the same or different), each replacing a hydrogen atom. Examples of substituents include, but are not limited to, halogen, cyano, nitro, hydroxyl, amino, mercapto, alkyl, alkenyl, alkynyl, aryl, heteroaryl, cyclyl, heterocyclyl, alkyloxy, aryloxy, alksulfanyl, arylsulfanyl, alkylamino, arylamino, dialkylamino, diarylamino, alkylcarbonyl, arylcarbonyl, heteroarylcarbonyl, alkylcarboxyl, arylcarboxyl, heteroarylcarboxyl, alkyloxycarbonyl, aryloxycarbonyl, heteroaryloxycarbonyl, alkylcarbamido, arylcarbamido, heterocarbamido, alkylcarbamyl, arylcarbamyl, heterocarbamyl, wherein each of alkyl (including alk), alkenyl, aryl, heteroaryl, cyclyl, and heterocyclyl is optionally substituted with halogen, cyano, nitro, hydroxyl, amino, mercapto, alkyl, aryl, heteroaryl, alkyloxy, aryloxy, alkylcarbonyl, arylcarbonyl, alkylcarboxyl, arylcarboxyl, alkyloxycarbonyl, or aryloxycarbonyl.

Another aspect of the present invention relates to a pharmaceutical composition that contains a pharmaceutically acceptable carrier and an effective amount of at least one of the provided compounds described above.

In another aspect, the present invention provides methods for inhibiting bacterial growth and/or microbial infection s comprising administering to a subject a therapeutically effective amount of a compound of Formula (I), or a pharmaceutical acceptable salt thereof.

In another aspect, the present invention provides methods for treating a bacterial infection comprising administering to a subject a therapeutically effective amount of a compound of Formula (I), or a pharmaceutical acceptable salt thereof.

In certain embodiments, the bacterium is a gram-positive bacterium. In certain embodiments, the bacterium is at least one selected from the group consisting of Staphylococcus sp., Enterococcus sp., Escherichia coli, Bacillus sp., Salmonella sp., and Mycobacterium sp. In certain embodiments, the bacterium is methicillin-resistant Staphylococcus Aureus (MRSA), methicillin-resistant Staphylococcus Epidermidis (MRSE), penicillin-resistant Streptococcus pneumonia, quinolone-resistant Staphylococcus Aureus (QRSA), vancomycin-resistant Staphylococcus Aureus (VRSA), vancomycin-resistant Enterococci (VRE), or multi-drug resistant Mycobacterium tuberculosis.

All of the provided compounds described above include the compounds themselves, as well as their salts and their prodrugs, if applicable. The salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the compounds described above (see Goodman and Gilman's, The Pharmacological basis of Therapeutics, 8$^{th}$ ed., McGraw-Hill, Int. Ed. 1992, "Biotransformation of Drugs").

Also within the scope of this invention are a composition containing one or more of the provided compounds described above for use in treating diseases or disorders described above, and the use of such a composition for the manufacture of a medicament for use in the aforementioned treatment Other features or advantages of the present invention will be apparent from the following detailed description of several embodiments, and also from the appended claims.

BRIEF DESCRIPTION OF THE DRAWINGS

FIG. 2 shows structures of Orf11* and Dbv8. (a) The apo structure of Orf11* is shown in the left panel. For the all-helix domain, this domain consists of eight α-helices (α1-α8). For the GNAT domain, this domain is composed of a five-stranded β-sheet (β1-β5) and five α-helices (α9-α13) (right panel). (b) Orf11* and Dbv8 were superimposed with the rmsd of 1.093 Å for 310 Cα. (c) The binary structure of Orf11* in complex with decanoyl-CoA, which is bound at the GNAT domain. (d) View of the lipid tunnel in Orf11*. (e) The unary and binary structures of Orf11 were superimposed with the rmsd of 1.25 Å for 310 Cα, which suggests that the GNAT domain undergoes a conformational change upon binding of acyl-CoA resulting in 10 Å displacement or 15° rotation. (f) The loop β3-α9 in the GNAT domain undergoes 180° inside-out twist when acyl-CoA enters in the binding site. This wavering connects two salt bridges E199:R284 (2.8 Å) and K153:E280 (2.9 Å). (g) The ternary structure of Orf11* in complex with Tei pseudoaglycon 3 and decanoyl-CoA 4, in which Tei pseudoaglycon 3 is located at the junction of the all-helix and GNAT domains. (h) Superposition of uinary, binary and ternary structures of Orf11*.

FIG. 7 shows structural alignment of Orf11* and its N-terminal domain. This structural alignment was performed using the DALI server. The overall structure of Orf11* belongs to the protein family of acetyltransferases. The N-terminal all-helix domain belongs to the protein family of AAA atpases. Z score: the statistical significance of the similarity between protein-of-interest and other neighborhood proteins. RMSD: the root-mean-square deviation of C-alpha atoms in the least-squares superimposition of the structurally equivalent C-alpha atoms. Lali: the number of structurally equivalent residues. Nres: the total number of amino acids in the hit protein. % id: the percentage of identical amino acids over structurally equivalent residues.

FIG. 19 shows Table 1: data collection, phasing and refinement statistics for structures of Dbv8, Orf11* and mutants thereof. Highest resolution shell is shown in parenthesis.

FIG. 20 shows Table 2: structures of acyl-CoAs and their availability in enzymatic reactions. The enzymatic activities were determined by LC/MS. "+" represents the given acyl-CoA can be utilized by Orf11* to generate corresponding acyl Tei derivatives. Malonyl-, isobutyryl-, methylmalonyl- and benzoyl-CoA cannot be utilized by Orf11* due to steric hindrance. Major LC traces and mass spectra for positive reactions are shown in FIG. 18.

FIG. 21 shows Table 3: relative enzymatic activities of mutants and proposed functions for the selected residues. a. The activities of mutants were determined by HPLC. The reaction rates were calculated using the linear regression equation on the basis of averaged peak areas in triplicate. The relative activities were determined by dividing individual reaction rates with that of WT, where the relative activity of WT is 100%.

DETAILED DESCRIPTION

Figure 1:
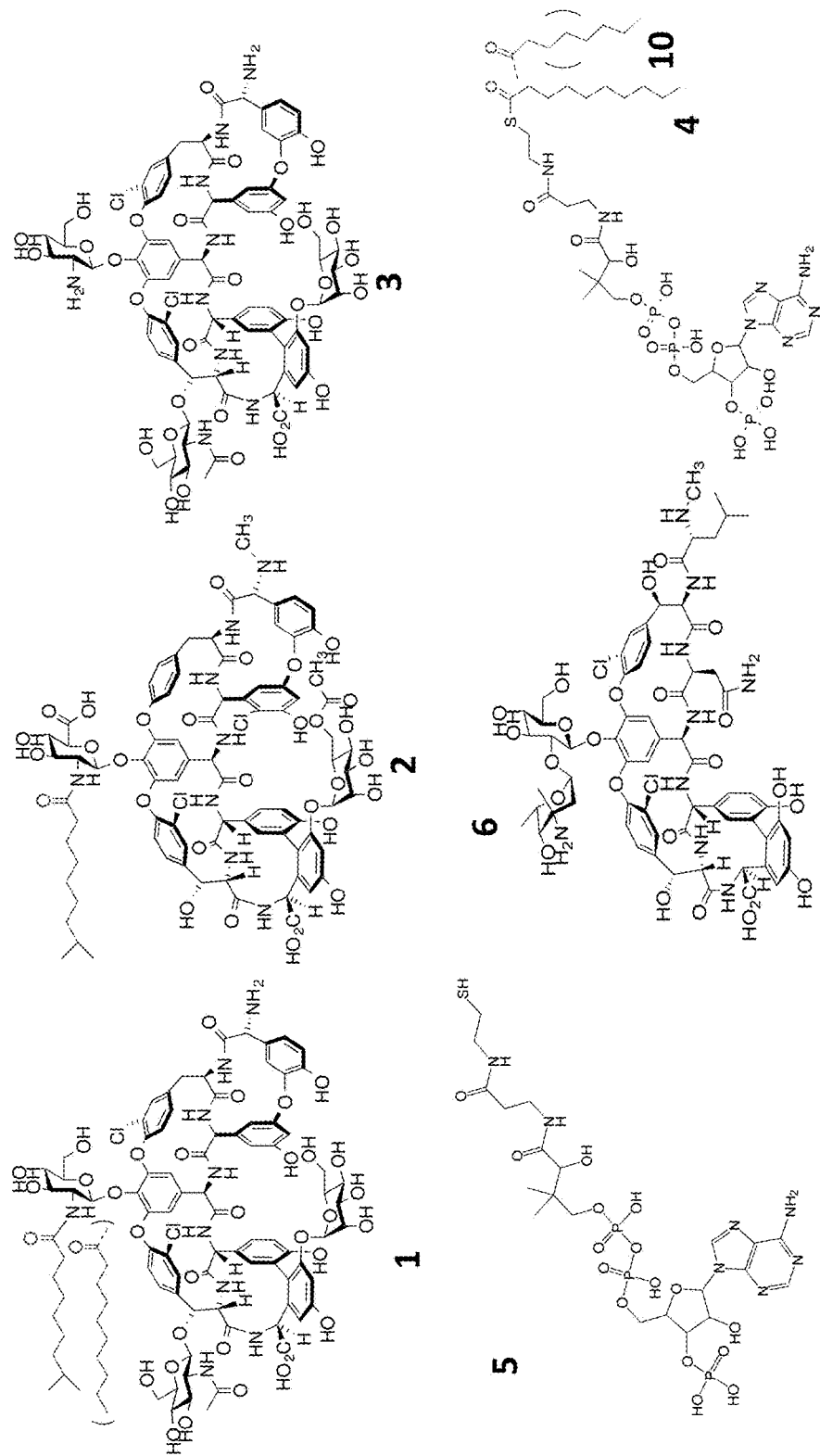
FIG. 1 shows chemical structures of glycopeptides and coenzyme A derivatives. Compound 1: teicoplanin A2-2 (brached chain) and A2-3 (straight chain) (referred to here as teicoplanin, Tei), compound 2: A40926, compound 3: Tei pseudoaglycone, compound 4: decanoly-CoA, compound 5: coenzyme A (CoA), compound 6: vancomycin (Van), compound 7: octyl-derivatiezed Van ($C_8$-Van), compound 8: decanoyl-N-acetyl cysteamine (decanoyl-NAC), compound 9: octyl-substituted Tei, compound 10: octyl-CoA, compound 11: diacyl-teicoplanin ($C_8,C_{10}$-Tei), compound 12: CoA-disulfide, compound 17: β-octyl glucoside (β-OG), octyl-CoA, compound 19: diacyl-Tei ($C_{10},C_{10}$-Tei).
Figure 1:
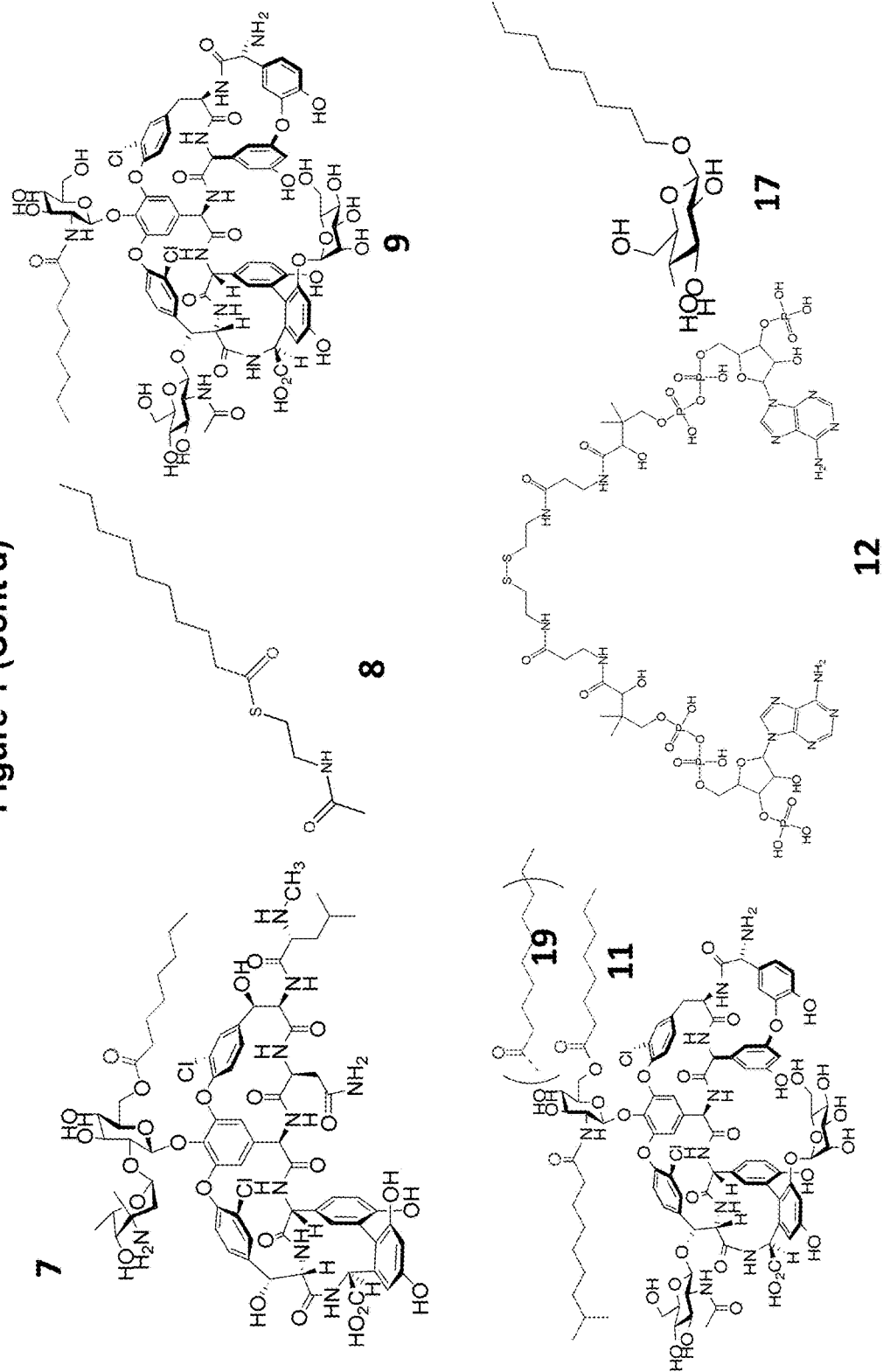

The present invention provides pharmaceutical compositions comprising a compound described herein, e.g., a compound of Formulae (I), or a pharmaceutically acceptable salt thereof. The present invention also provides pharmaceutical compositions for use in treating a bacterial infection comprising a compound described herein, e.g., a compound of Formulae (I), and pharmaceutically acceptable salts, solvates, hydrates, polymorphs, co-crystals, tautomers, stereoisomers, isotopically labeled derivatives, and prodrugs thereof, and optionally a pharmaceutically acceptable excipient. In certain embodiments, a provided composition comprises two or more compounds described herein.

In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting bacterial growth. In certain embodiments, the effective amount is an amount effective for treating or preventing microbial infection.

In certain embodiments, the bacterium is a gram-positive bacterium. In certain embodiments, the bacterium is at least one selected from the group consisting of *Staphylococcus* sp., *Enterococcus* sp., *Escherichia coli*, *Bacillus* sp., *Salmonella* sp., and *Mycobacterium* sp. In certain embodiments the bacterium is at least one selected from the group consisting of methicillin-resistant *Staphylococcus Aureus* (MRSA), methicillin-resistant *Staphylococcus Epidermidis* (MRSE), penicillin-resistant *Streptococcus pneumonia*, quinolone-resistant *Staphylococcus Aureus* (QRSA), vancomycin-resistant *Staphylococcus Aureus* (VRSA), vancomycin-resistant *Enterococci* (VRE), or multi-drug resistant *Mycobacterium tuberculosis*.

I. Compounds and Uses Thereof in Treating Bacterial Infections

The present invention provides compounds and pharmaceutical compositions useful for inhibiting bacterial growth. In one aspect, the present invention provides methods for inhibiting bacterial growth comprising administering an effective amount of a compound described herein (e.g., a compound of Formula (I)), a pharmaceutically acceptable salt thereof), a solvate, a hydrate, a polymorph, a co-crystal, a tautomer, a stereoisomer, an isotopically labeled derivative, or a prodrug thereof, as described herein, and optionally a pharmaceutically acceptable excipient to a subject in need of treatment. In another aspect, the present invention provides methods for treating or preventing microbial infection comprising administering an effective amount of a compound described herein (e.g., a compound of Formula (I)), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from at least one bacterial infection.

In yet another aspect, provided is a method of treating or preventing microbial infection caused by pathogen that are resistant to other treatments, for example, multi-drug tolerant or resistant and/or that neither grow nor die in the presence of or as a result of other treatments. Such a method can be conducted in vivo (i.e., by administration to a subject) or in vitro (e.g., upon contact with bacteria in a cell culture). For example, in certain embodiments, provided is a method of treating and/or preventing microbial infection comprising administering an effective amount of a compound of the present invention, e.g., a compound of Formula (I) or a pharmaceutically acceptable salt thereof, to a subject with a microbial infection.

For example, in certain embodiments, provided is a method of treating microbial infection comprising contacting an effective amount of the compound of the present invention with a microorganism. In certain embodiments, provided is an in vitro method of treating microbial infection comprising contacting an effective amount of the compound of the present invention with a microorganism in a cell culture. In certain embodiments, provided is an in vivo method of treating microbial infection comprising administering an effective amount of the compound of the present invention to a subject with a microbial infection. In certain embodiments, the microorganism is a bacterium.

Exemplary bacterial infections include, but are not limited to, infections with a gram positive bacteria (e.g., of the phylum Actinobacteria, phylum Firmicutes, or phylum Tenericutes); gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a gram positive bacteria. In certain embodiments, the gram positive bacteria is a bacteria of the phylum Firmicutes. In certain embodiments, the bacteria is a member of the phylum Firmicutes and the genus *Enterococcus*, i.e., the bacterial infection is an *Enterococcus* infection. Exemplary *Enterococci* bacteria include, but are not limited to, *E. avium, E. durans, E. faecalis, E. faecium, E. gallinarum, E. solitarius, E. casseliflavus*, and *E. raffinosus*. In certain embodiments, the *Enterococcus* infection is an *E. faecalis* infection. In certain embodiments, the *Enterococcus* infection is an *E. faecium* infection.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is an *S. aureus* infection. In certain embodiments, the *Staphylococcus* infection is an *S. epidermis* infection.

In certain embodiments, the bacterial infection is resistant to other antibiotic therapy. For example, in certain embodiments, the bacterial infection is vancomycin resistant (VR). In certain embodiments, the bacterial infection is a vancomycin-resistant *E. faecalis* infection. In certain embodiments, the bacterial infection is a vancomycin-resistant *E. faecium* infection. In certain embodiments, the bacterial infection is a methicillin-resistant (MR). In certain embodiments, the bacterial infection is a methicillin-resistant *S. aureus* (MRSA) infection.

In another aspect, the present invention provides a method for producing an antibacterial effect in a subject comprising administering an effective amount of a compound described herein or a pharmaceutically-acceptable salt thereof. In another aspect, the invention provides a method for inhibition of PGT in subject comprising administering to the subject an effective amount of a compound of Formula (I) or a pharmaceutically acceptable salt thereof as defined hereinbefore.

In yet another aspect, provided is a method of treating a bacterial infection and/or virulence including the treatment of bacteria or infection caused by bacteria that are resistant to other treatments, are multi-drug tolerant or resistant and/or that neither grow nor die in the presence of or as a result of other treatments. Such a method can be conducted in vivo (i.e., by administration to a subject) or in vitro (e.g., upon contact with bacteria in a cell culture). For example, in certain embodiments, provided is a method of treating bacterial virulence comprising administering an effective amount of a compound of the present invention e.g., a compound of Formula (I), or a pharmaceutically acceptable salt thereof, to a subject with a bacterial infection. In certain embodiments, the compound blocks virulence factor production.

In another aspect, the compounds of the present invention inhibit the growth of or kill rapidly dividing cells such as stimulated inflammatory cells. Thus, the present invention also contemplates the treatment of a disease, disorder, or condition associated with abnormal cellular proliferation, such as cancer, autoimmune diseases, inflammatory diseases, and diabetic retinopathy.

Thus, in one aspect, provided is a method of treating cancer comprising administering an effective amount of the compound of the present invention or pharmaceutically acceptable salt thereof to a subject.

In another aspect, provided is a method of treating an autoimmune disease comprising administering an effective amount of the compound of the present invention or pharmaceutically acceptable salt thereof to a subject.

In yet another aspect, provided is a method of treating an inflammatory disease comprising administering the compound of the present invention or pharmaceutically acceptable salt thereof to a subject.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. An indole compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the indole compounds, or one or more solubilizing agents, can be utilized as pharmaceutical excipients for delivery of the compounds described herein. Examples of other carriers include colloidal silicon dioxide, magnesium stearate, cellulose, sodium lauryl sulfate, and D&C Yellow #10. See, e.g., Remington's Pharmaceutical Sciences, Edition 16, Mack Publishing Co., Easton, Pa. (1980); and Goodman and Gilman's "The Pharmacological Basis of Therapeutics", Tenth Edition, Gilman, J. Hardman and L. Limbird, eds., McGraw-Hill Press, 155-173, 2001.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, quinupristin/dalfoprisin (Syndercid™), In certain embodiments, the antibiotic is a ribosome-targeting antibiotic.

Antibiotics target ribosomes at distinct locations within functionally relevant sites. They exert their inhibitory action by diverse modes, including competing with substrate binding, interfering with ribosomal dynamics, minimizing ribosomal mobility, facilitating miscoding, hampering the progression of the mRNA chain, and blocking the nascent protein exit tunnel. Examples of antibiotics that reveal novel ribosomal properties or enforced otherwise observed findings include the following: decoding (paromomycin); mRNA progression (spectinomycin); A-site binding to the small (tetracycline antibiotic) and the large (chloramphenicol) subunits; PTC mobility (sparsomycin); tRNA rotatory motion (quinupristin/dalfoprisin), and tunnel gating (troleandomycin); see Yonath, *Annu. Rev. Biochem.* (2005) 74:649-679.

Methods for Preparing the Compounds Described Herein

Figure 25:
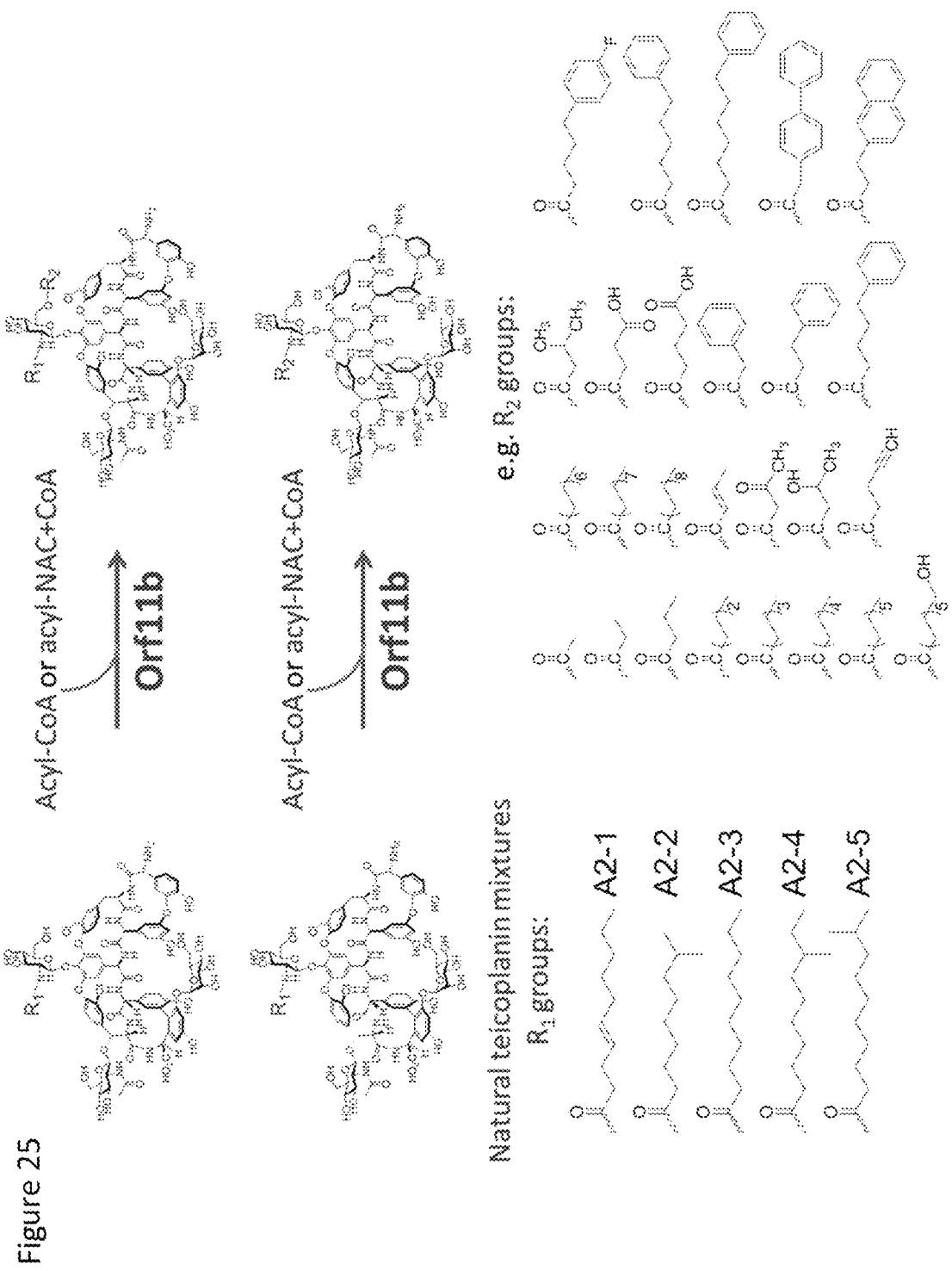
FIG. 25 shows exemplified reactions catalyzed by Orf11 to provide Tei analogs. Reaction 1 conditions: the reaction mixture (total volume 500 µl), containing Orf11b (final conc. 0.01 mM), teicoplanin (final conc. 2 mM) and acyl-CoA (final conc. 1 mM) or acyl-NAC (final conc. 2.5 mM)+CoA (final conc. 1 mM) in a Tris buffer solution (0.1M Tris-base pH 9.0, 0.1M NaCl, 25% DMSO), was incubated for 4 h at 30° C. Reaction 2 conditions: The reaction mixture (total volume 500 µl, containing Orf11b (final conc. 0.01 mM), teicoplanin (final conc. 2 mM) and acyl-CoA (final conc. 1 mM) or acyl-NAC (final conc. 2.5 mM)+CoA (final conc. 1 mM) in a Tris buffer solution (0.1M Tris-base pH 6.5-7.5, 0.1M NaCl, 25% DMSO), was incubated for 4 h at 30° C.

It is discovered, unexpectedly, that a long lipid chain acyltransferase can catalyze either 2,6-di-acylation or 2,6-acyl-substitution reactions. Accordingly, one aspect of the present disclosure provides methods for preparing novel teicoplanin compound as described herein, including di-acyl teicoplanin analogs (2-acylamide, 6-acyl ester teicoplanin analogs) and teicoplanin compounds having a single uniform acyl group, using a long lipid chain acyltransferase (FIG. 25). In certain embodiments, a long lipid chain acyltransferase is an enzyme that catalyzes the acylation reaction by transferring a long lipid side chain from an acyl donor to an acyl acceptor. The long lipid chain acyltransferase for use in the preparation methods described herein can be a naturally-occurring enzyme, or a functional variant thereof. Exemplary long lipid chain acyltransferases for use in the preparation methods described herein include Orf11b and Dbv8. In certain embodiments, the long lipid chain acyltransferases for use in the preparation methods described herein is Orf11b. In certain embodiments, the long lipid chain acyltransferases for use in the preparation methods described herein is Dbv8. FIG. 7 shows the structural alignment of Orf11b with its homologs.

To prepare a teicoplanin compound as described herein, a long chain acyltransferase can be mixed with an acyl-acceptor and an acyl-donor under conditions allowing for occurrence of the enzymatic reaction catalyzed by the long-chain acyltransferase to produce the teicoplanin analog. The acyl-acceptor is of Formula (I-c) as described herein and the acyl-donor can be Formula (S-ii) or (S-iii) described herein. In certain embodiments, the acyl-donor is of Formula (S-ii). In certain embodiments, the acyl-donor is of Formula (S-iii). In certain embodiments, the acyl-donor is of Formula (S-ii) and the reaction mixture further comprises free CoA. In certain embodiments, the acyl-donor is of Formula (S-iii) and the reaction mixture further comprises free CoA.

To produce di-acyl teicoplanin analogs, the preparation method is preferred to be carried out under a pH value of 8-10 (e.g., pH of 9). To produce single uniform mono-acylated teicoplanin compounds, the preparation method is preferred to be carried out under a pH value of 6-8 (e.g., 6.5-7.5).

It is understood that the acyltransferase can be of catalytic amount in the provided method. In certain embodiments, the molar ratio of the acyltransferase to the acyl acceptor is from about 1000:1 to about 1:1. In certain embodiments, the molar ratio of the acyltransferase to the acyl acceptor is about 800:1 to about to about 10:1. In certain embodiments, the molar ratio of the acyltransferase to the acyl acceptor is about 600:1 to about 1:1. In certain embodiments, the molar ratio of the acyltransferase to the acyl acceptor is about 400 to 1 to about 50:1. In certain embodiments, the molar ratio of the acyltransferase to the acyl acceptor is about 300:1 to about 80:1. In certain embodiments, the molar ratio of the acyltransferase to the acyl acceptor is about 200:1 to about 100:1. In certain embodiments, the molar ratio of the acyltransferase to the acyl acceptor is about 200:1.

In certain embodiments, the molar ratio of the acyl donor to the acyl acceptor is about 1:100 to about 100:1. In certain embodiments, the molar ratio of the acyl donor to the acyl acceptor is about 1:50 to about 50:1. In certain embodiments, the molar ratio of the acyl donor to the acyl acceptor is about 1:20 to about 20:1. In certain embodiments, the molar ratio of the acyl donor to the acyl acceptor is about 1:10 to about 10:1. In certain embodiments, the molar ratio of the acyl donor to the acyl acceptor is about 1:5 to about 5:1. In certain embodiments, the molar ratio of the acyl donor to the acyl acceptor is about 1:3 to about 3:1. In certain embodiments, the molar ratio of the acyl donor to the acyl acceptor is about 1:2.5. In certain embodiments, the molar ratio of the acyl donor to the acyl acceptor is about 1:2.

The suitable condition for the provided preparation method also includes presence of a buffer solution. It is understood that the choice of buffer depends on the target pH for the acyl-transferation to occur. In certain embodiments, the buffer solution is a Tris buffer solution. In certain embodiments, the Tris buffer solution is at a pH of about 6.0 to about 8.0 to prepare mono-acylation teicoplanin compounds. In certain embodiments, the Tris buffer solution is at a pH of about 6.5 to about 7.5 to prepare mono-acylation teicoplanin compounds. In certain embodiments, the Tris buffer solution is at a pH of about 8.0 to about 10.0 to prepare diacylation teicoplanin compounds. In certain embodiments, the Tris buffer solution is at a pH of about 9.0 to prepare diacylation teicoplanin compounds.

The suitable condition may further includes presence of free CoA which act to facilitate the acyltransferation. In certain embodiments, the amount of CoA is about 10 to 0.1 equivalent to the acyl donor. In certain embodiments, the amount of CoA is about 5 to 0.5 equivalent to the acyl donor. In certain embodiments, the amount of CoA is about 2 to 0.5 equivalent to the acyl donor. In certain embodiments, the amount of CoA is about 1 equivalent to the acyl donor.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Long Chain Acyltransferase and Uses Thereof in Preparing Teicoplanin Analogs

Cloning and Protein Purification.

The orf11* and dbv8 genes were amplified and subcloned into the expression vector pET28a(+). The clones were transformed into *E. coli* BL21(DE3) for protein over-expression. A typical procedure is described as follows: One liter of LB medium containing 50 mg/L kanamycin was inoculated with 10 mL of an overnight culture grown in LB medium (containing 50 mg/L kanamycin), induced with 1 mL 1.0M IPTG (to give 1.0 mM; exact concentrations varied between proteins) at an OD600 of 0.7, and grown for a further 8 hours at 16° C. Cells were harvested by centrifugation at 6000 rpm for 20 min at 4° C., resuspended in 30 mL binding buffer (50 mM Tris at pH 8.0, 500 mM NaCl, 10 mM imidazole, 10% glycerol) and disrupted by microfluidizer. The cell lysate was centrifuged at 18000 rpm for 30 minutes to remove cell debris. The supernatant was applied to a $Ni^{2+}$-NTA agarose resin column (2 mL, Novagen) pre-equilibrated with binding buffer. The column was washed sequentially with 20 mL of binding buffer and 10 mL washing buffer (50 mM Tris at pH 8.0, 500 mM NaCl, 50 mM imidazole, 10% glycerol). The bound protein then was eluted with 10 mL of elution buffer (50 mM Tris at pH 8.0, 500 mM NaCl, 250 mM imidazole, 10% glycerol). Gel filtration was performed using an Äkta FPLC system equipped with an S-200 Superdex column (Amersham Bioscience) under isocratic conditions (50 mM Tris at pH 8.0, 500 mM NaCl). The buffer was exchanged using Millipore centrifugal filters and HEPES buffer (50 mM, pH 8.0). Protein purity was determined by SDS-PAGE and Western blotting, and electrospray mass spectrometry (ESI-MS). Protein concentrations were estimated using the Bradford assay.

Site-Directed Mutagenesis.

Site-directed mutagenesis was carried out using Quick-Change (Stratagene). The wild-type Orf11* was used as the template for single mutation. For multiple mutations, the single or double mutant was used as the template. All mutations were confirmed by DNA sequencing. Mutant proteins were purified with the same protocol for the wild-type Orf11*.

Enzymatic Activity Assay.

Orf11*/Dbv8 activity was determined by LC-MS. The assay mix containing enzyme (10 µg) and corresponding substrates (1 mM acyl-CoAs, 1 mM Tei-pseudoaglycone or vancomycin) in buffer (50 mM Tris pH 8.0, 100 mM NaCl, 1 mM DTT) (total volume 150 µl) was incubated for 2 h at 25° C. Each reaction mixture was centrifuged at 16,000 g for 5 min (Heraeus Biofuge Pico) and filtered on an ultracentrifugal filter unit (5 kDa cut-off membrane, Millipore) at due course. The filtrate was directly subjected to HPLC-ESI-LTQ (Agilent 1200 Series interfaced with an ESI source coupled to a Thermo-Finnigan LTQ-XL ion trap spectrometer), using a gradient of 0-60% acetonitrile in 0.1% TFA in water over 30 min. Online LC-MS spectra were recorded by Xcalibur (Thermo Fisher Scientific, Inc.).

Analytical Ultracentrifuge Analysis.

The sedimentation velocity experiments were performed with a Beckman-Coulter XL-I analytical ultracentrifuge. Samples and buffers were loaded into 12-mm standard double-sector Epon charcoal-filled centerpieces and mounted in an An-60 Ti rotor. We introduced 400 µl of a 1 mg/ml sample into the cell. Sedimentation velocity experiments were performed at rotor speed of 42,000 r.p.m. at 20° C. The signals of samples were monitored at 280 nm and collected every 3 min for 6 h. The raw data of experiments were calculated using SedFit software. The density and viscosity of buffer were calculated using Sednterp software.

Crystallization and Data Collection.

The purified proteins were crystallized using the hanging drop vapor-diffusion method. For apo-Orf11*, pyramidal crystals were obtained in a solution containing: 0.1M Tris pH 7.5, 2.5M NaCl. For Orf11*-decanoyl-CoA, hexagonal crystals were obtained in a solution containing: 0.1 mM MES pH6.5, 0.2M ammonium sulphate, 30% (V/V) PEG 5000 MME and 1 mM decanoyl-CoA. For Dbv8-decanoyl-CoA, crystals were obtained in a solution containing: 0.1M sodium cacodylate pH 6.5, 0.2M sodium acetate, 30% (V/V) PEG 8000 and 2 mM decanoyl-CoA. For Orf11*-OBG-CoA, crystals were obtained in a solution containing: 0.1M Tris pH 8.5, 1.4M ammonium tartrate, 1 mM CoA and 1 mM OBG. The protein crystals were transferred to the cryoprotectant solution containing glycerol (20%, v/v) prior to the x-ray diffraction experiment. X-ray diffraction data sets were collected on an ADSC Quantum-315 or Quantum-210 CCD detectors at beamlines 13B1 and 13C1 of the National Synchrotron Radiation Research Center (Taiwan) and beamlines 12B2 and 44XU of Spring-8 (Japan). Data were indexed and scaled with the HKL2000 package[1]. The redundancy independent merging R factor ($R_{r.i.m}$) and the precision indicating merging R factor ($R_{p.i.m.}$) were calculated using the program RMERGE. The contents of asymmetric units were estimated from the Matthews coefficient[2]. The data suggest that a value of 2.40 $Å^3$ $Da^{-1}$ with 48.7% solvent corresponds to one molecules per asymmetric unit in the $P2_12_12_1$ crystal, a value of 3.44 $Å^3$ $Da^{-1}$ with 64.2% solvent content indicates one molecules per asymmetric unit in the $P6_5$ crystal and a value of 2.89 $Å^3$ $Da^{-1}$ with 57.4% solvent content indicates one molecules per asymmetric unit in the $P6_2$ crystal.

Structure Determination and Refinement.

The initial phase was determined by the single wavelength anomalous dispersion method. The anomalous diffraction data were collected by selenium labeled Orf11*. The single wavelength anomalous dispersion (SAD) method was used to obtain phase information, and CRANK was used to find the phase solution. Other native structures were solved by the molecular replacement method using the Se-Orf11* as the search model. The CRANK pipeline started with substructure detection and ended with model building, including procedures of substructure detection by AFRO/CRUNCH2[4], substructure refinement by BP3[5], Hand determination and density modification by SOLOMEN, and model building by BUCCANEER. Phase extension yielded electron density maps into which a polypeptide model was built with the program COOT. The model was further refined with REFMAC. Figures were generated using PyMO. Detailed refinement statistics are given in Table 1.

Protein expression, purification and confirmation of purity were performed according to standard protocols. Acyl-CoA analogs were chemically synthesized as described previously (Huang, Y. T. et al. In vitro characterization of enzymes involved in the synthesis of nonproteinogenic residue (2S,3S)-beta-methylphenylalanine in glycopeptide antibiotic mannopeptimycin. Chembiochem 10, 2480-2487, doi:10.1002/cbic.200900351 (2009); Li, T. L., Spiteller, D. & Spencer, J. B. Identification of a pentaketide stilbene produced by a type III polyketide synthase from Pinus sylvestris and characterisation of free coenzyme A intermediates. Chembiochem 10, 896-901, doi:10.1002/cbic.200800840 (2009)). Single-wavelength anomalous dispersion (SAD) and molecular replacement (MR) methods were used to solve structures of native and complex Orf11*/Dbv8. Mutants were made by using QuickChange®. Biochemical analyses for wild type protein and mutants were performed using LC-MS. Oligomerization states of the proteins in solution were determined by gel filtration chromatography and analytical ultracentrifugation (AUC). Substrate-enzyme affinity was determined using isothermal titration calorimetry (ITC). Biological assays were performed according standard protocols.

Accession Codes.

The coordinates have been deposited in the Protein Data Bank under accession number: Se-Orf11* (4MFJ), Orf11*H196A/decanoyl-CoA (4MFK), Orf11*H196A/decanoyl-CoA/Tei pseudoaglycone (4MFL), Orf11*H196A/decanoyl-CoA-Tei pseudoaglycone (4MFP), Orf11*H196A/CoA/10C-teicoplanin (4MFQ), Orf11*H196A/decanoyl peroxide-CoA (4MFS), Orf11*H196A/sulfurperoxide-CoA/decanoylperoxide (4MFT), Orf11*H196A/sulfenyl-CoA/decanoic acid (4MFW), Orf11*H196A/sulfurperoxide-CoA/decanoic acid (4MFX), Orf11*/CoA-disulfide/decanoic acid (4MFY), Dbv8/decanoyl-CoA (4MFZ), Orf11*/octyl peroxide-CoA (4MG0), Orf11*/octyl peroxide-CoA/glucose (4MG1).

Six high-resolution structures of the enzyme in unary/binary/ternary complexes were resolved. It was found a multistage conformational change in response to binding of acyl-CoA, enabling binding of Tei-pseudoaglycone and proceeding of the acyltransfer reaction. The acyl group can be considerably diverse. Both vancomycin/synthetic acyl-NAC can also serve as an acyl acceptor/donor, respectively. Formation of diacyl Tei in an enzyme reaction conducted at high pH could result in novel 1,4-diaxial-acyl-swapping analogs. Beyond acyltransferation, it was also discovered a 4-electron oxidation reaction to oxidize β-octyl-glucose, for which the proposed CoA-sulfur-peroxide mediated mechanism was validated by additional seven stepwise structures.

Figure 6:
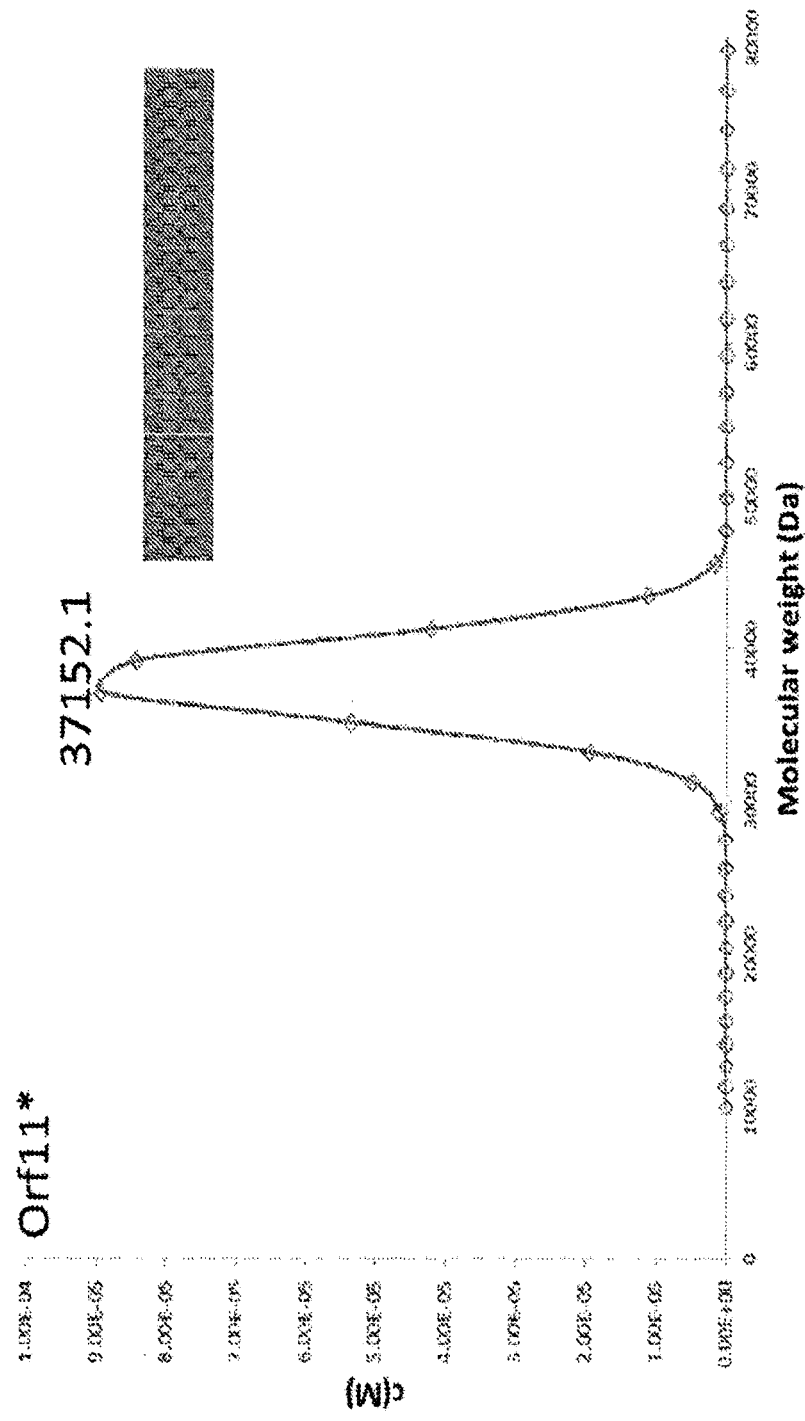
FIG. 6 shows analytical ultracentrifugation analysis of Orf11*, Orf11*/decanoyl-CoA and Orf11*/decanoyl-CoA/Tei pseudoaglycone. The AUC data were analyzed using SedFit (http://www.analyticalultracentrifugation.com/default.htm). The calculated c(M) and c(S) distributions are shown in panels (a) (c) (e) and panels (b) (d) (f), respectively. The insert grayscale bars indicate the residuals bitmap in each fit.
Figure 6:
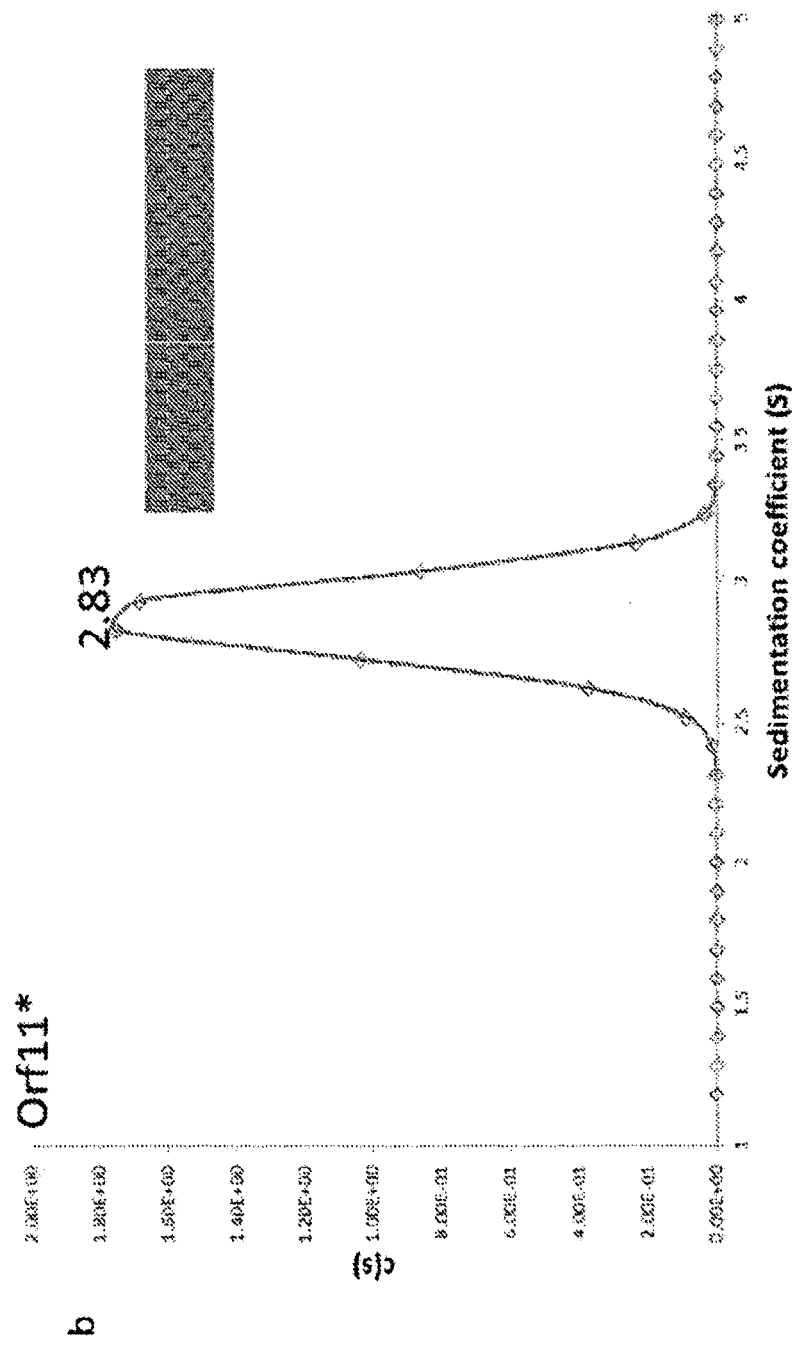
Figure 6:
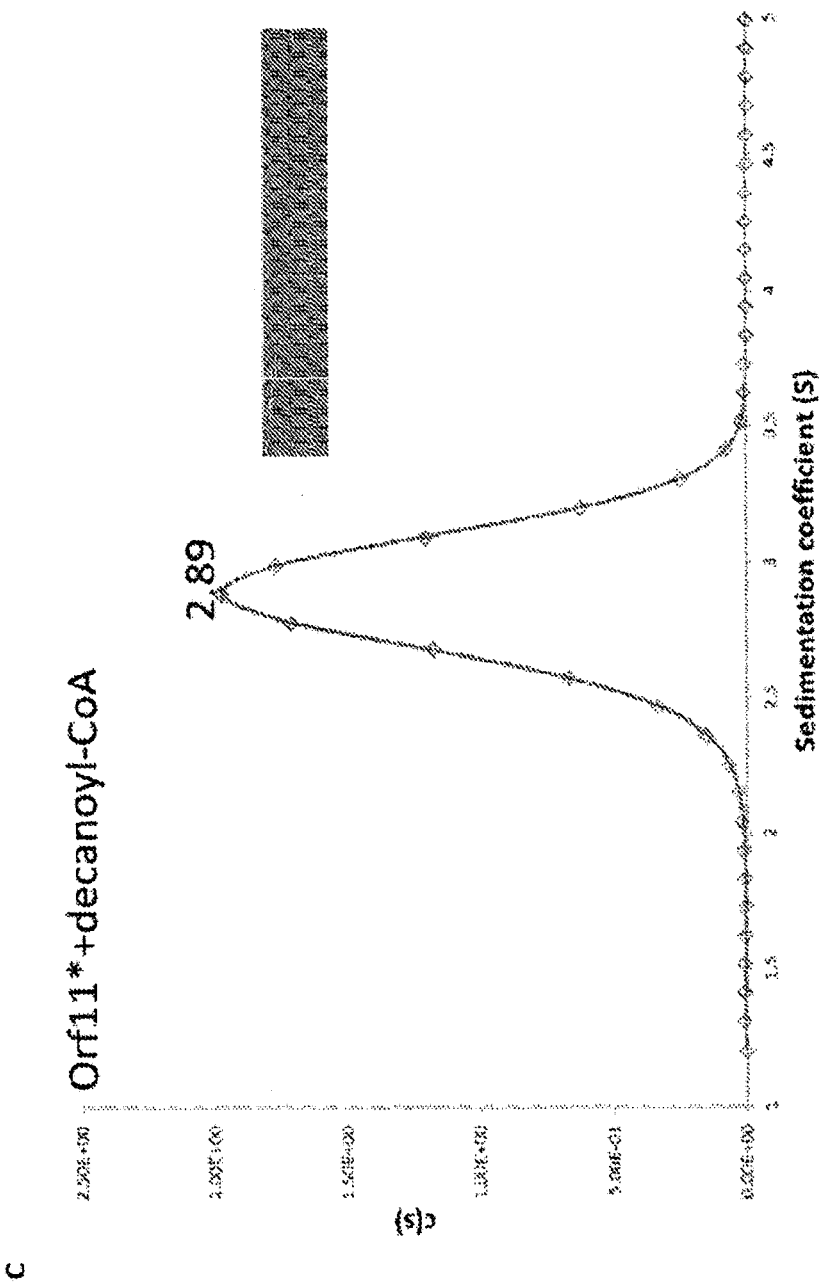
Figure 6:
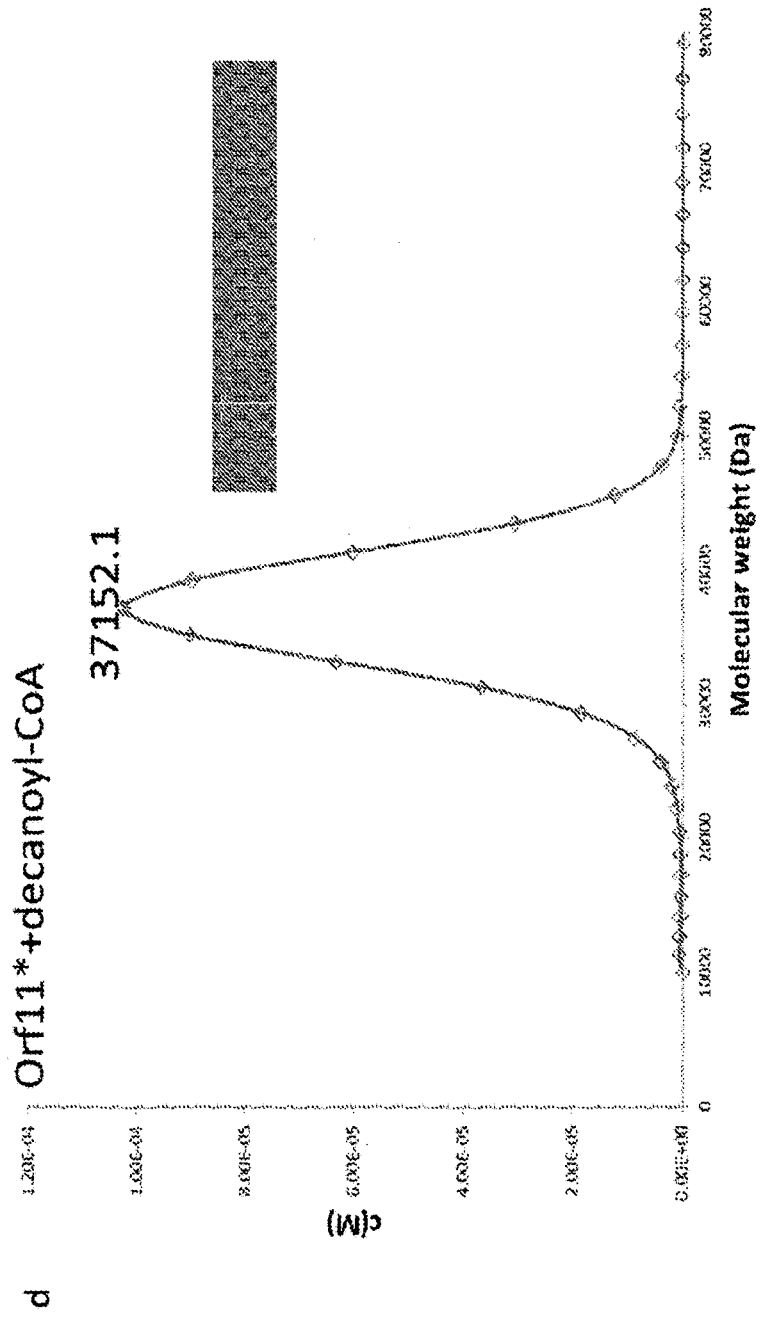
Figure 6:
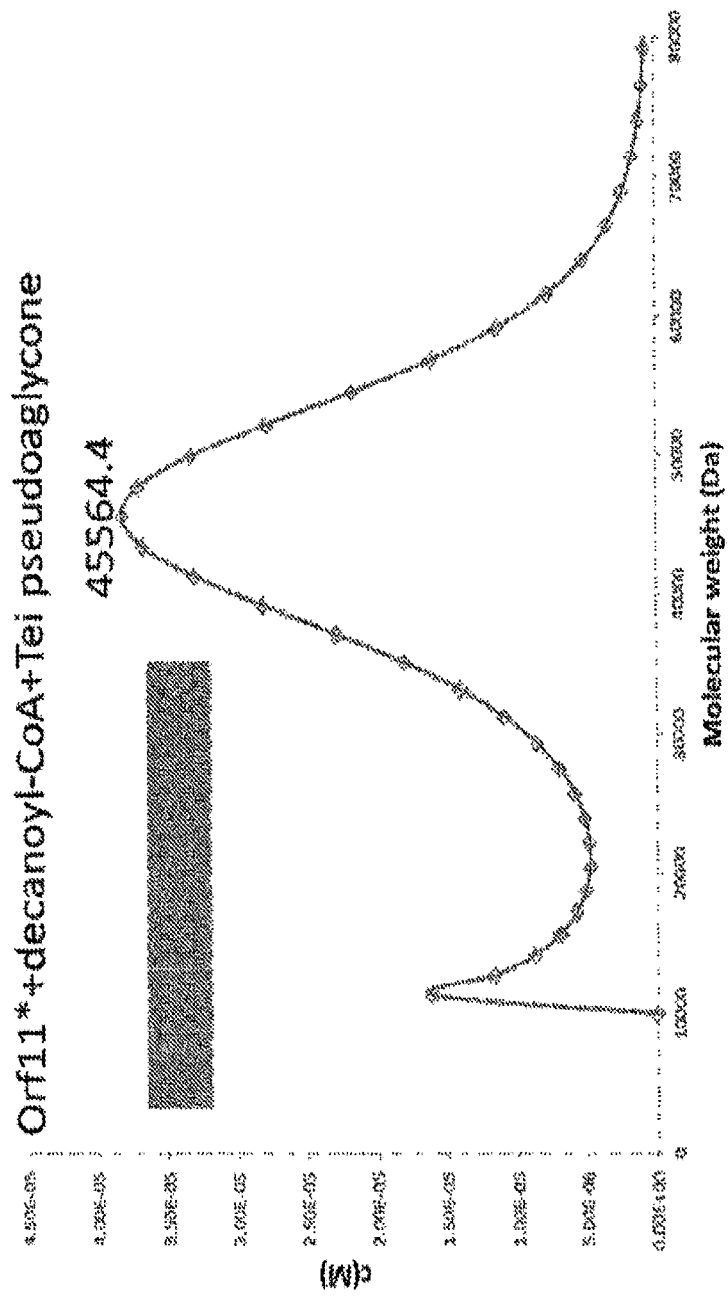
Figure 6:
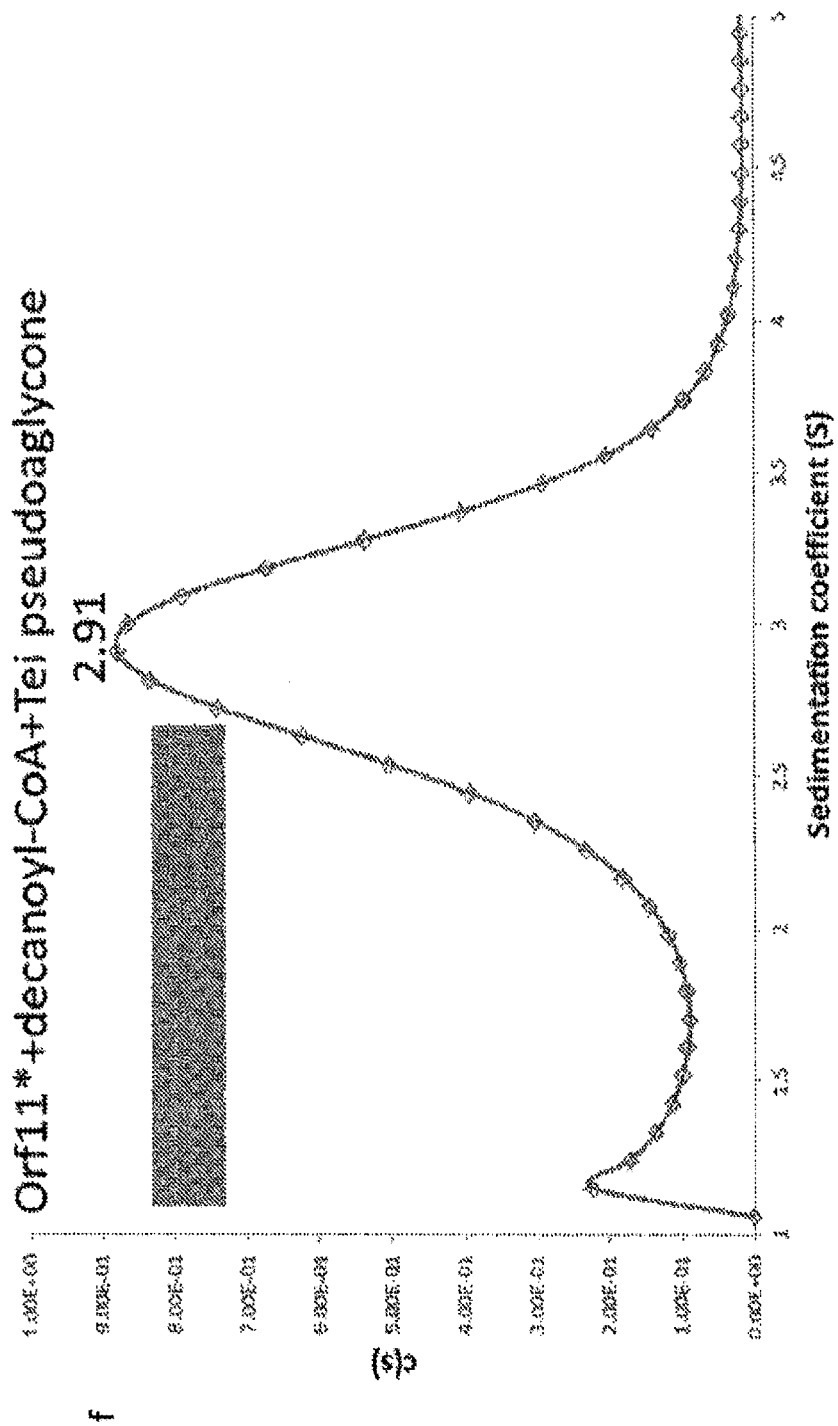

Initially, due to lack of structural homologs in database, the preliminary phase was solved using single wavelength anomalous diffraction (SAD) on crystals of selenomethionyl Orf11*, which then served as a search model for other native and ligand-complexed data sets in the molecule replacement (MR) routine. The resolutions of these multi-phased structures range in 1.6-2.7 Å with reasonable values of $R_{work}$ and $R_{free}$ as shown in FIG. 6. The structures of Orf11*/Dbv8 and complexes thereof all contain one molecule in an asymmetric unit, consistent with analysis of gel filtration chromatography and analytical ultracentrifugation (FIG. 6). These results indicate that monomers are biologically active state for Orf11*/Dbv8, in contrast to GCN5-related N-acetyltransferases (GNATs) which are active in dimers.

Figure 8:
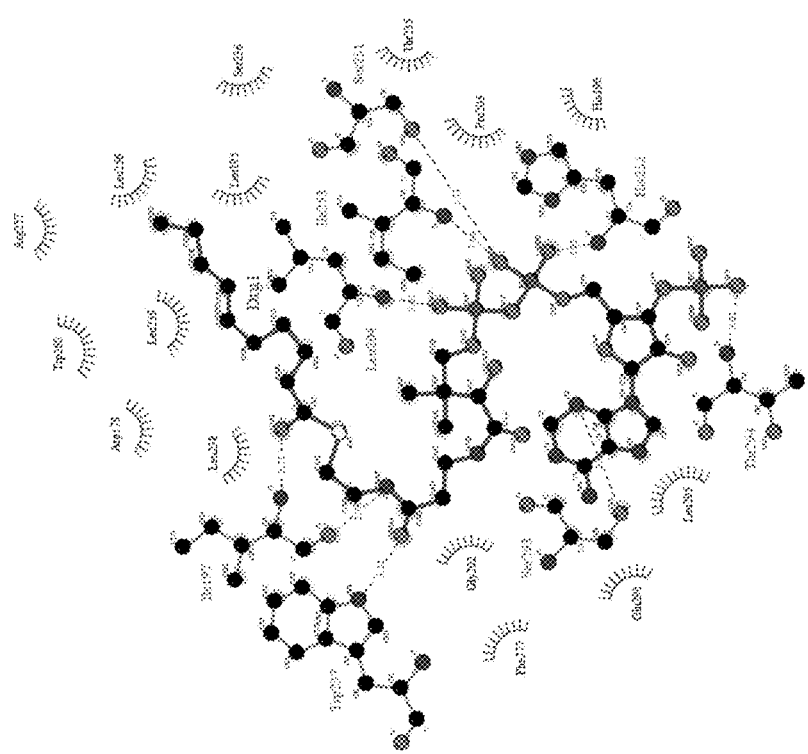
FIG. 8 shows ligplot diagram of the interaction between decanoyl-CoA and Orf11*. This plot was generated using the Ligplot software.
Figure 9:
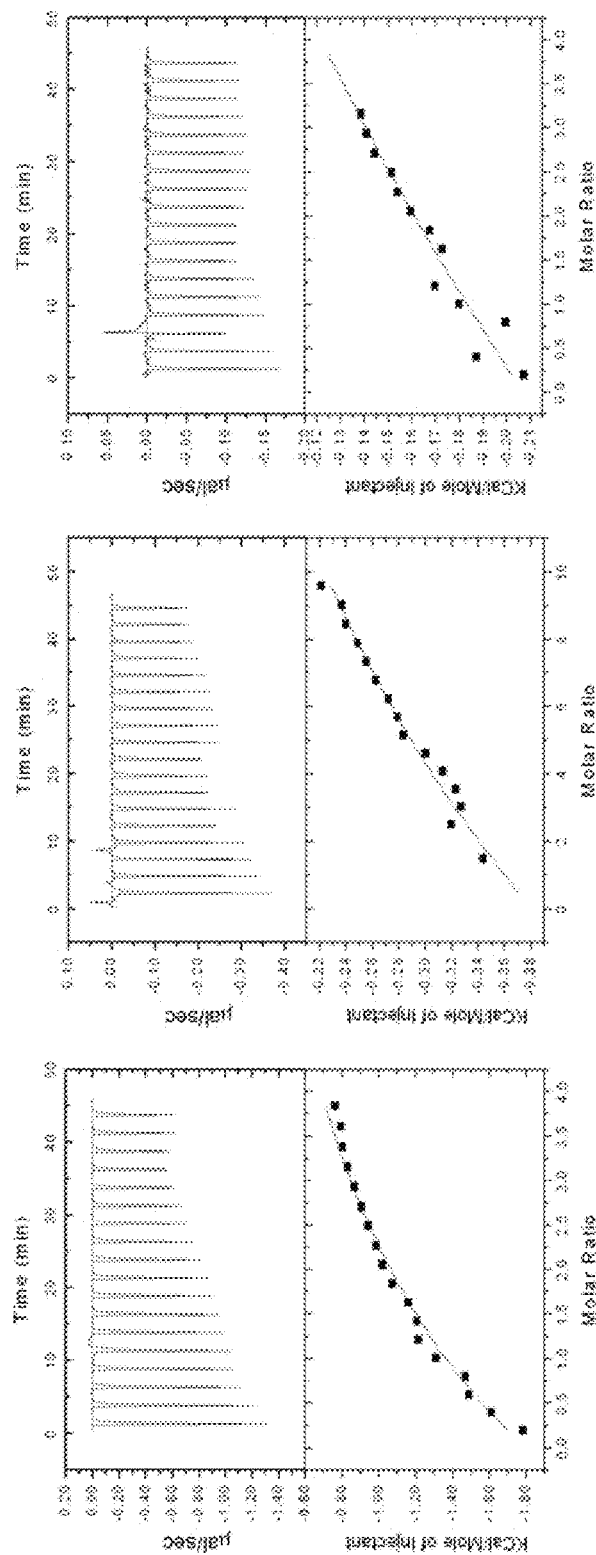
FIG. 9 shows isothermal titration calorimetry (ITC) analysis of Orf11*. ITC thermograms of Orf11* versus CoA, acetyl-CoA, butyryl-CoA, hexanoyl-CoA, octanoyl-CoA, decanoyl-CoA, lauroyl-CoA, myristoyl-CoA, palmitoyl-CoA, stearoyl-CoA or Tei-pseudoglycone. Each exothermic heat pulse corresponds to an injection of 2 μl of ligands (1 mM~5 mM) into a protein solution (0.1 mM); integrated heat areas constitute a differential binding curve that was fitted with a standard single-site binding model (Origin 7.0, MicroCal iTC$_{200}$).
Figure 9:
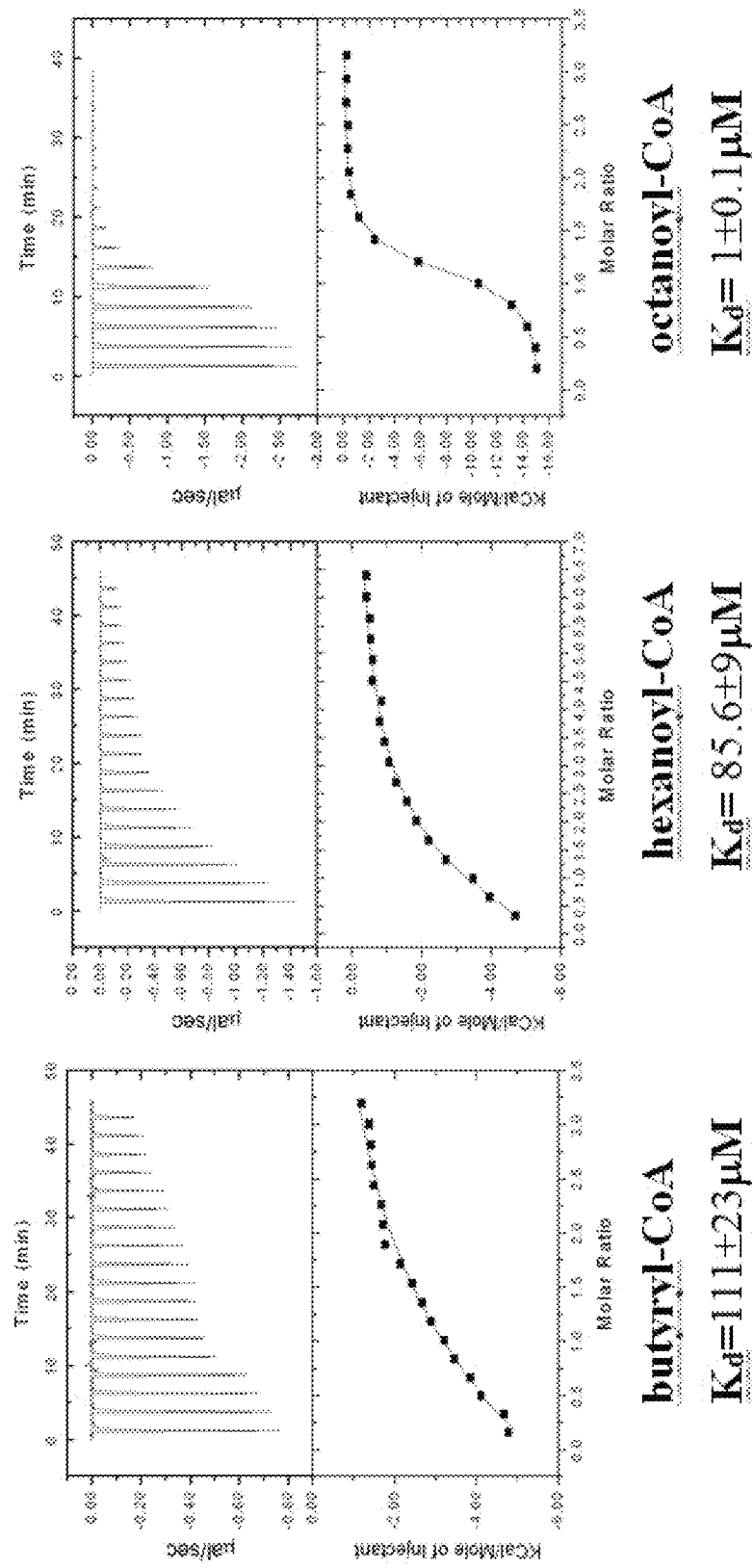
Figure 9:
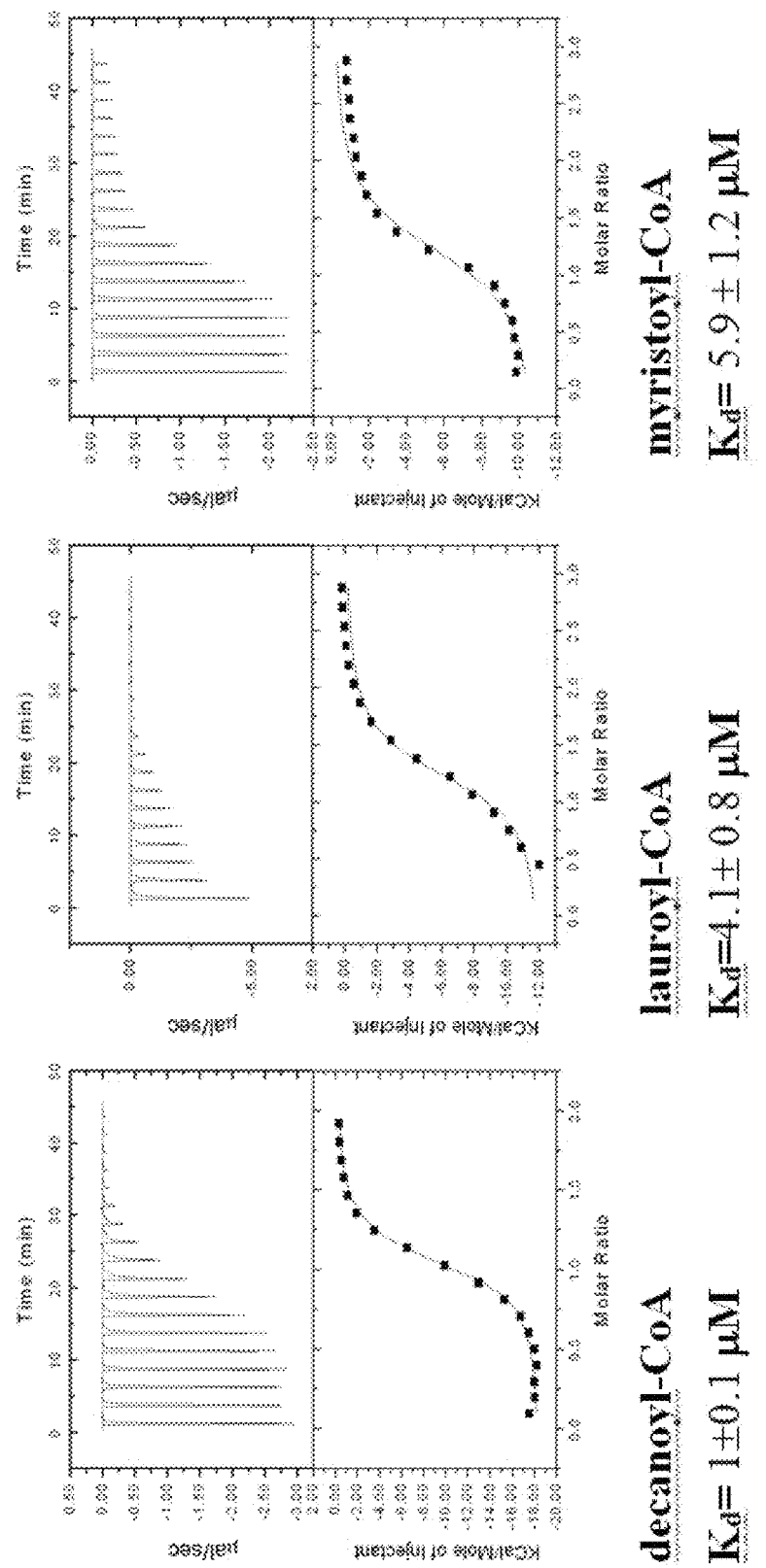
Figure 9:
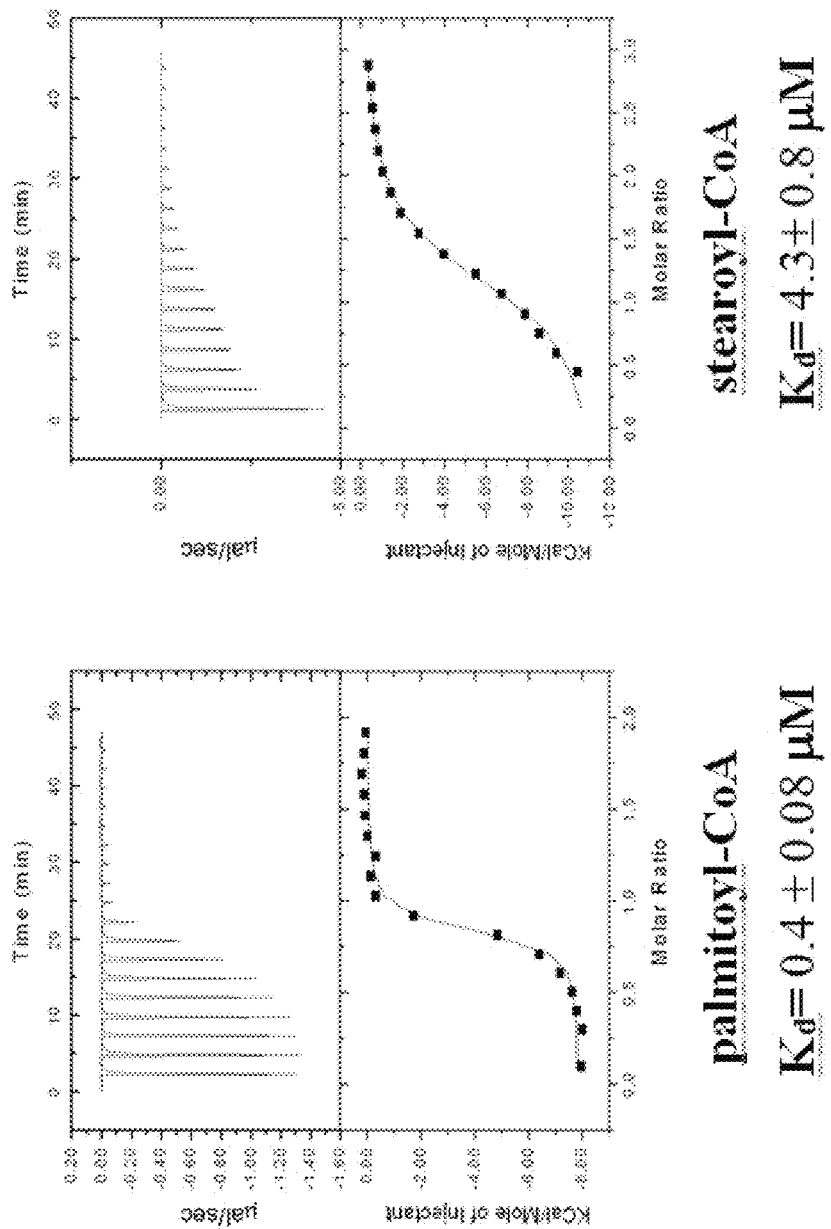

The GNAT domain in Orf11*/Dbv8 differs from the canonical GNAT fold as it lacks the first β strand, and the C-terminus extends with four additional helices (α10-α13). β-Strands β3 and β4 splay apart at C-termini, where Pro198 replaces a typical β-bulge. In a decanoyl-CoA-complexed binary structure (FIG. 2c), the decanoyl-CoA bends in an 'S' shape edging in the splayed fingers β3 and β4 (FIG. 8). The pantethine moiety is mediated by the loop β3-α9; the phosphate groups of 3',5'-phosphoadenosine are adjacent to the main chain atoms of the C-terminal helices (α10-α13), where the loop α10-α11 may function as a P-loop makeshift. The ribose is in a 2'endo-conformation as commonly observed in acetyltransferase co-crystal structures (Vetting, M. W. et al. Structure and functions of the GNAT superfamily of acetyltransferases. Arch Biochem Biophys 433, 212-226, doi:10.1016/j.abb.2004.09.003 (2005)). The decanoyl moiety uniquely extends into a deep-wide tunnel moulded by β4, α11, and the loop β4-α10 (FIG. 2d). Biochemically, except for steric limitation (the α carbon cannot be branched and the β carbon cannot be charged), the acyl moiety can be as lengthy or bulky as palmitoyl, naphthaleneacetyl or biphenylacetyl (Table 2), making Orf11*/Dbv8 an adaptable enzyme able to generate new glycopeptide analogs. Isothermal titration calorimetry (ITC) analysis showed that Orf11*/Dbv8 does not bind benzoyl-, malonyl- and methylmalonyl-CoA, in line with the limitation aforementioned. The dissociation constants ($K_d$) decline with increase of acyl chain length for up to $C_{10}$, whereas the trend reverses when the chain length exceeds $C_{10}$, suggesting $C_{10}$ as the optimal length for the enzyme. Interestingly, the dissociation constants ($K_d$) decline again when the chain length extends to $C_{16}$, suggesting the longer lipid chain may adopt a new shape to increase the binding affinity (FIG. 9).

Figure 10:
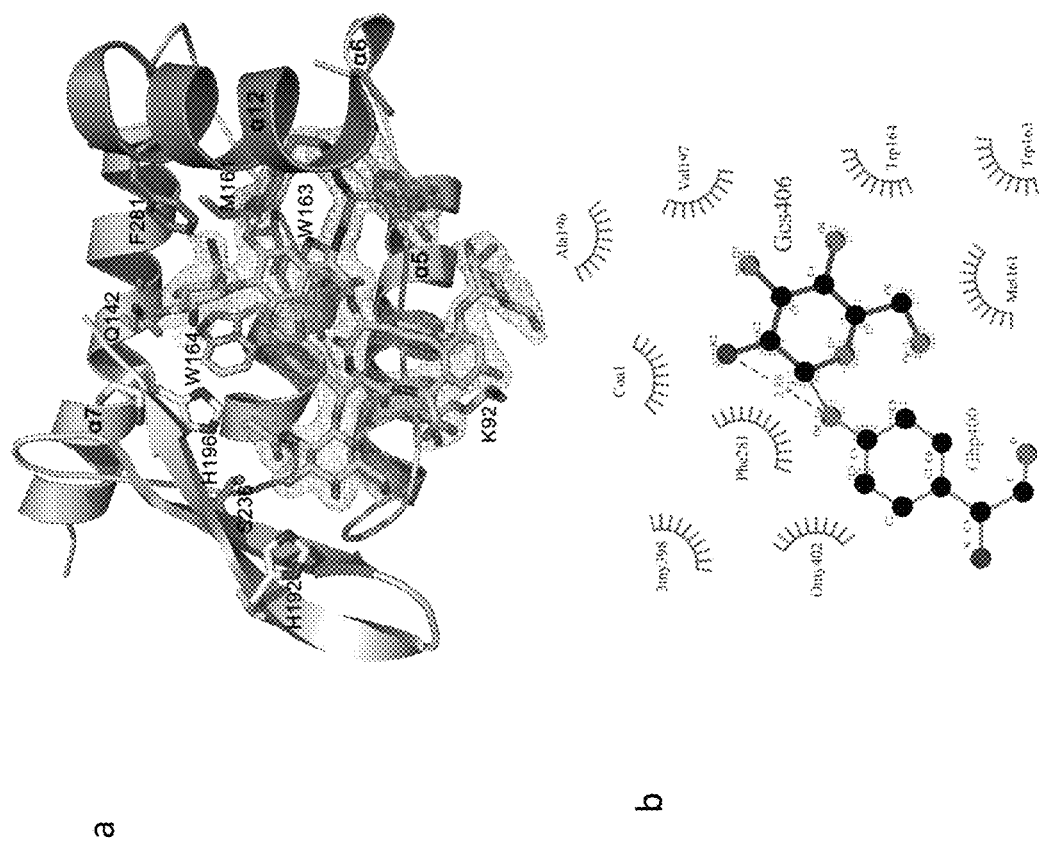
FIG. 10 shows the binding site of Tei pseudoaglycone in Orf11*. (a) The binding site of Tei pseudoaglycoen in the structure of Orf11*H196A-decanoyl-CoA-Tei pseudoaglycone complex. The $2F_o-F_c$ electron density map of Tei pseudoaglycone is contoured at 1 σ. (b) The Ligplot diagram shows the binding site of the r4 glucosamine in the complex.

Superimposition of unary (free) and binary (in complex with decanoyl-CoA) structures (RMSD=1.25 for 319 Cα of Orf11*) suggests that the GNAT domain undergoes a substantial conformational change upon binding of acyl-CoA in constrast to the N-terminal domain that holds steadfast during the course of binding (FIG. 2e). It is noted that the loop β3-α9 in the GNAT domain makes 180° inside-out twist when acyl-CoA comes close to the binding site. This wavering connects two salt bridges (FIG. 2f), pulling the GNAT domain toward the all-helix domain. The overall 10 Å displacement (or 15° provided residue V197 the axis) may shape a closed active conformation in the domain junction to form the Tei pseudoaglycone binding site (FIG. 2e). To locate the accurate Tei pseudoaglycone-binding site, ternary structures in complex with both decanoyl-CoA and Tei pseudoaglycone were attempted. The ternary crystals were successfully obtained only through soaking the decanoyl-CoA-complexed H196A mutant crystals with Tei pseudoaglycone 3, suggesting the closed conformation is necessary for the pseudoaglycone binding (FIG. 2g). An extra cloud of electron density offside acyl-CoA (surrounded by β2, β3, α12 and the loop α5-α6) was identified, which fitted well with Tei pseudoaglycone 3. In general, the upper part of the heptapeptide core interacts with the enzyme (β2, β3, α8, and α12) through van der Waals forces, whereas the lower part is free of contact. The central 4Hpg glucosamine is enclosed by a slew of residues (Q142, M161, W163, W164, H196 and F281) but lack of specific interactions, suggesting the sugar is less constrained (see below) (FIG. 10). ITC analysis buttressed the observations as Tei pseudoaglycone 3 or CoA 5 barely binds to the enzyme, suggesting the enzyme assumes an open state (FIG. 2e and FIG. 10). Superposition of unary, binary and ternary structures concluded that acyl-CoA rather than CoA plays a pivotal role in configuring the GNAT domain for Tei pseudoaglycone binding (FIG. 2h).

Both Orf11* and Dbv8 fold in a dumbbell-like architecture with two sizable subdomains joined by a short spacer—an unusual all-helix N-domain and a GNAT-like C-domain (FIGS. 2 a and b). The all-helix domain is composed of eight helices (α1-α8) with two helix-turn-helix motifs in tandem (α1-α4), spooling a perpendicular 4-helix bromodomain-like central core (α5-α8) (residues 175-324, the Orf11* numbering system is referred to unless otherwise stated), a reminiscence of eukaryotic histone acetyltransferase (HAT) complexes. Helices α5 and α6 juxtapose parallelly while connected transversely by a long loop (residues 84-100), in contrast to the antiparallel arrangement of helices α7 and α8. The GNAT-like domain has a central 5-β-strand core (β1-β5) flanked by two α helices, one short (α9) and one fragmented long helix (the latter is composed of four and six short helices for Orf11* and Dbv8, respectively), on each side. Dali server search suggests that the N-terminal subdomain of Orf11*/Dbv8 is structurally akin to the AAA+ protein family (ATPases associated with diverse cellular activities) (supplementary FIG. 2)[13], whereas based on the functional consideration Orf11*/Dbv8 may look more like a miniature of CBP/p300 in the HAT protein family. The CBP/p300 houses a large GNAT domain alongside several smaller domains, including helix-turn-helix and bromodomain for recruiting acetylated lysine residues in histones.

The bromo-like domain in Orf11*/Dbv8 may likewise act to recognize the peptide substrate Tei/A40926 pseudoaglycone. With these unique traits Orf11*/Dbv8 may represent a new architecture in the prokaryotic NAT enzyme family.

The GNAT domain in Orf11*/Dbv8 differs from the canonical GNAT fold as it lacks the first β strand, and the C-terminus extends with four additional helices (α10-α13). β-Strands β3 and β4 splay apart at C-termini, where Pro198 replaces a typical β-bulge[9-11]. In a decanoyl-CoA-complexed binary structure (FIG. 2c), the decanoyl-CoA bends in an 'S' shape edging in the splayed fingers β3 and β4 (FIG. 8). The pantethine moiety is mediated by the loop β3-α9; the phosphate groups of 3',5'-phosphoadenosine are adjacent to the main chain atoms of the C-terminal helices (α10-α13), where the loop α10-α1 may function as a P-loop makeshift (Verstraeten, N., Fauvart, M., Versees, W. & Michiels, J. The universally conserved prokaryotic GTPases. Microbiol Mol Biol Rev 75, 507-542, second and third pages of table of contents, doi:10.1128/MMBR.00009-11 (2011)). The ribose is in a 2'endo-conformation as commonly observed in acetyltransferase co-crystal structures (Vetting, M. W. et al. Structure and functions of the GNAT superfamily of acetyltransferases. Arch Biochem Biophys 433, 212-226, doi: 10.1016/j.abb.2004.09.003 (2005)). The decanoyl moiety uniquely extends into a deep-wide tunnel moulded by β4, α11, and the loop β4-α10 (FIG. 2d). Biochemically, except for steric limitation (the α carbon cannot be branched and the β carbon cannot be charged), the acyl moiety can be as lengthy or bulky as palmitoyl, naphthaleneacetyl or biphenylacetyl (Table 2), making Orf11*/Dbv8 an adaptable enzyme able to generate new glycopeptide analogs. Isothermal titration calorimetry (ITC) analysis showed that Orf11*/Dbv8 does not bind benzoyl-, malonyl- and methylmalonyl-CoA, in line with the limitation aforementioned. The dissociation constants ($K_d$) decline with increase of acyl chain length for up to $C_{10}$, whereas the trend reverses when the chain length exceeds $C_{10}$, suggesting $C_{10}$ as the optimal length for the enzyme. Interestingly, the dissociation constants ($K_d$) decline again when the chain length extends to $C_{16}$, suggesting the longer lipid chain may adopt a new shape to increase the binding affinity (FIG. 9).

Superimposition of unary (free) and binary (in complex with decanoyl-CoA) structures (RMSD=1.25 for 319 Cα of Orf11*) suggests that the GNAT domain undergoes a substantial conformational change upon binding of acyl-CoA in constrast to the N-terminal domain that holds steadfast during the course of binding (FIG. 2e). It is noted that the loop β3-α9 in the GNAT domain makes 180° inside-out twist when acyl-CoA comes close to the binding site. This wavering connects two salt bridges (FIG. 2f), pulling the GNAT domain toward the all-helix domain. The overall 10 Å displacement (or 15° provided residue V197 the axis) may shape a closed active conformation in the domain junction to form the Tei pseudoaglycone binding site (FIG. 2e). To locate the accurate Tei pseudoaglycone-binding site, ternary structures in complex with both decanoyl-CoA and Tei pseudoaglycone were attempted. The ternary crystals were successfully obtained only through soaking the decanoyl-CoA-complexed H196A mutant crystals with Tei pseudoaglycone 3, suggesting the closed conformation is necessary for the pseudoaglycone binding (FIG. 2g). An extra cloud of electron density offside acyl-CoA (surrounded by β2, β3, α12 and the loop α5-α6) was identified, which fitted well with Tei pseudoaglycone 3. In general, the upper part of the heptapeptide core interacts with the enzyme (β2, β3, α8, and α12) through van der Waals forces, whereas the lower part is free of contact. The central 4Hpg glucosamine is enclosed by a slew of residues (Q142, M161, W163, W164, H196 and F281) but lack of specific interactions, suggesting the sugar is less constrained (see below) (FIG. 10). ITC analysis buttressed the observations as Tei pseudoaglycone 3 or CoA 5 barely binds to the enzyme, suggesting the enzyme assumes an open state (FIG. 2e and FIG. 9). Superposition of unary, binary and ternary structures concluded that acyl-CoA rather than CoA plays a pivotal role in configuring the GNAT domain for Tei pseudoaglycone binding (FIG. 2h).

Figure 3:
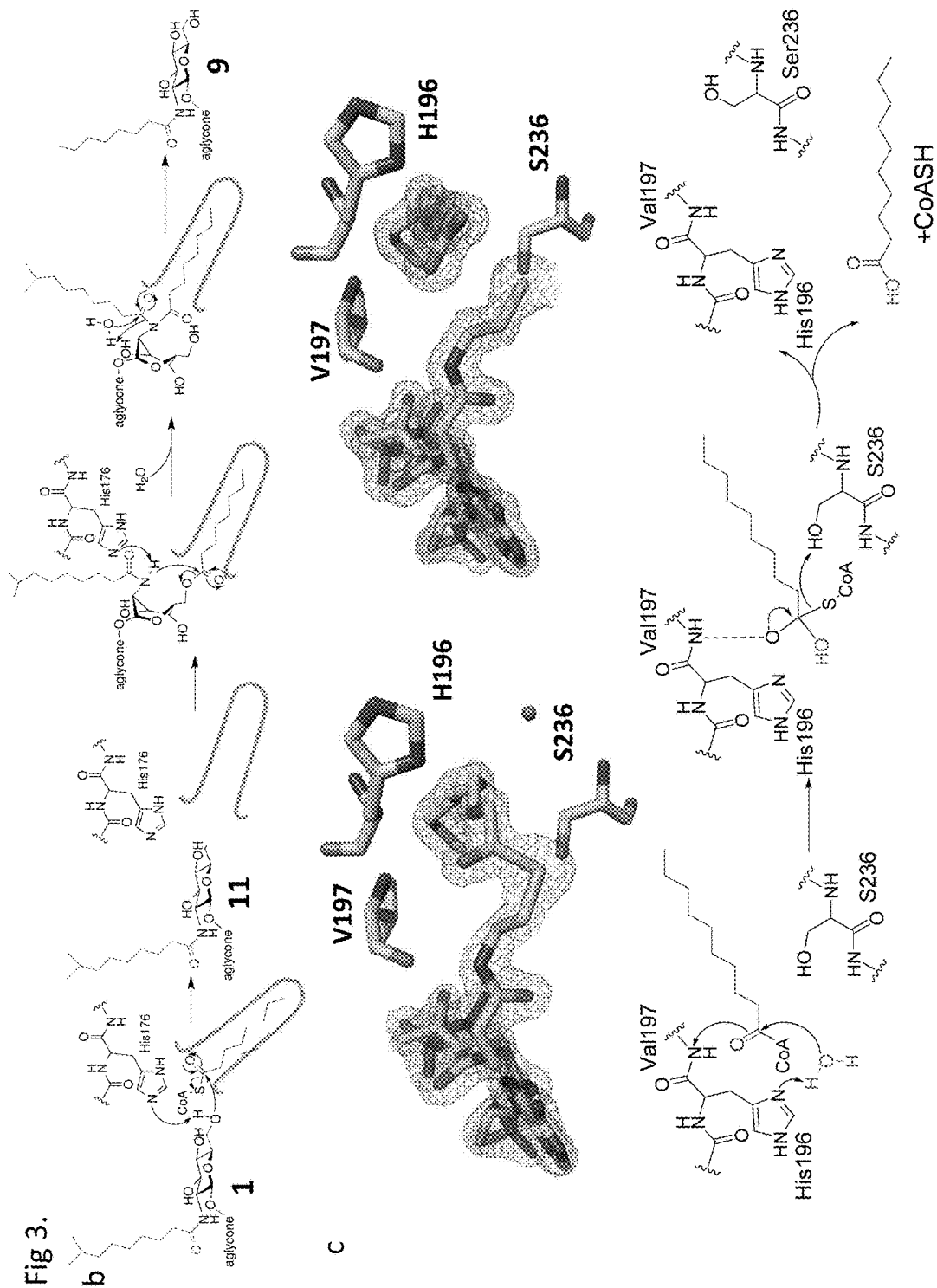
FIG. 3 shows the active site views of Orf11* and its enzymatic mechanisms. (a) The structural views for three reaction states—pre-acylation (left), tetrahedron intermediacy (center) and post-acylation (right)—in three ternary structures (top panel), and the proposed enzymatic mechanism for the Orf-11*-catalyzed acyltransfer reaction (bottom panel). The H196A is mutated back to His196 according to its geometry at the active site of the binary structure. The $2F_o-F_c$ electron density maps are contoured at 1.2 σ. (b) The proposed mechanism of the 1,4-diaxial acyl-swapping reaction, in which the lipid tunnel in Orf11* is shown. (c) The structural views (top panel) and proposed mechanism (bottom panel) of acyl-CoA hydrolysis half reaction in the active site of Orf11*. The $2F_o-F_c$ electron density maps are contoured at 1.5 σ.

It has been well documented that acyltransfer can proceed through direct transfer or an acyl-enzyme intermediate as seen in histone ATs (Vetting, M. W. et al. Structure and functions of the GNAT superfamily of acetyltransferases. Arch Biochem Biophys 433, 212-226, doi:10.1016/j.abb.2004.09.003 (2005); Marmorstein, R. & Roth, S. Y. Histone acetyltransferases: function, structure, and catalysis. Curr Opin Genet Dev 11, 155-161 (2001)). Three reaction states—pre-acylation, tetrahedron intermediacy and post-acylation—were found in three ternary structures, suggesting that the acyltransfer reaction of Orf11*/Dbv8 follows the direct transfer (FIG. 3a). It is suggested H196 acts as the general base to deprotonate the C-2 $NH_2$ of the glucosamine at 4Hpg, which then attacks the thioester carbonyl carbon of acyl-CoA. The resulting tetrahedron transition is stabilized by the main-chain amide of V 197, where an oxyanion hole likely resides. Collapse of the transition results in N-acylation of psudoaglycone, whereof leaving of CoA may be facilitated by S236 through protonating the sulfur anion into sulfhydryl. This mechanistic notion was supported by mutagenic and biochemical assays as relative activities of mutants H196A and H196A/S236A double-mutation plunged significantly (5% and 0%, respectively relative to WT) (Table 3). Taken together, acyl-CoA likely binds to the enzyme at the first place, and initiates protein conformational change to form the Tei pseudoaglycone binding site. Upon completion of the acyltransfer reaction, CoA likely leaves prior to the acylated product to enable the enzyme retaking the open state for next reaction cycle.

Figure 4A:
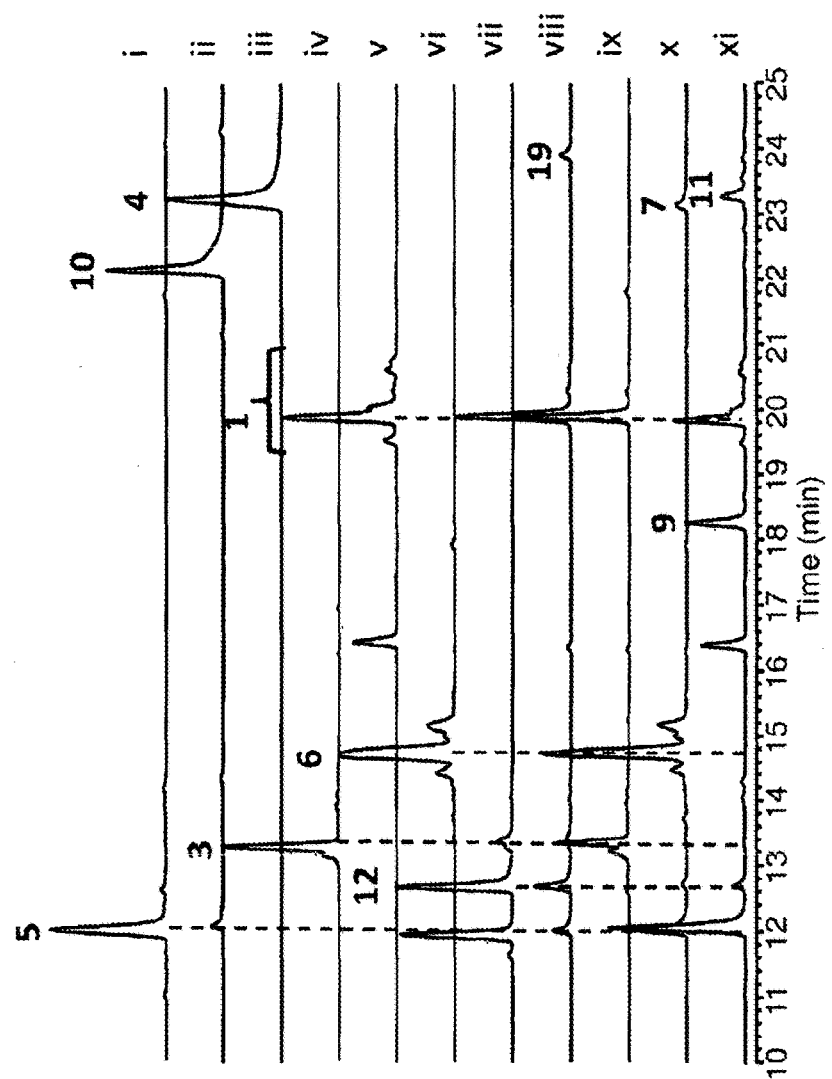
FIG. 4 shows liquid chromatography (LC) traces and mass spectra. (a) LC traces: (i) CoA 5, (ii) octyl-CoA 10, (iii) decanoyl-CoA 4, (iv) Tei pseudoaglycone 3, (v) Tei 1 (major: A2-2 and A2-3, minor: A2-1, A2-4, A2-5 and RS1 to RS4), (vi) Van 6, (vii) formation of CoA-disulfide 12 in an enzymatic reaction with addition of decanoyl-CoA 4, (viii) formation of Tei 1 and diacyl-teicoplanin ($C_{10},C_{10}$-Tei) 19 in an enzymation reaction with addition of decanoyl-CoA 4 and Tei pseudoaglycone 3, (ix) formation of Tei 1 (A2-3) in an enzymation reaction with addition of decanoyl-NAC 8 and Tei pseudoaglycone 3, (x) formation of $C_8$-Van 7 in an enzymatic reaction with addition of decanoyl-CoA 4 and Van 6, (xi) formation of $C_8$-Tei 9 and diacyl-teicoplanin ($C_8,C_{10}$-Tei) 11 in an enzymatic reaction with addition of octyl-CoA 10 and Tei 1. (b) Mass spectra for (i) CoA 5, (ii) octyl-CoA 10, (iii) decanoyl-CoA 4, (iv) Tei pseudoaglycone 3, (v) Tei A2-2 1, (vi) Van, (vii) CoA disulfide 12, (viii) Tei A2-3 1, (ix) $C_{10},C_{10}$-Tei 19 (m/z is shown as double charged ions), (x) $C_8$-Van 7, (xi) $C_8$-Tei 9, (xii) $C_8,C_{10}$-Tei 11 (m/z is shown as double charged ions).
Figure 4B:
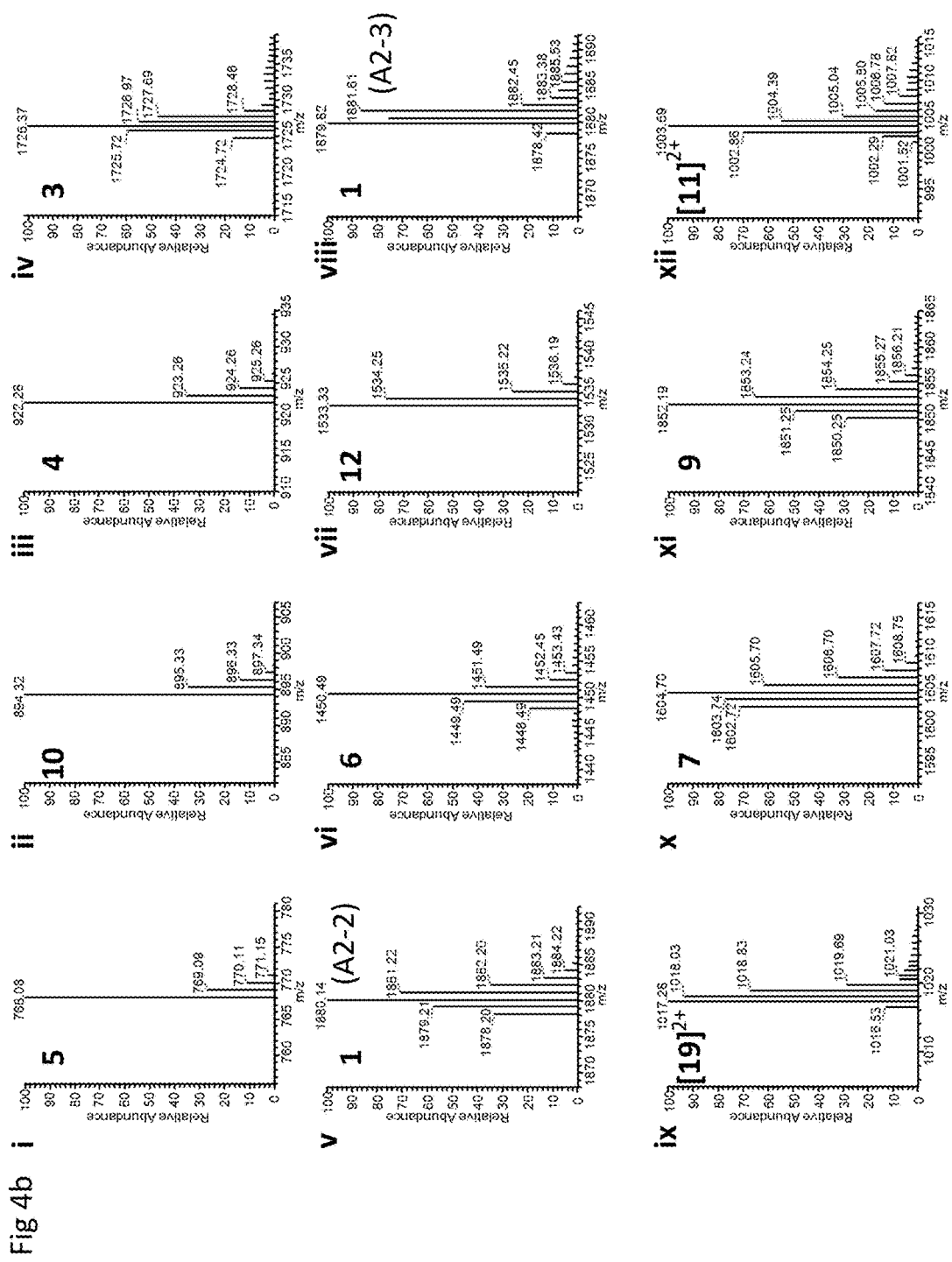
Figure 11:
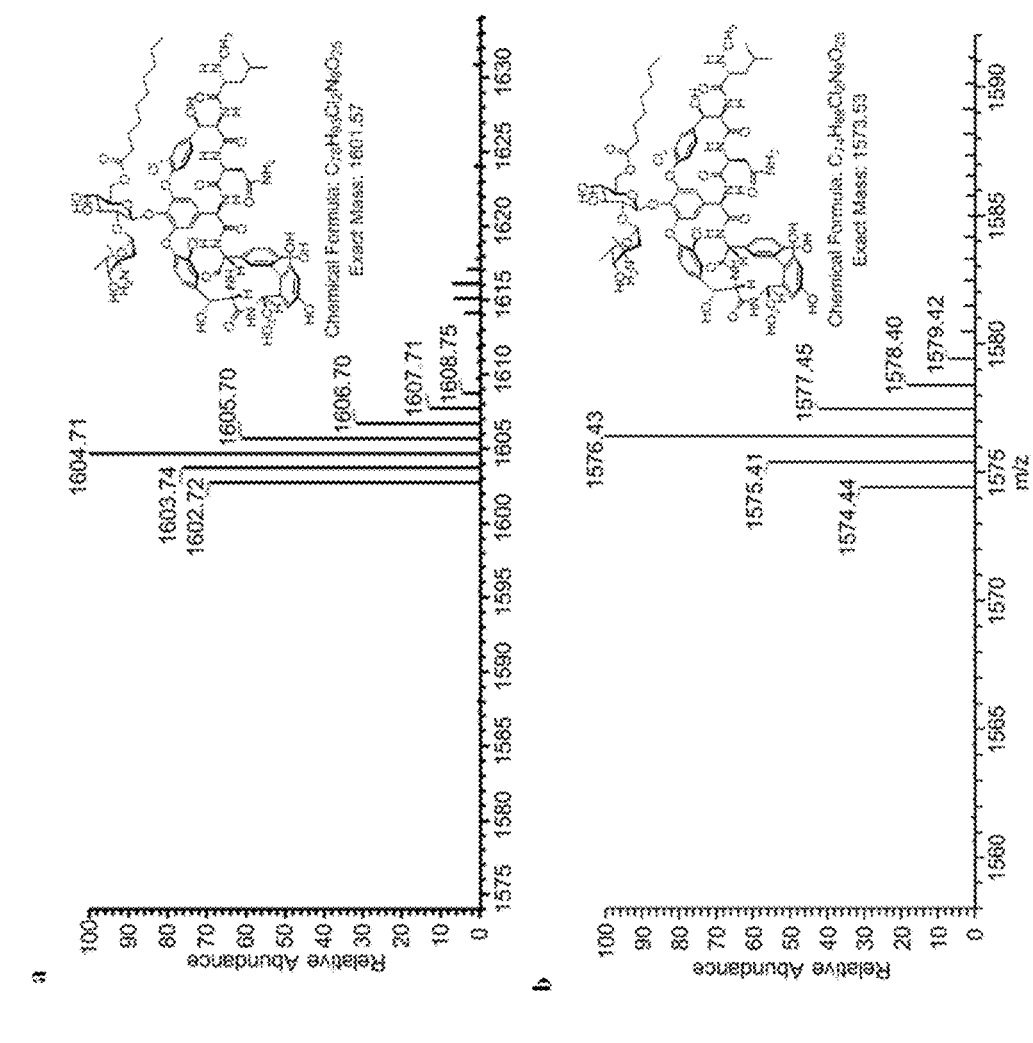
FIG. 11 shows the structures and mass spectra of (a) C10-vancomycin and (b) C8-vancomycin.
Figure 12:
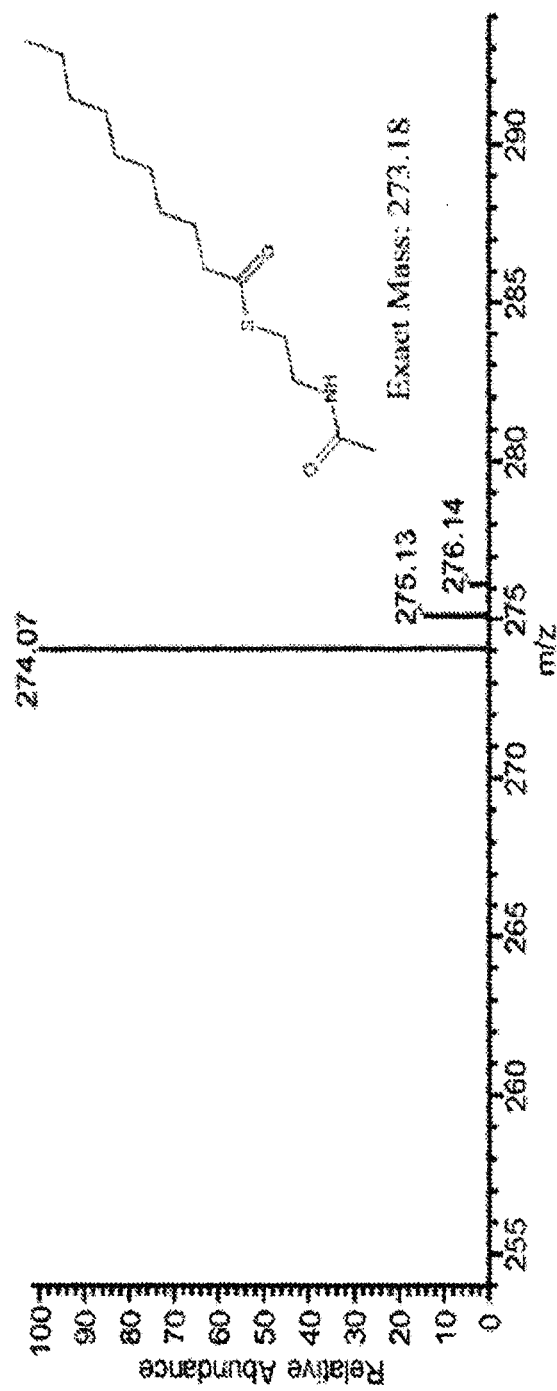
FIG. 12 shows the structure and mass spectrum of decanoyl-NAC.

Provided that the 4Hpg glucosamine is less constrained in the active site, vancomycin (Van) 6 (with a vancosamine-glucose disaccharide on 4Hpg) was interrogated for the acceptor tolerance. It turned out that the enzyme is capable of O-acylating Van at C-6 OH of glucose rather than C-3' $NH_2$ of vancosamine, as evidenced by NMR and MS analysis (7, FIG. 4a,b (trace x), FIG. 11). The acylation modification has in many cases been shown vital to valuable bioactivities of natural products (Nicolaou, K. C., Boddy, C. N., Brase, S. & Winssinger, N. Chemistry, Biology, and Medicine of the Glycopeptide Antibiotics. Angew Chem Int Ed Engl 38, 2096-2152 (1999); Kahne, D., Leimkuhler, C., Lu, W. & Walsh, C. Glycopeptide and lipoglycopeptide antibiotics. Chem Rev 105, 425-448, doi:10.1021/cr030103a (2005); Kruger, R. G. et al. Tailoring of glycopeptide scaffolds by the acyltransferases from the teicoplanin and A-40,926 biosynthetic operons. Chem Biol 12, 131-140, doi:10.1016/j.chembiol.2004.12.005 (2005)). It however would not be cost-effective if pricy CoA derivatives were used as acylating agents. An acyl-CoA mimic decanoyl-N-acetyl cysteamine (decanoyl-NAC 8, FIG. 12) was synthesized to test if the minimum element is sufficient to trigger protein conformational change so as to serve as an acyl donor. An enzymatic reaction with addition of Tei psudoaglycone 3 and decanoyl-NAC 8 was conducted. Clearly, emergence of a new peak with the same retention time and mass unit as those of Tei 1 (A2-3) on the LC trace confirmed that acyl-NAC can be an acyl-CoA surrogate (FIG. 4a,b, trace ix). The reaction efficiency was improved if free CoA was added.

Figure 13:
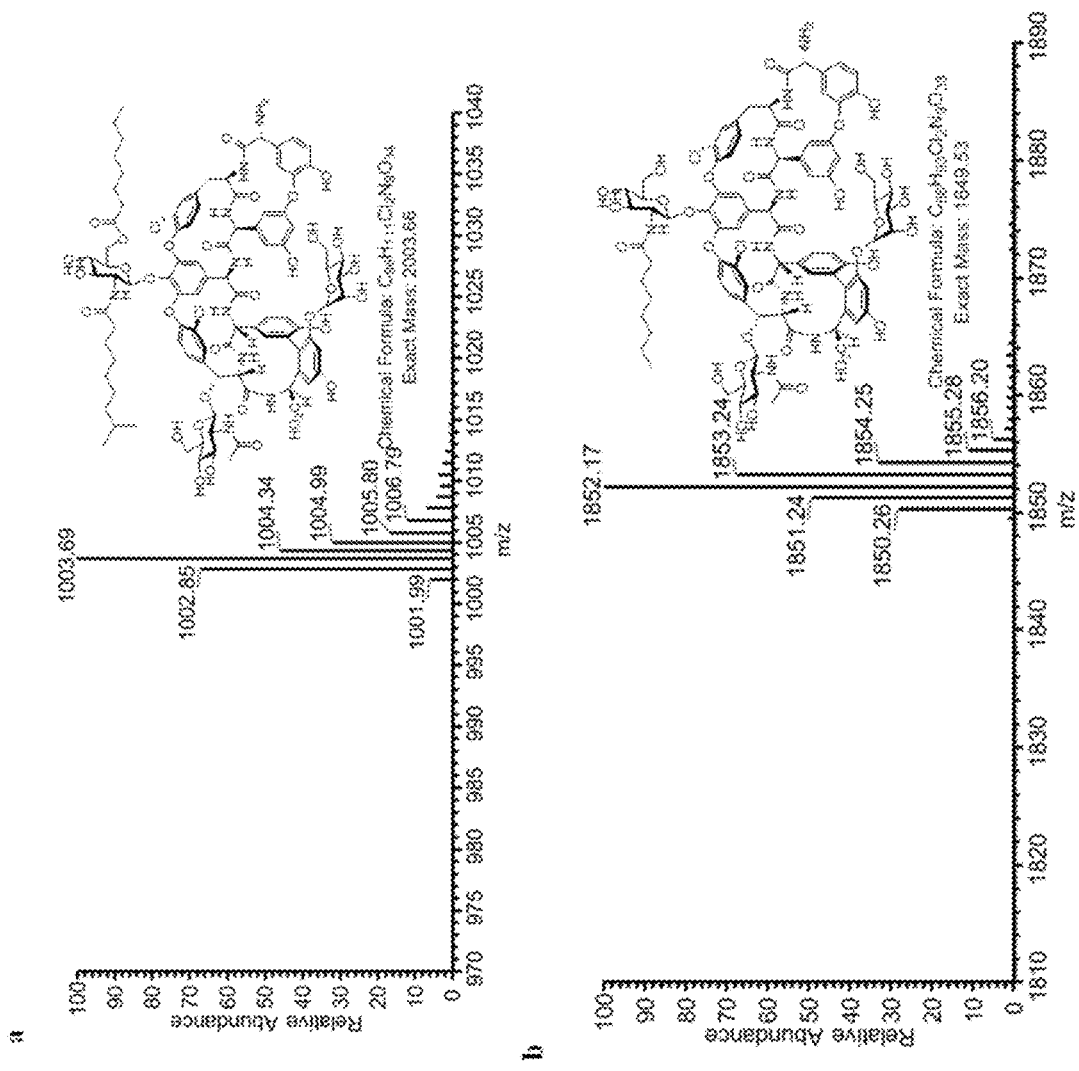
FIG. 13 shows the structures and mass spectra of (a) 2N-decanoyl, 6O-octyl-Tei and (b) octyl-Tei.
Figure 14:
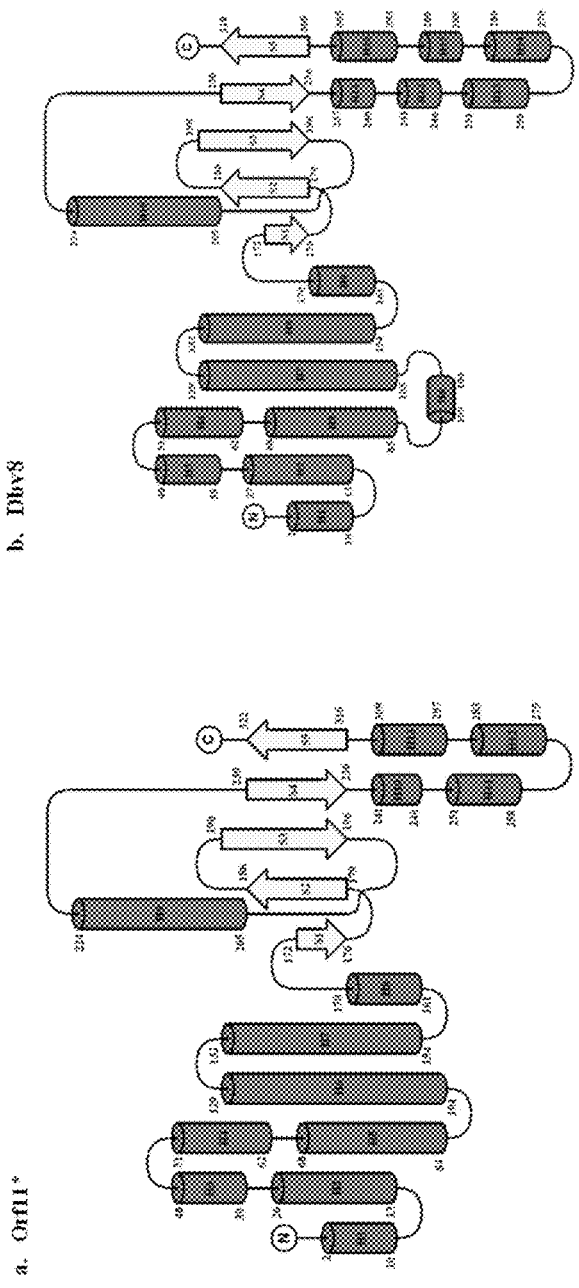
FIGS. 14a and 14b show schematic topologies of Orf11* and Dbv8. The topology diagrams were generated using TopDraw. The secondary structures of α-helix and β-sheet are shown, respectively. Orf11*/Dbv8 is composed of two domains, an N-terminal all-helix domain (residues 1-170) and a C-terminal GNAT domain (residues 171-322/residues 171-318 for Orf11*/Dbv8).
Figure 15:
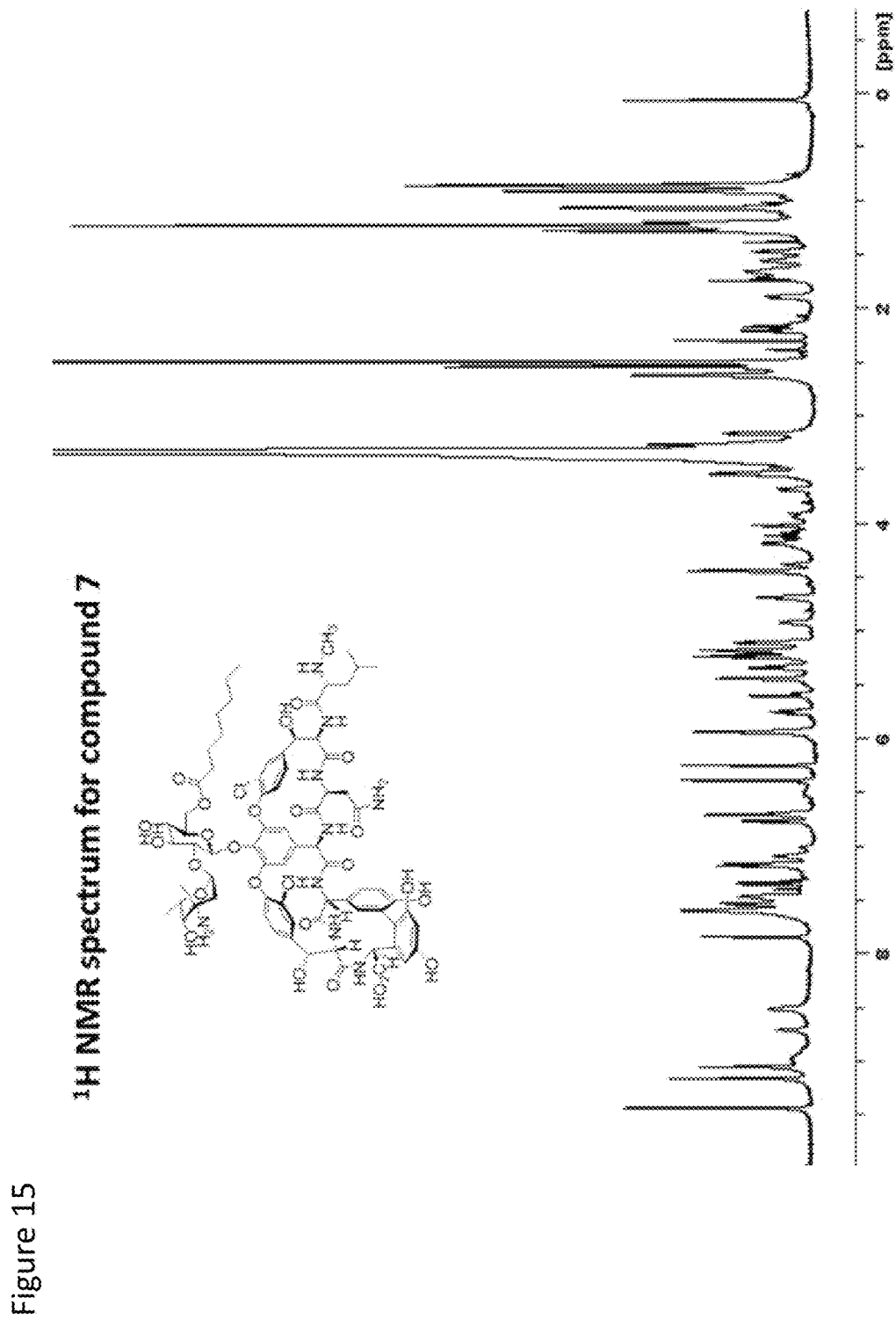
FIG. 15 shows NMR spectra include 1H, 13C, COSY, HSQC, HMBC, and NOESY of Compound 7.
Figure 15:
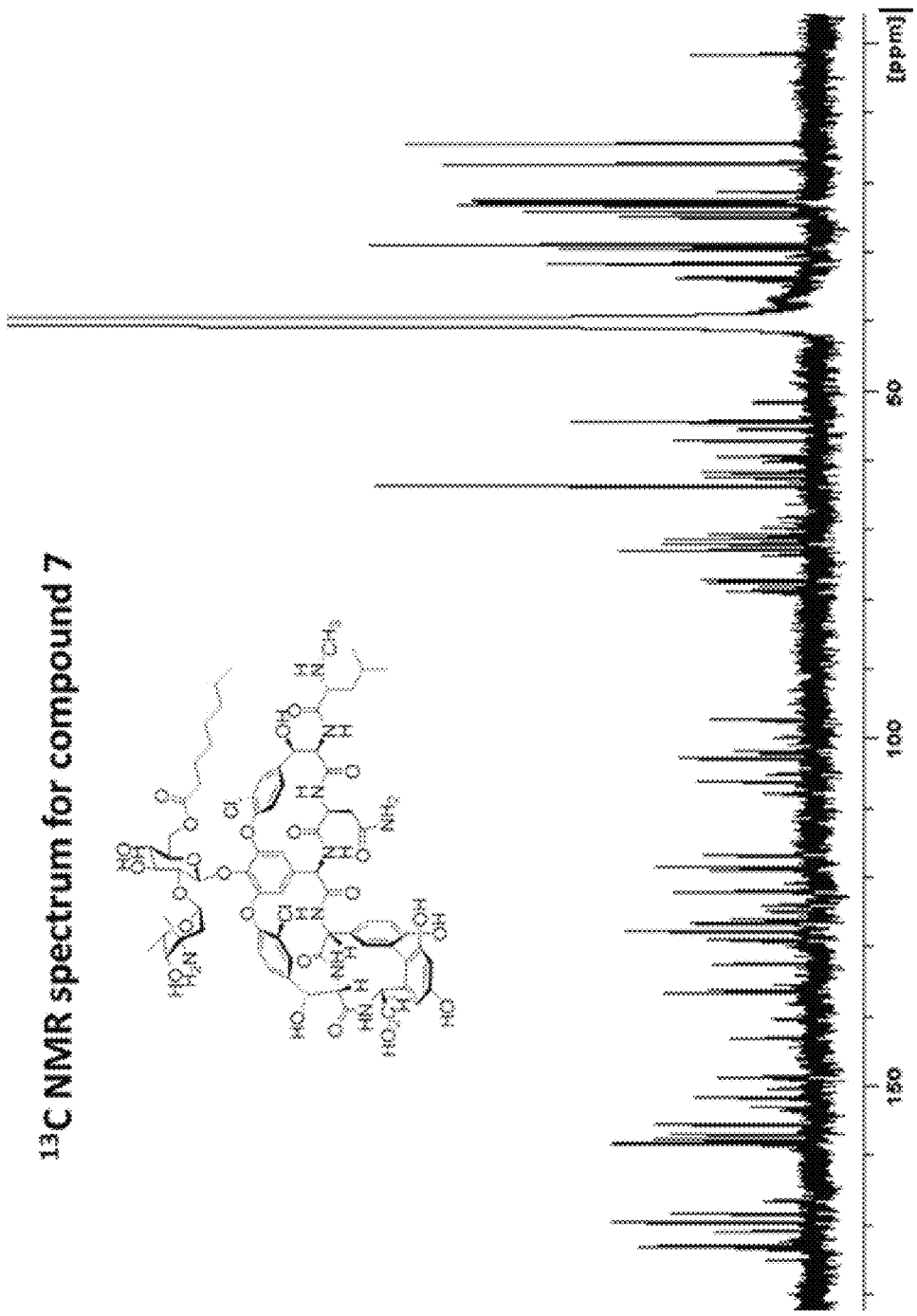
Figure 15:
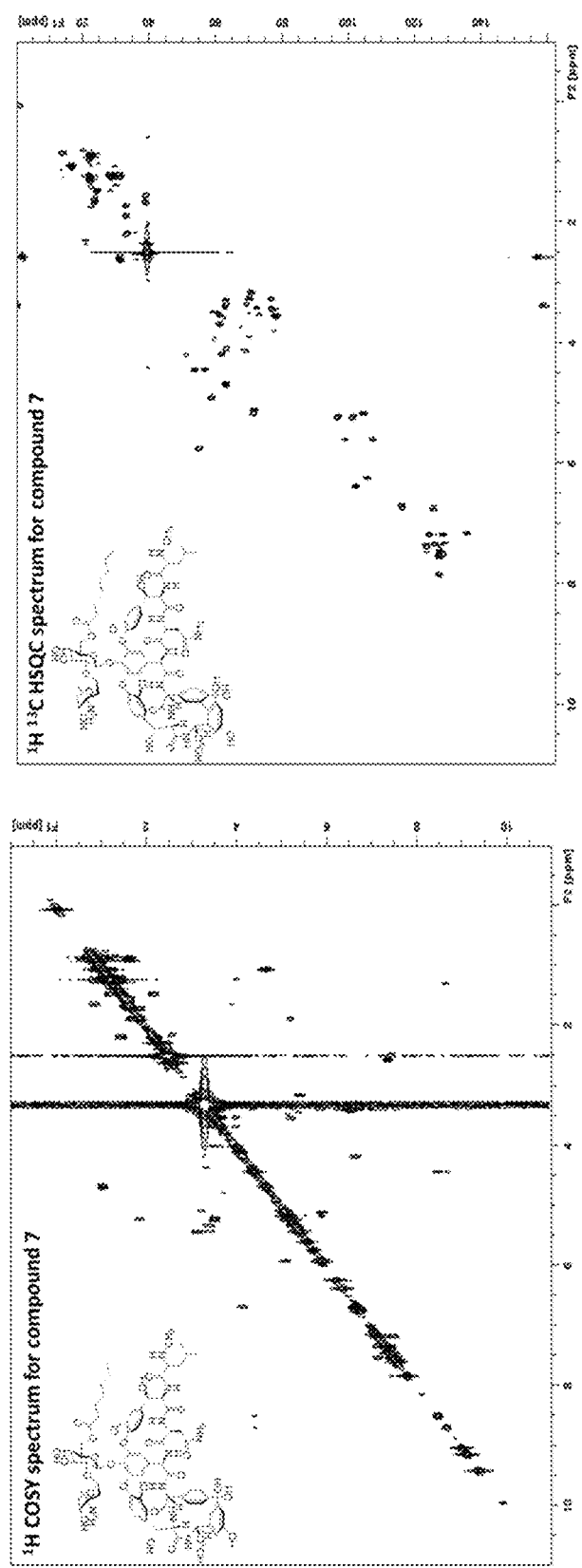
Figure 15:
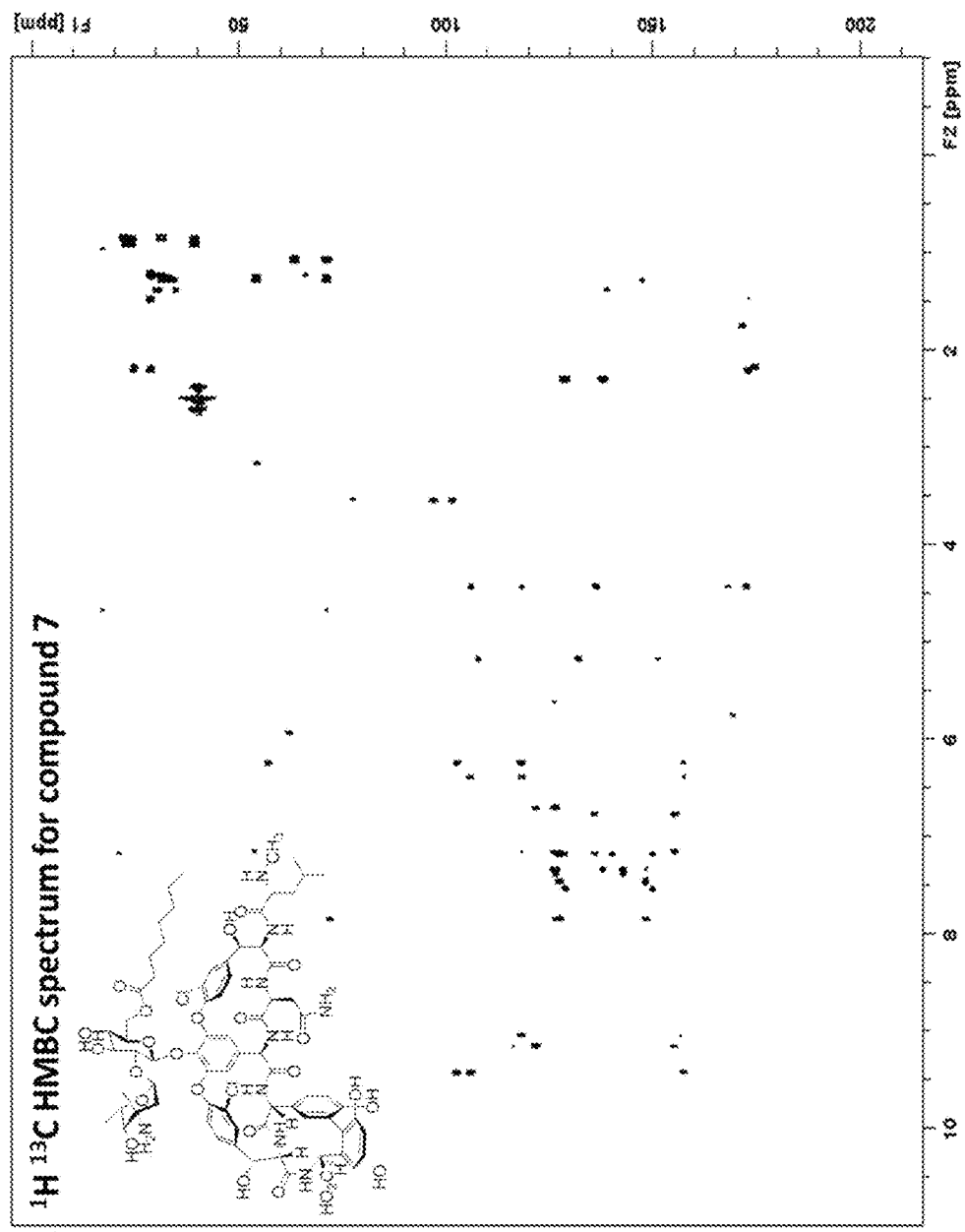
Figure 16:
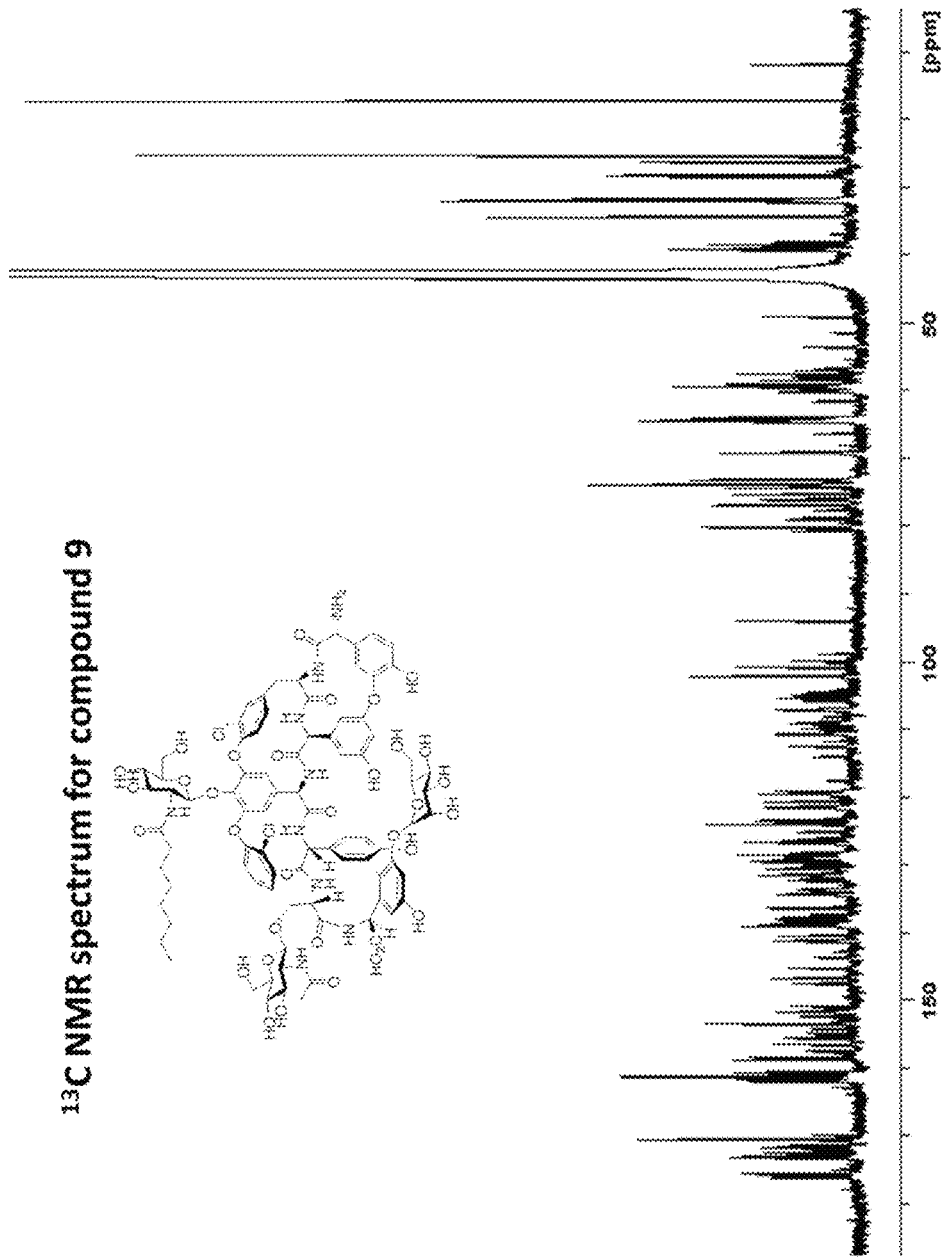
FIG. 16 shows NMR information for compound 9. NMR spectra include $^1$H, $^{13}$C, COSY, HSQC, HMBC, and NOESY.
Figure 16:
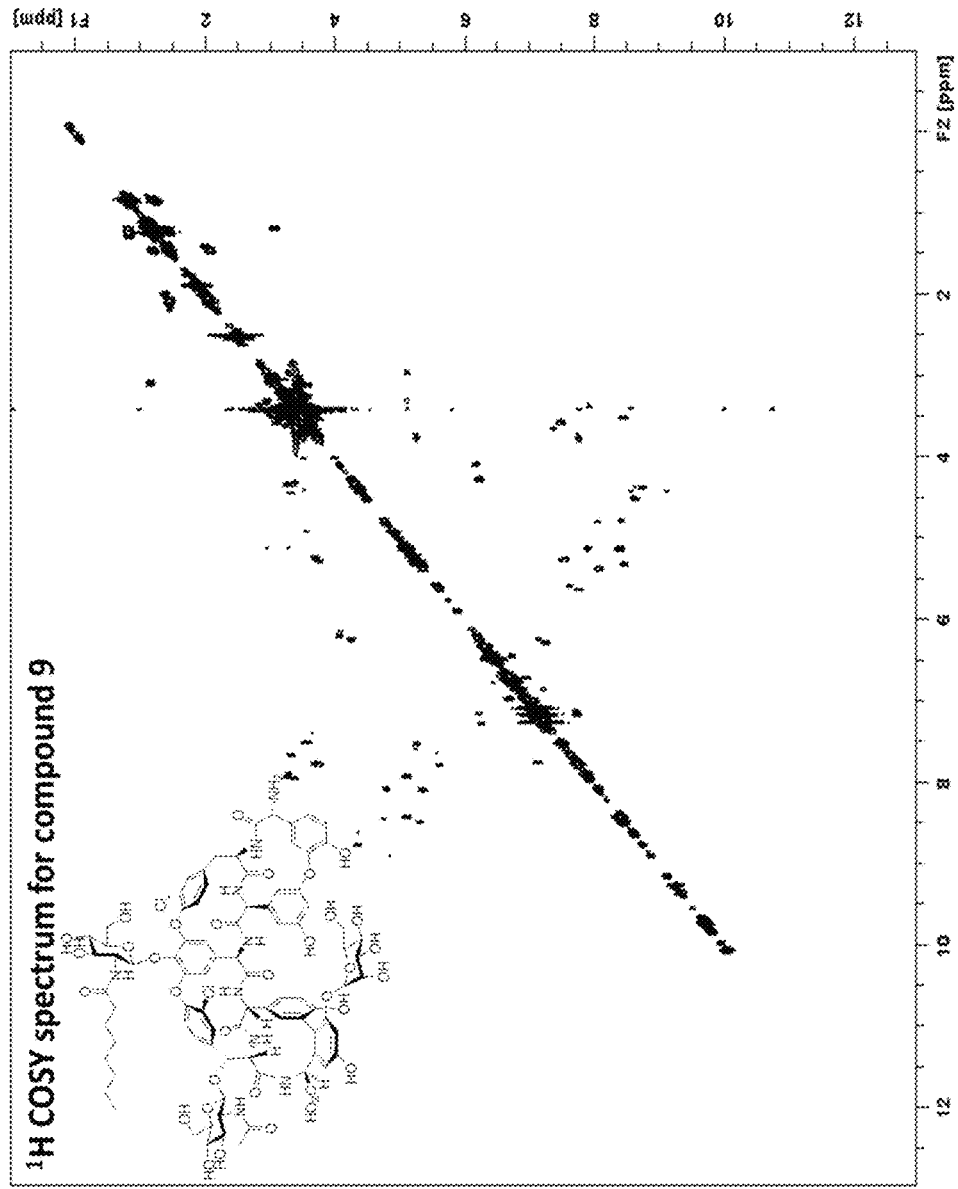
Figure 16:
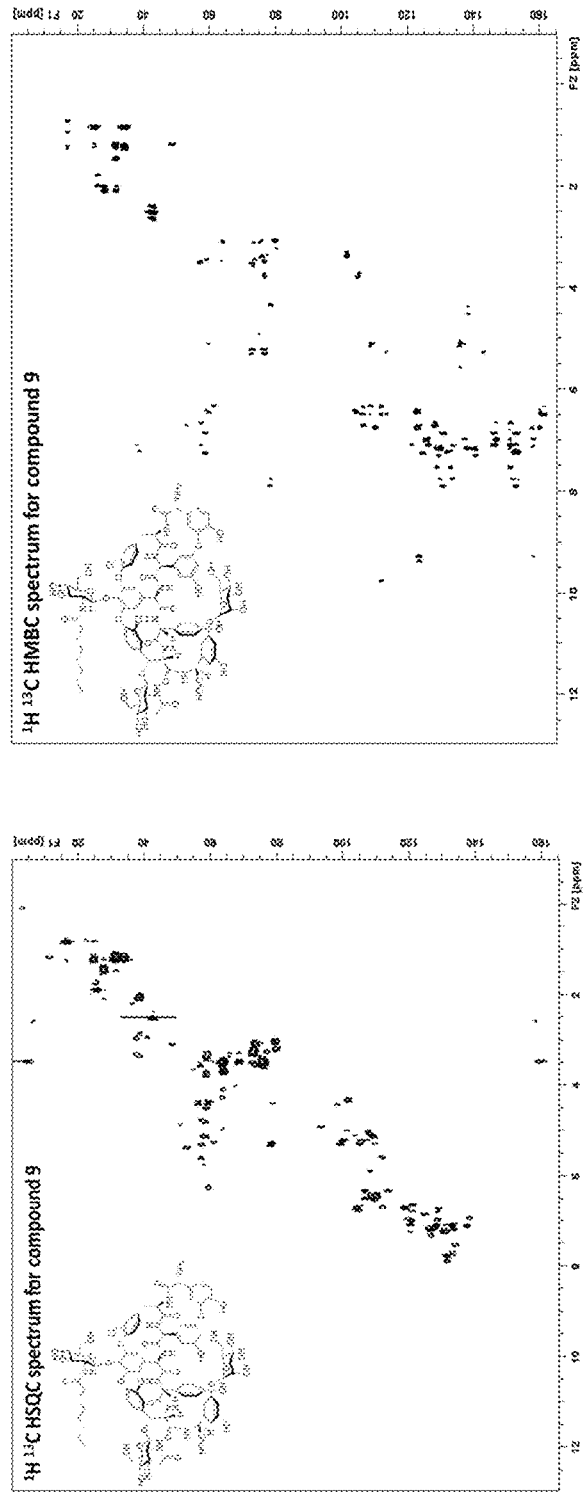
Figure 17:
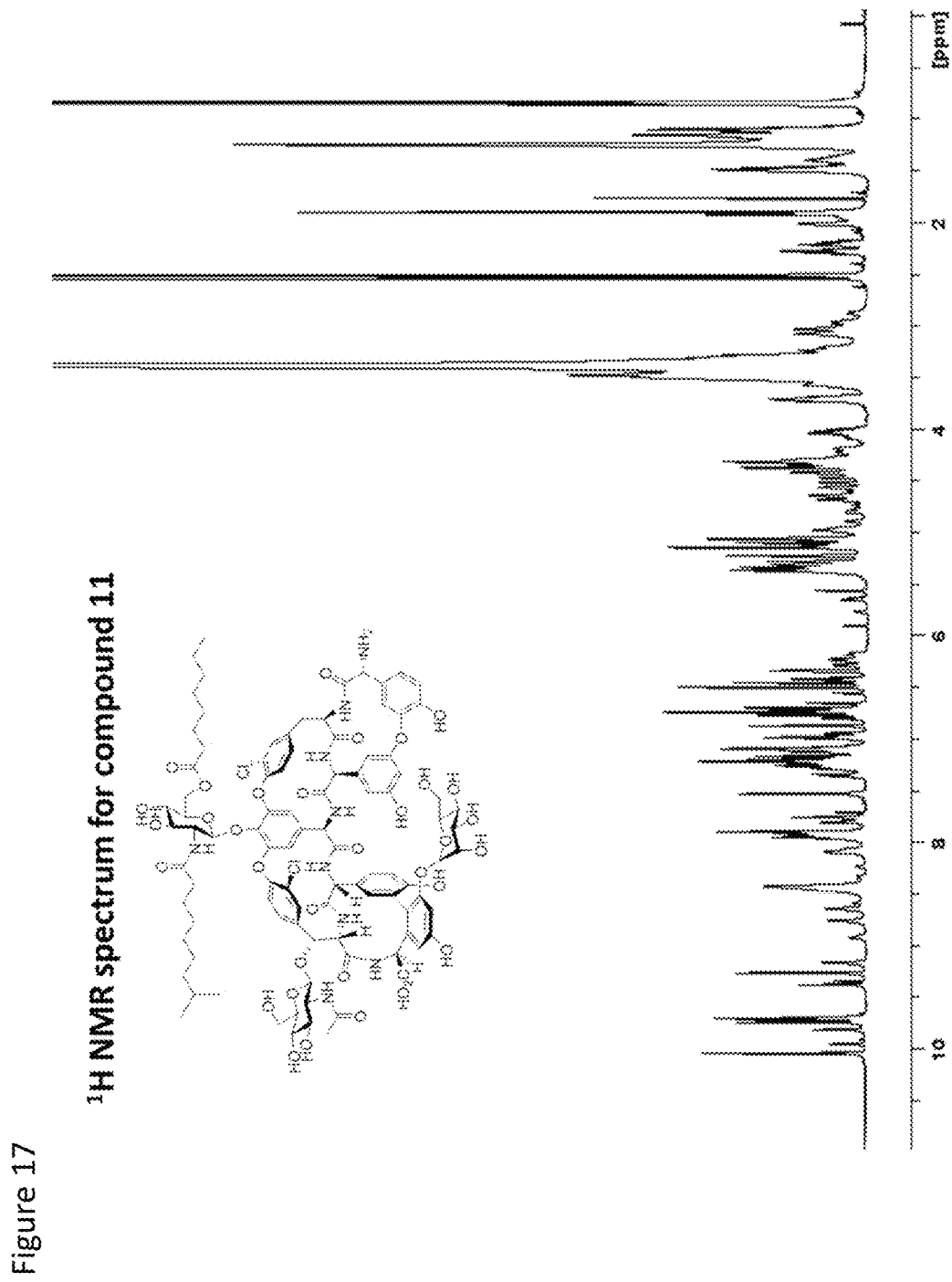
FIG. 17 shows NMR information for compound 11. NMR spectra include $^1$H, $^{13}$C, COSY, HSQC, HMBC, and NOESY.
Figure 17:
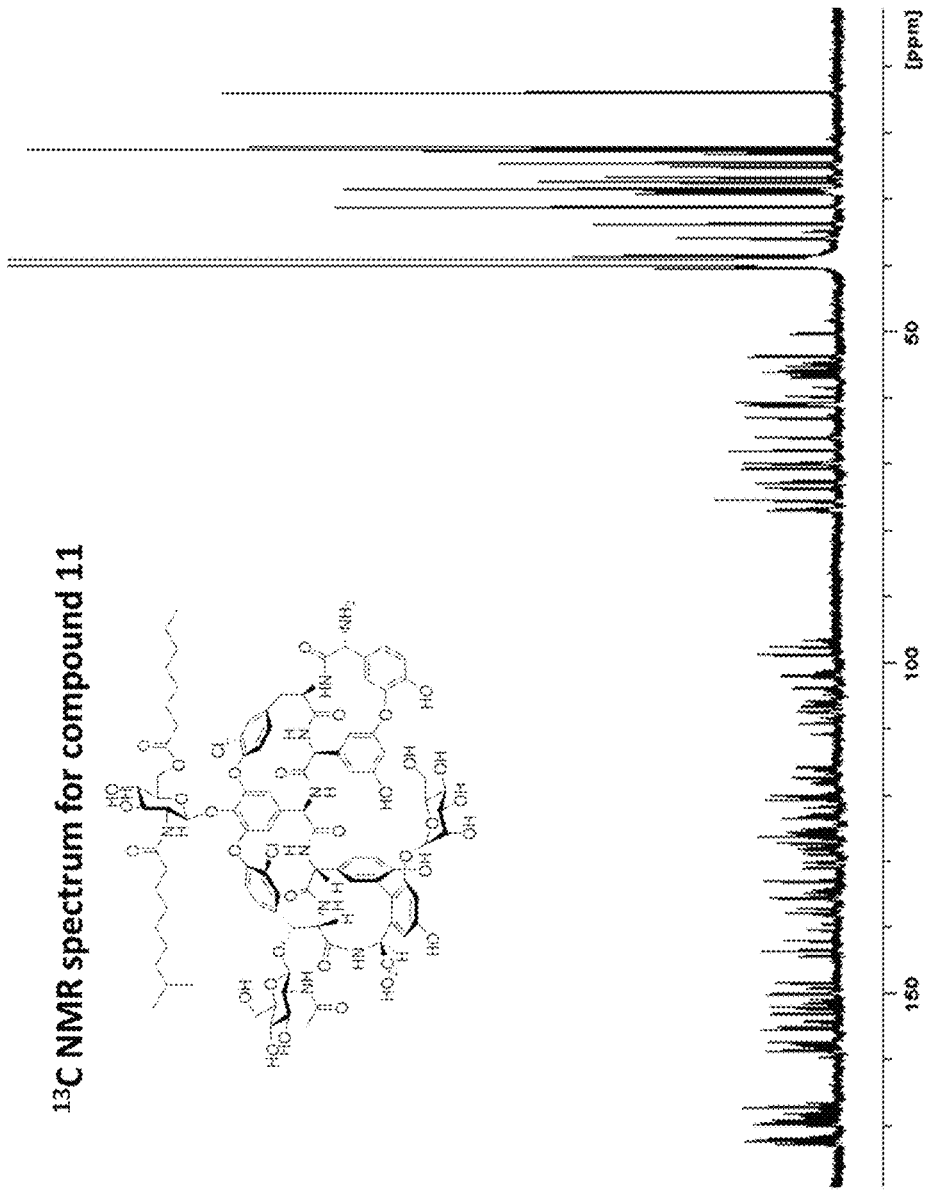
Figure 17:
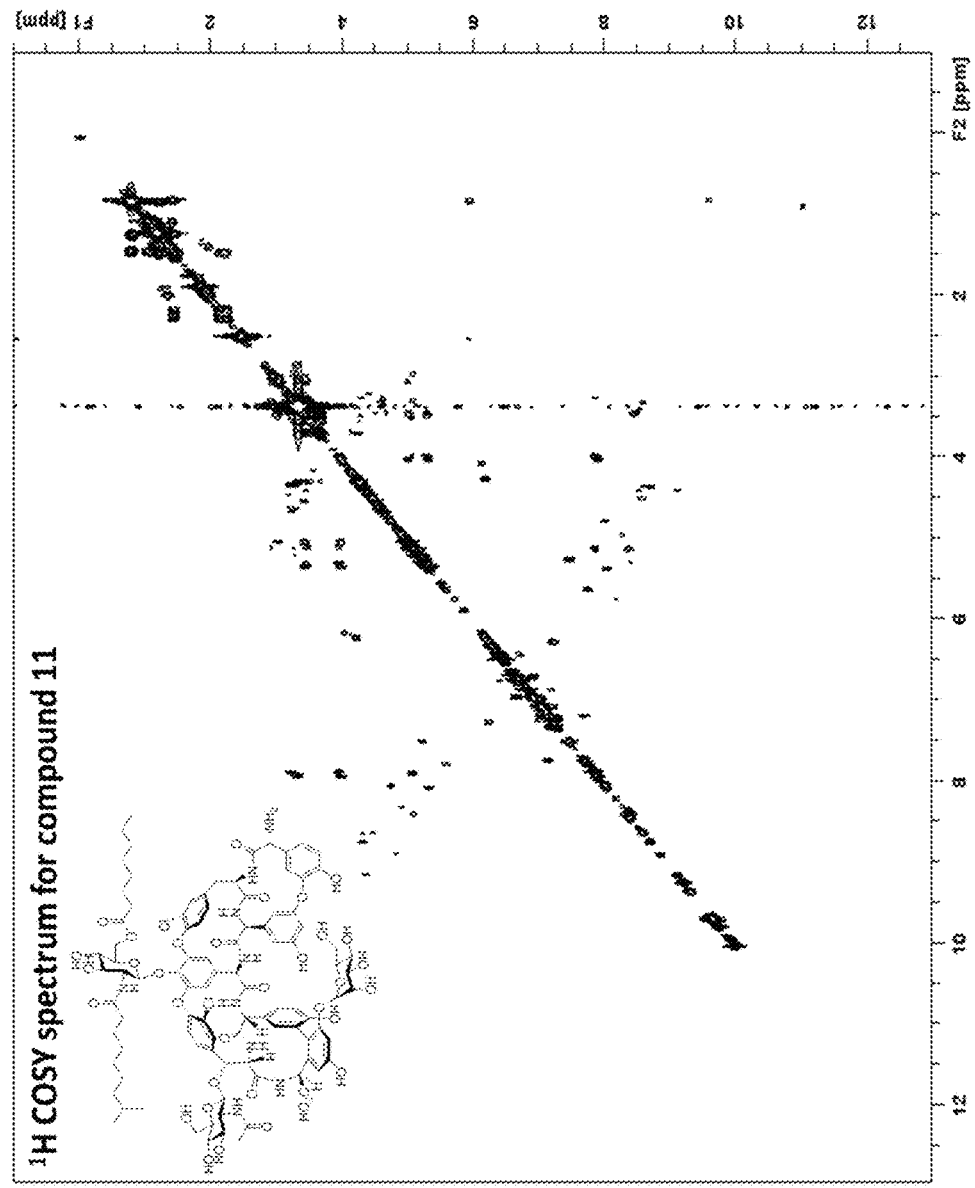
Figure 17:
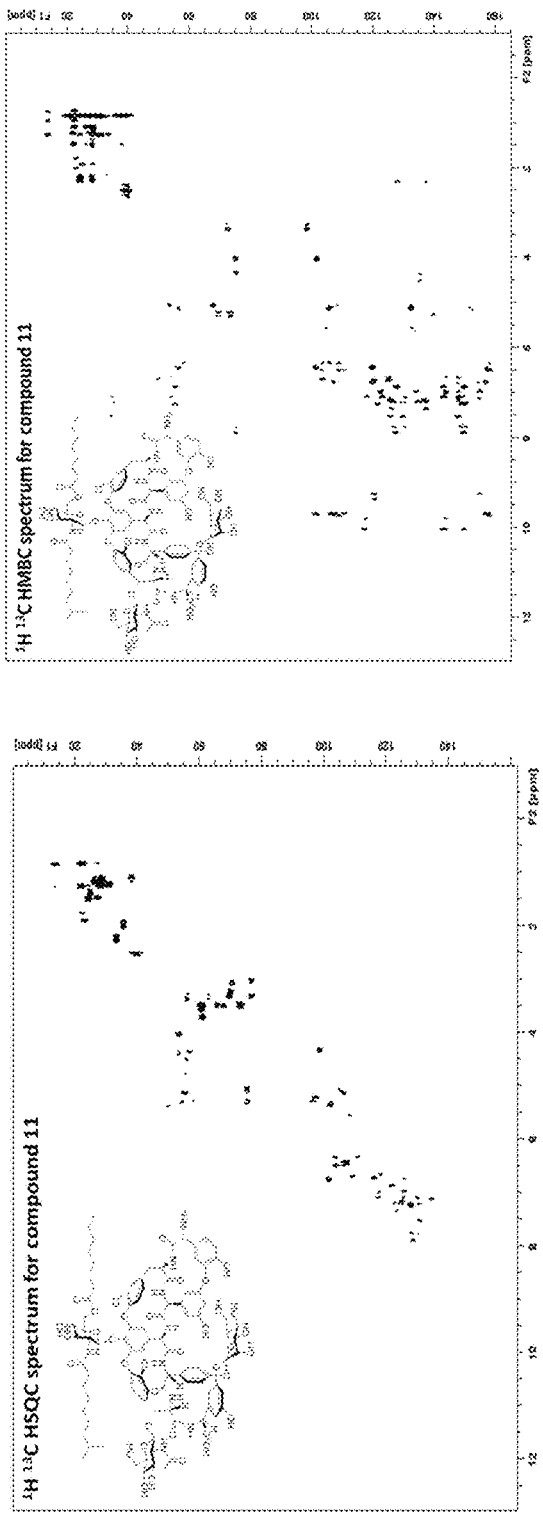
Figure 18:
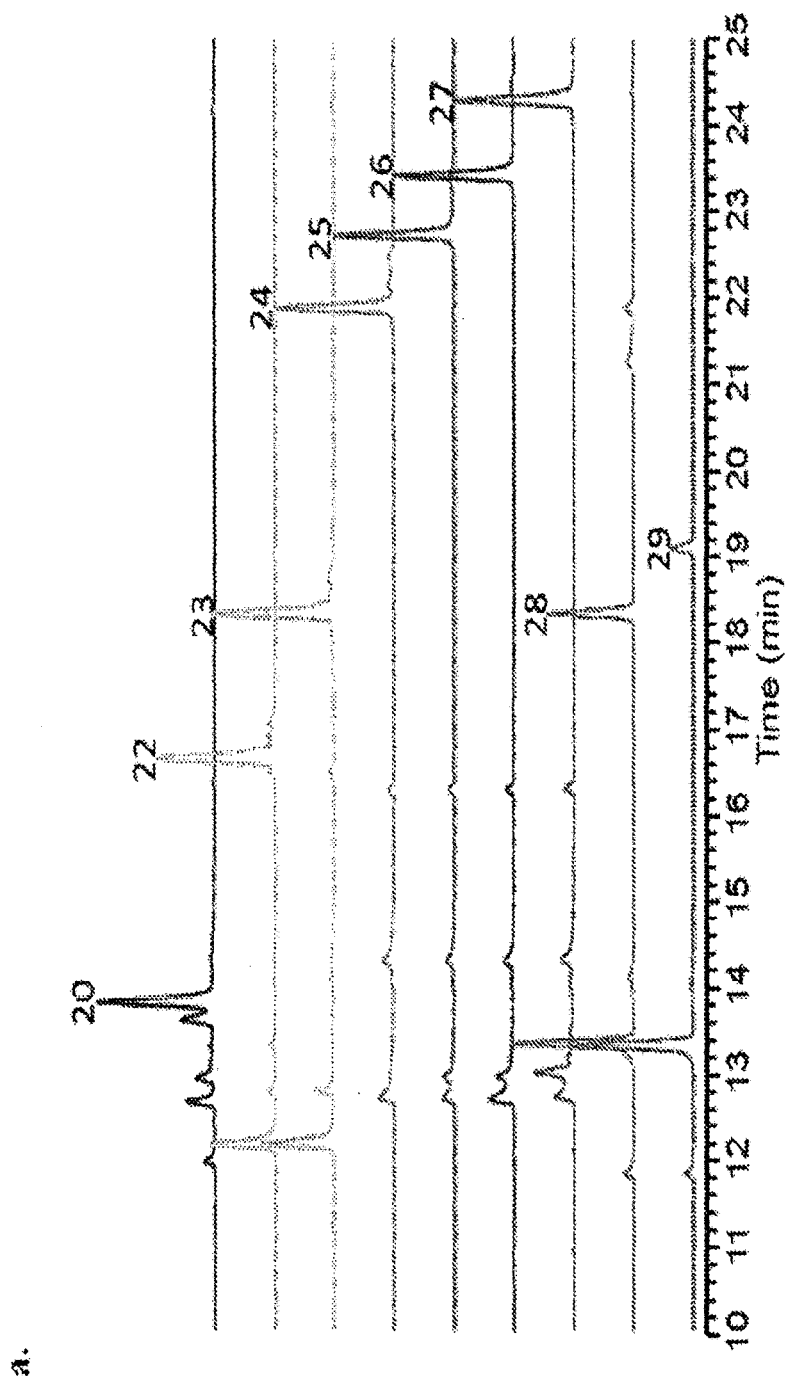
FIG. 18 shows the LC traces (a) and mass spectra (b-q) for major acylated Tei derivatives generated in the enzymatic reactions catalysed by Orf11*.
Figure 18:
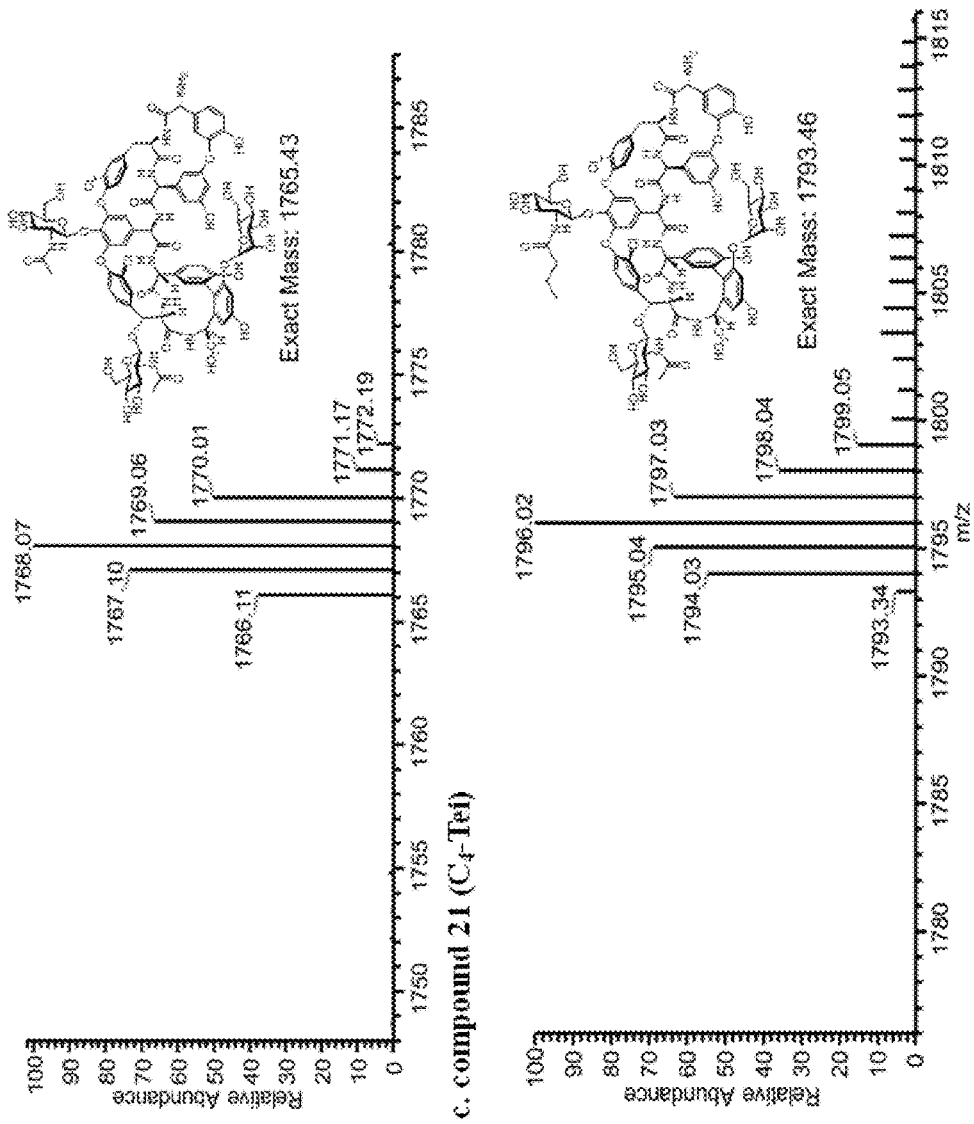
Figure 18:
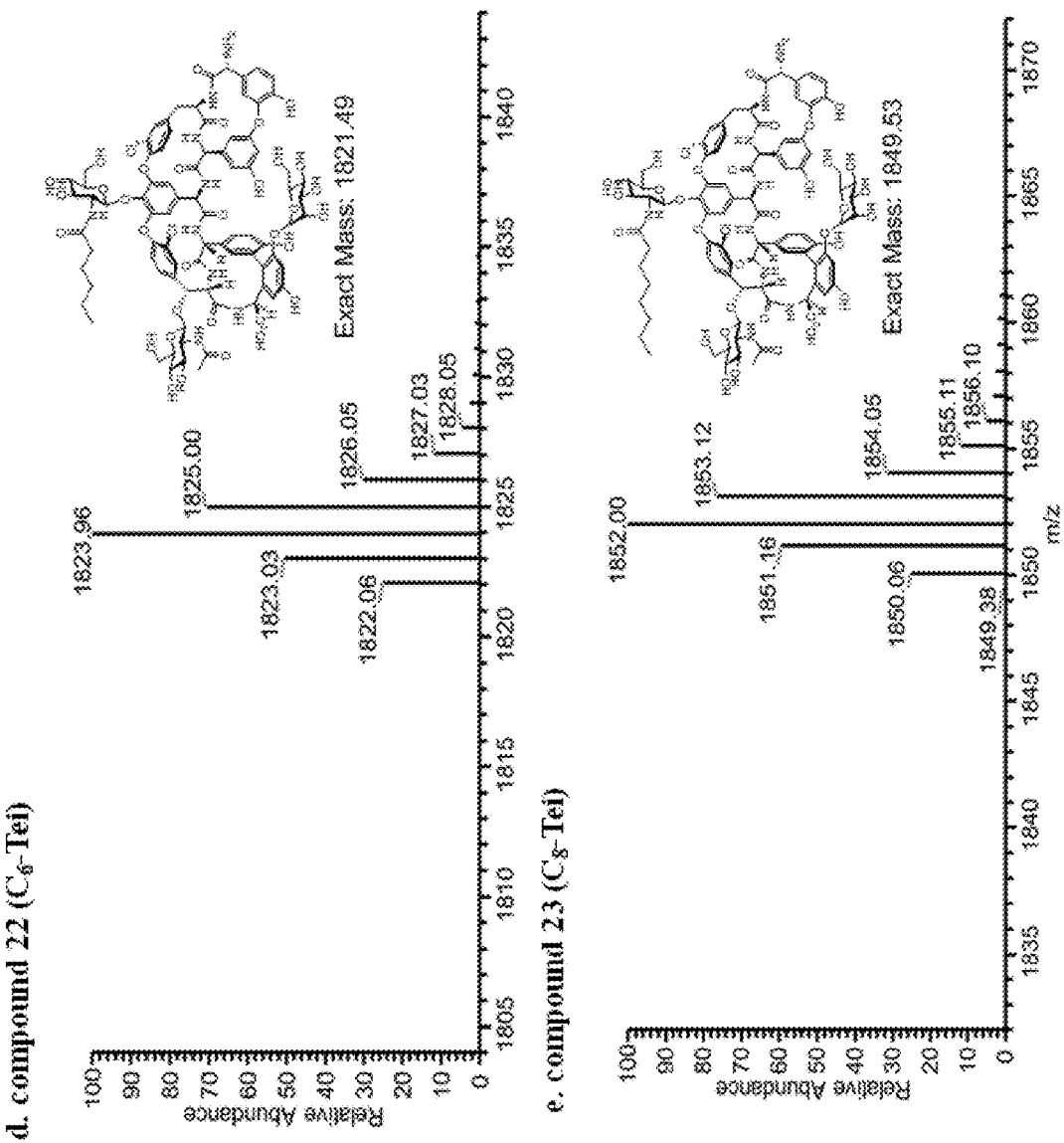
Figure 18:
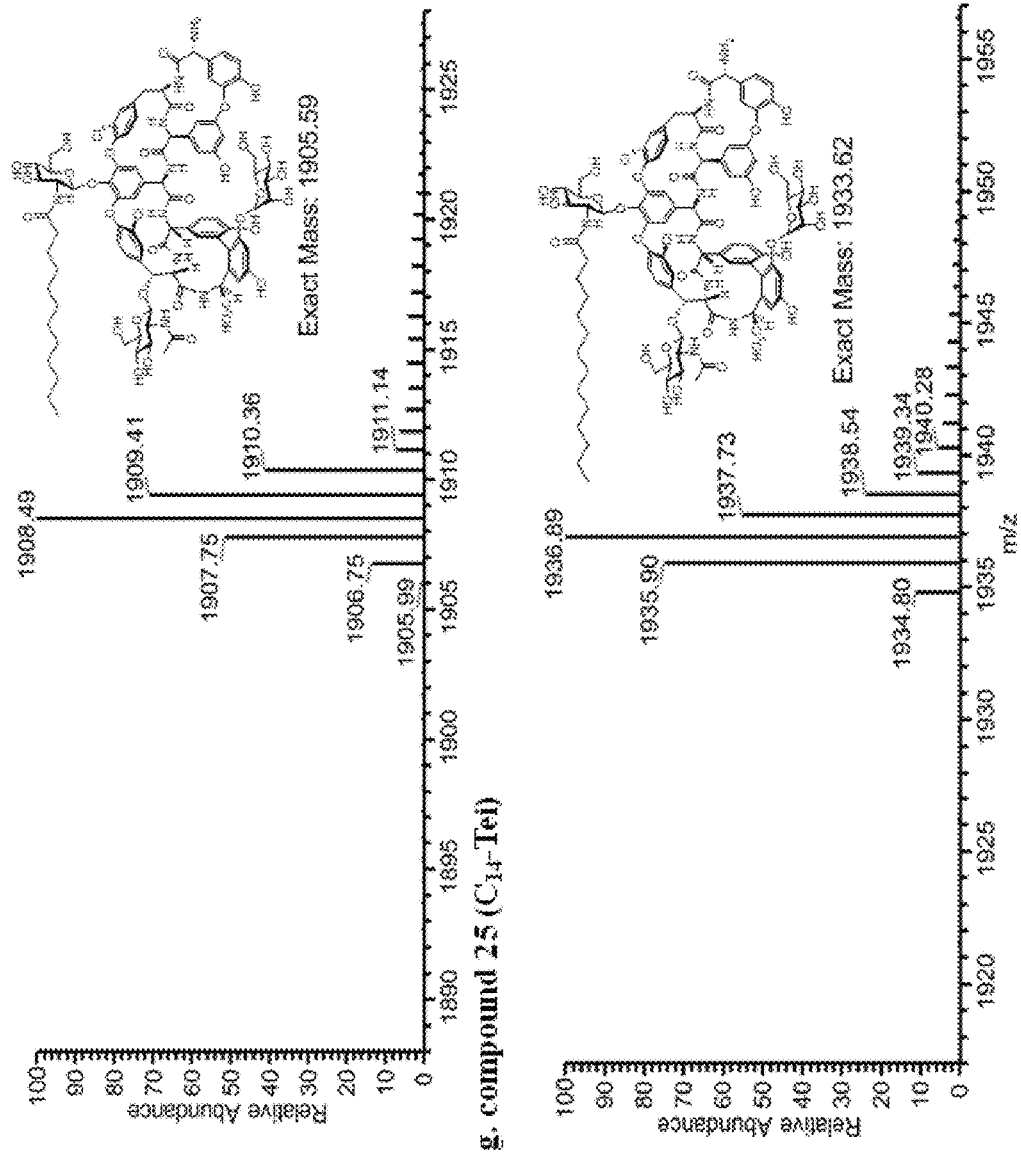
Figure 18:
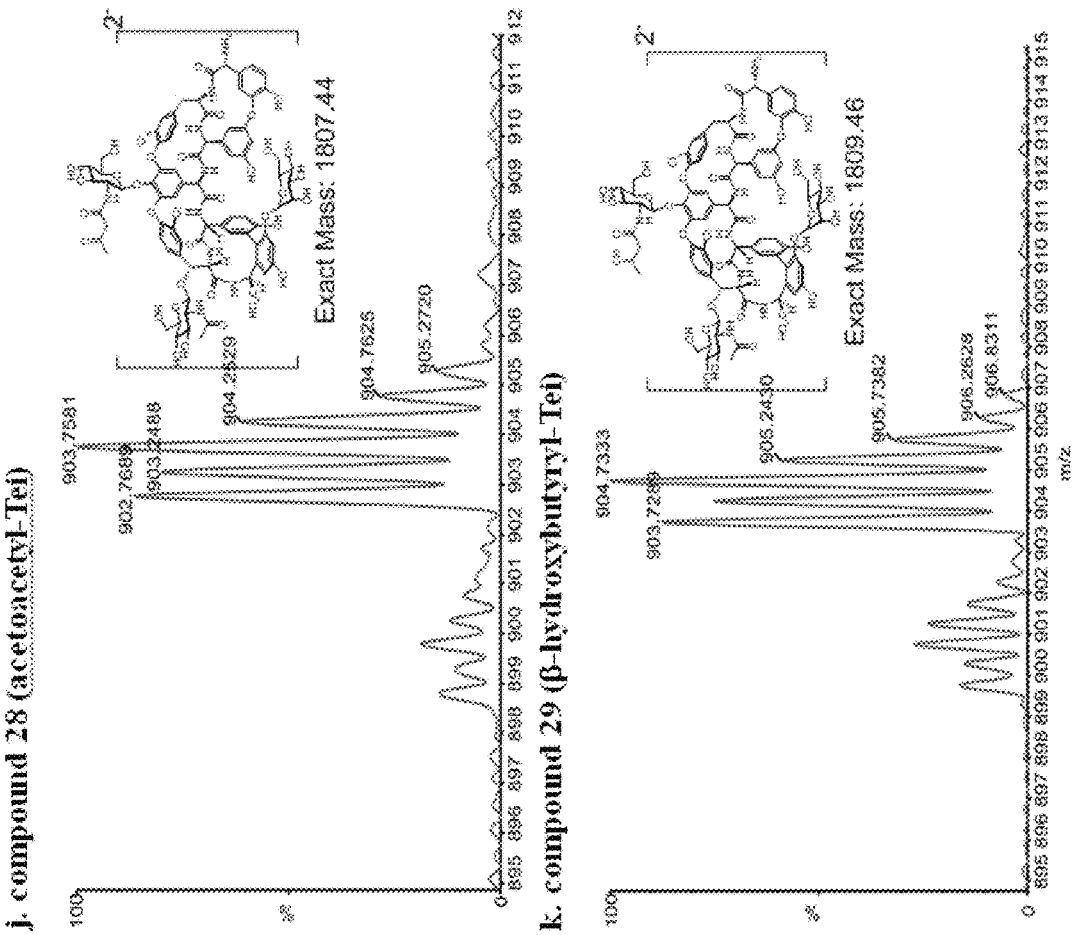
Figure 18:
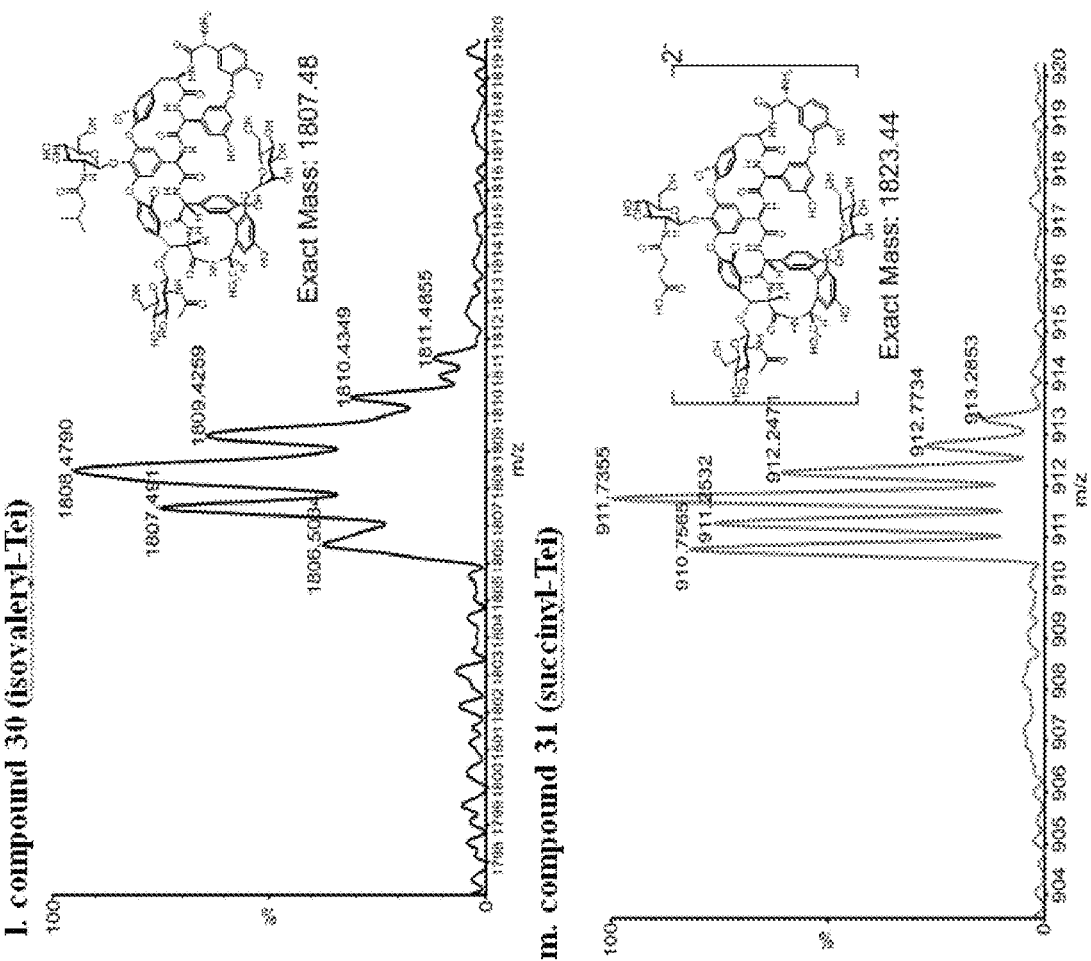
Figure 18:
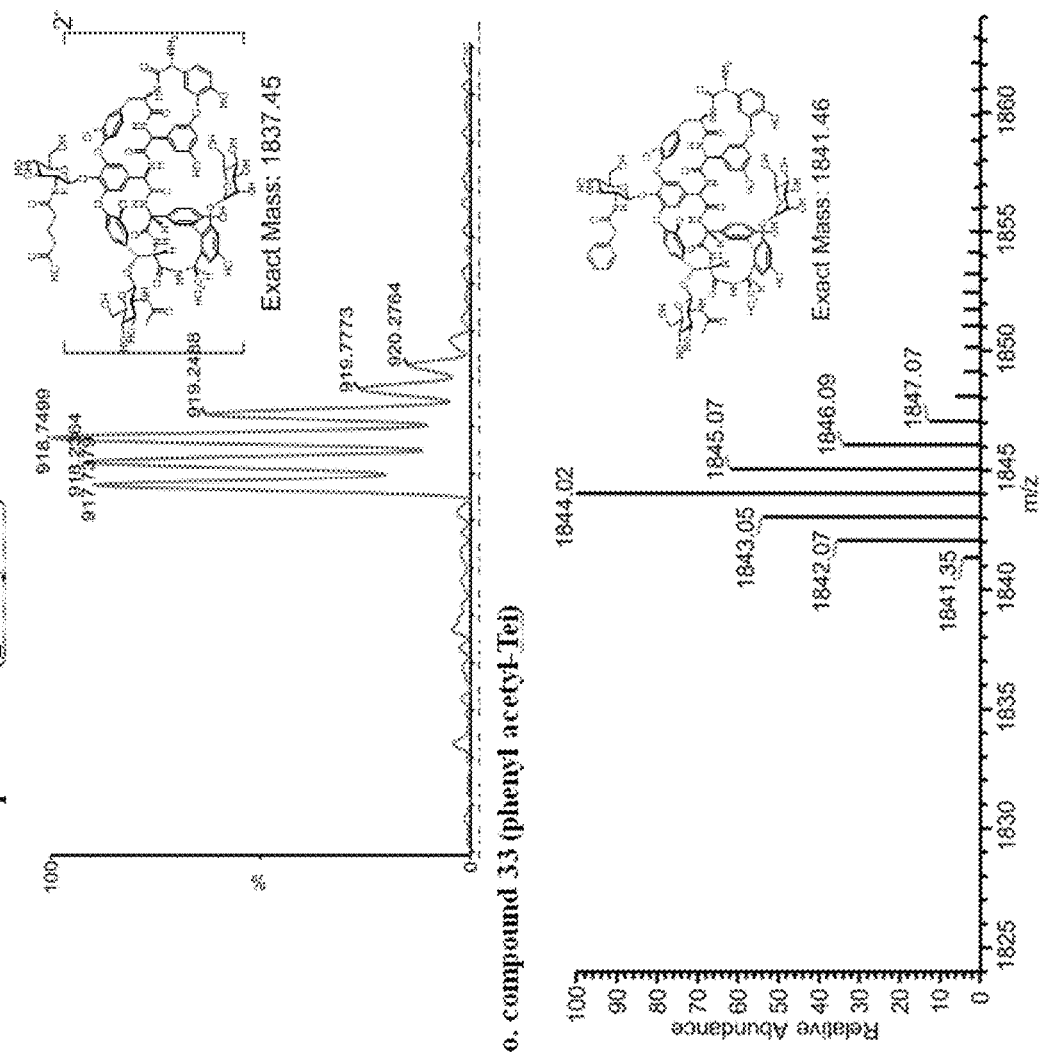
Figure 18:
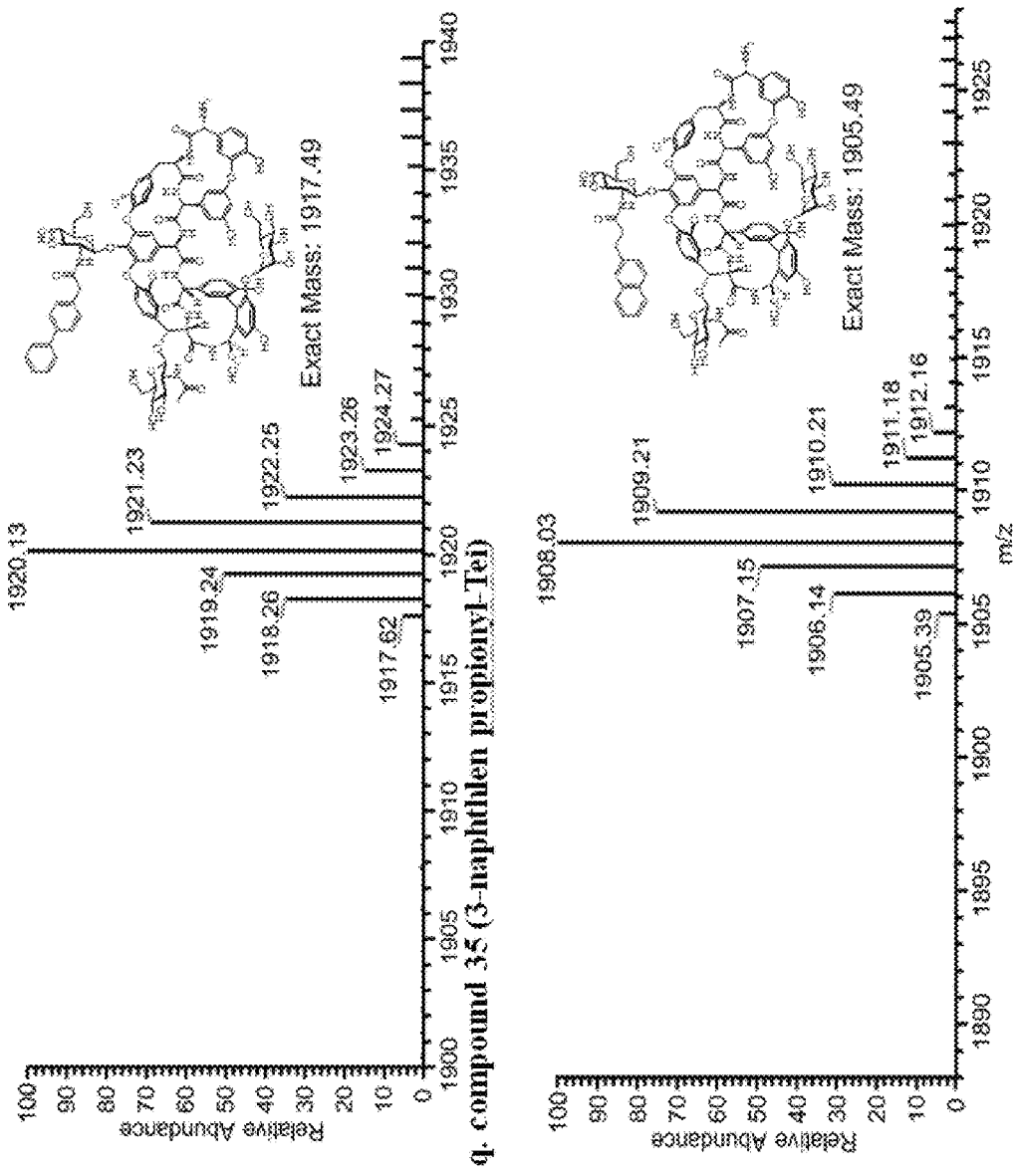
Figure 22:
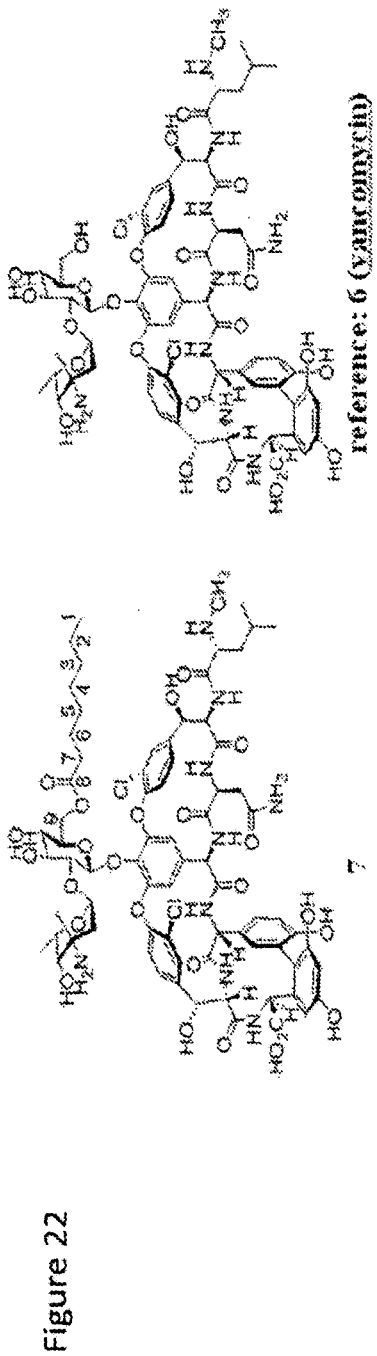
FIG. 22 shows Table 4: NMR assignments for compound 7.
Figure 23:
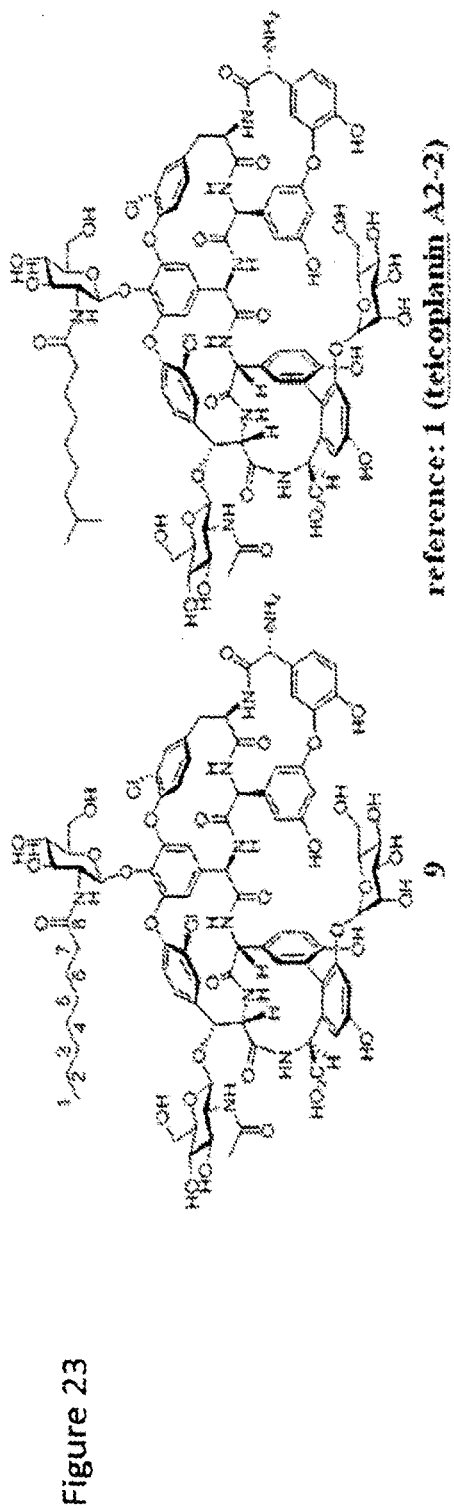
FIG. 23 shows Table 5: NMR assignments for compound 9.
Figure 24:
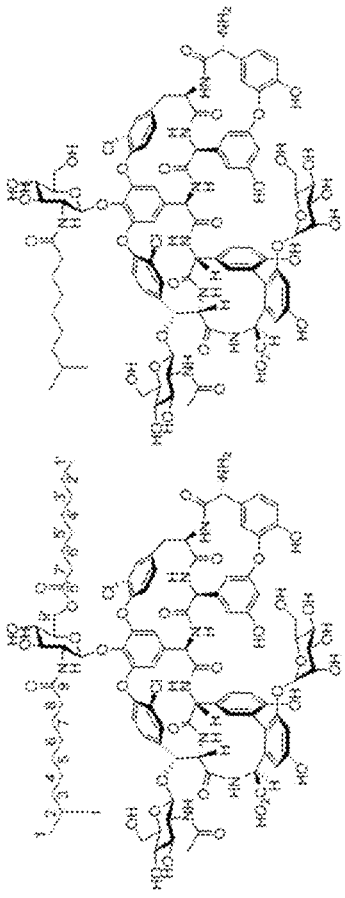
FIG. 24 shows Table 6: NMR assignments for compound 11.

It was reasoned that the acyl group is transferred from acyl-NAC to the free CoA through the transesterification reaction in the active site, whereof CoA turns its role from a substrate ligand to a cofactor. An enzyme-catalyzed acyl-swapping reaction was serendipitously discovered, as Tei 1 was converted to octyl-substituted Tei ($C_8$-Tei) 9 in an enzymatic reaction added with both Tei 1 and octyl-CoA 10 (FIG. 4a,b, trace xi). The same reaction was conducted at a higher pH (9.0) one new peak appeared on the LC trace, which was identified to be diacyl-Tei 11 ($C_8,C_{10}$-Tei), suggesting that it is likely the intermediate in the acyl-swapping reaction (FIG. 4a,b, trace xi). MS and NMR analysis confirmed that compound 11 is 2N-decanoyl, 6O-octyl-Tei (FIG. 13). It was reasoned that with the C-6 OH acylated the 4Hpg glucosamine would undergo an equatorial-axial interconversion via the twist-boat state owing to the active site constrains and/or intramolecular restrains. In a 1,4-diaxial fashion (the boat conformation) the C-2 secondary amine is able to attack the C-6 ester to form a germinal diacyl transition, of which the C-6 ester likely remains headlong into the lipid tunnel, so loss of the solvent-exposed acyl group results in acyl-swapped Tei (FIG. 3b). To verify this proposition we examined acyl-Van 7, from which no new product was formed suggesting that the swapping reaction likely follows the intramolecular hexose-chair-flipping mechanism. This finding affords an expedient way to generate new Tei analogs without problematic de-acylation and re-acylation processes (Chan, H. C. et al. Regioselective deacetylation based on teicoplanin-complexed Orf2* crystal structures. Mol Biosyst 7, 1224-1231, doi:10.1039/cOmb00320d (2011); Liu, Y. C. et al. Interception of teicoplanin oxidation intermediates yields new antimicrobial scaffolds. Nat Chem Biol 7, 304-309, doi:10.1038/nchembio.556 (2011); Li, T. L., Liu, Y. C. & Lyu, S. Y. Combining biocatalysis and chemo-selective chemistries for glycopeptide antibiotics modification. Curr Opin Chem Biol 16, 170-178, doi:10.1016/j.cbpa.2012.01.017 (2012)). This finding also provides a one-pot solution to convert Tei mixtures (A2-1 to A2-5 and RS1 to RS4 etc.) (Li, T. L. et al. Biosynthetic gene cluster of the glycopeptide antibiotic teicoplanin: characterization of two glycosyltransferases and the key acyltransferase. Chem Biol 11, 107-119, doi: 10.1016/j.chembiol.2004.01.001 (2004)) of natural isolates to a single uniform compound, which might facilitate the development of approvable drugs (teicoplanin is not approved by US-FDA due to the nature of mixtures, FIG. 4a traces v,ix) (Svetitsky, S., Leibovici, L. & Paul, M. Comparative Efficacy and Safety of Vancomycin versus Teicoplanin: Systematic Review and Meta-Analysis. Antimicrob Agents Ch 53, 4069-4079, doi:Doi 10.1128/Aac.00341-09 (2009)).

Figure 5:
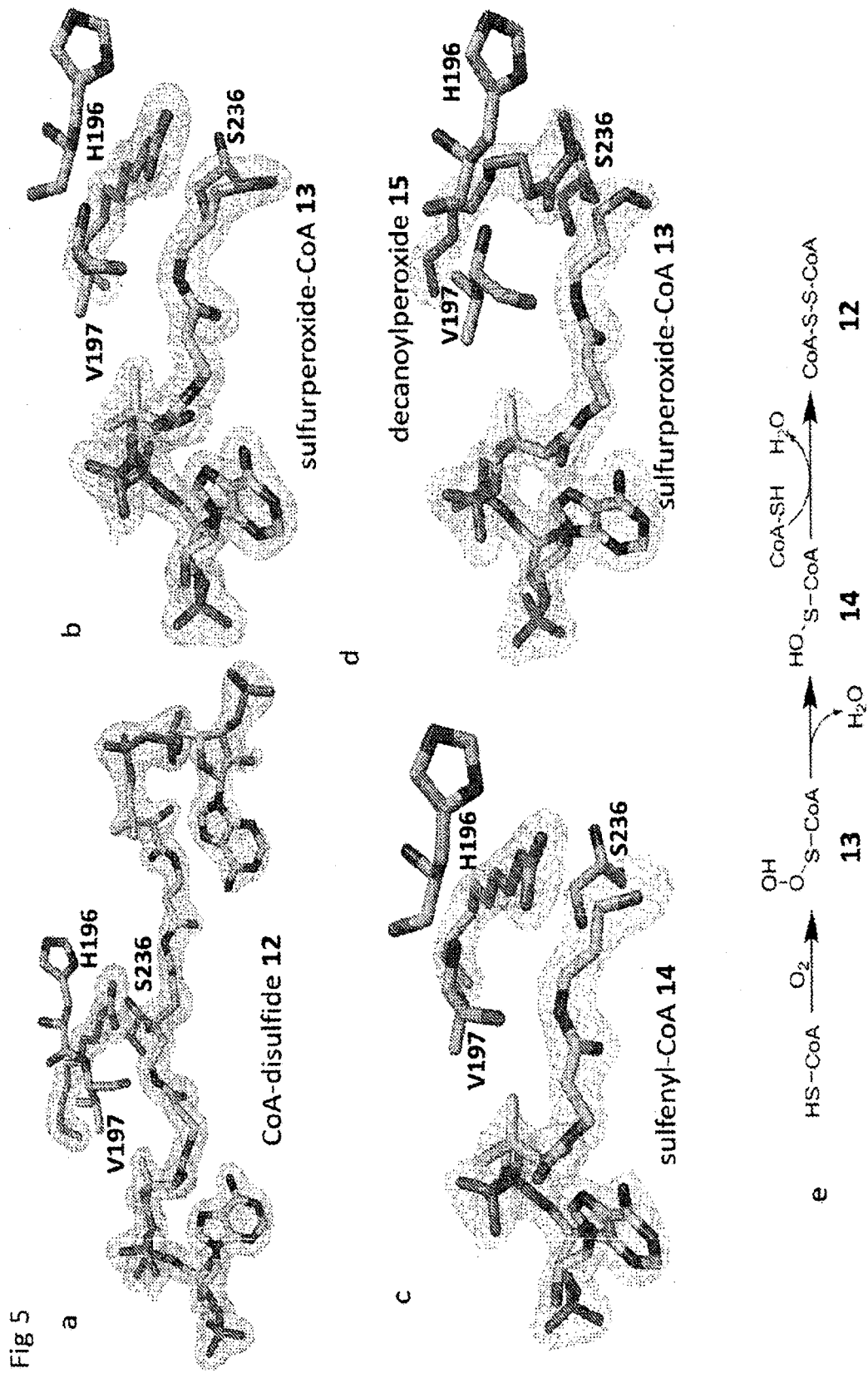
FIG. 5 shows structures of oxidation products in the active site of Orf11* and their proposed mechanisms. (a) The structure of CoA-disulfide 12. (b) The structure of sulfurperoxide-CoA 13. (c) The structure of sulfenyl-CoA 14. (d) The structure of decanoylperoxide 15. (e) The proposed mechanism for CoA oxidation. (f) The structure of decanoylperoxide-CoA 16. (g) The proposed mechanism for the formation of decanoylperoxide-CoA 16 and decanoylperoxide 15. (h) The structures of (1R)-octanol peroxide-CoA 18 and α/β-D-glucose. (i) The structure of octylperoxide-CoA 19. (j) The proposed peroxide-CoA mediated oxidation mechanism for β-OG via (1R)-octanol peroxide-CoA 18 to octylperoxide-CoA 19. The $2F_o-F_c$ electron density maps are contoured at 1.5 σ.
Figure 5:
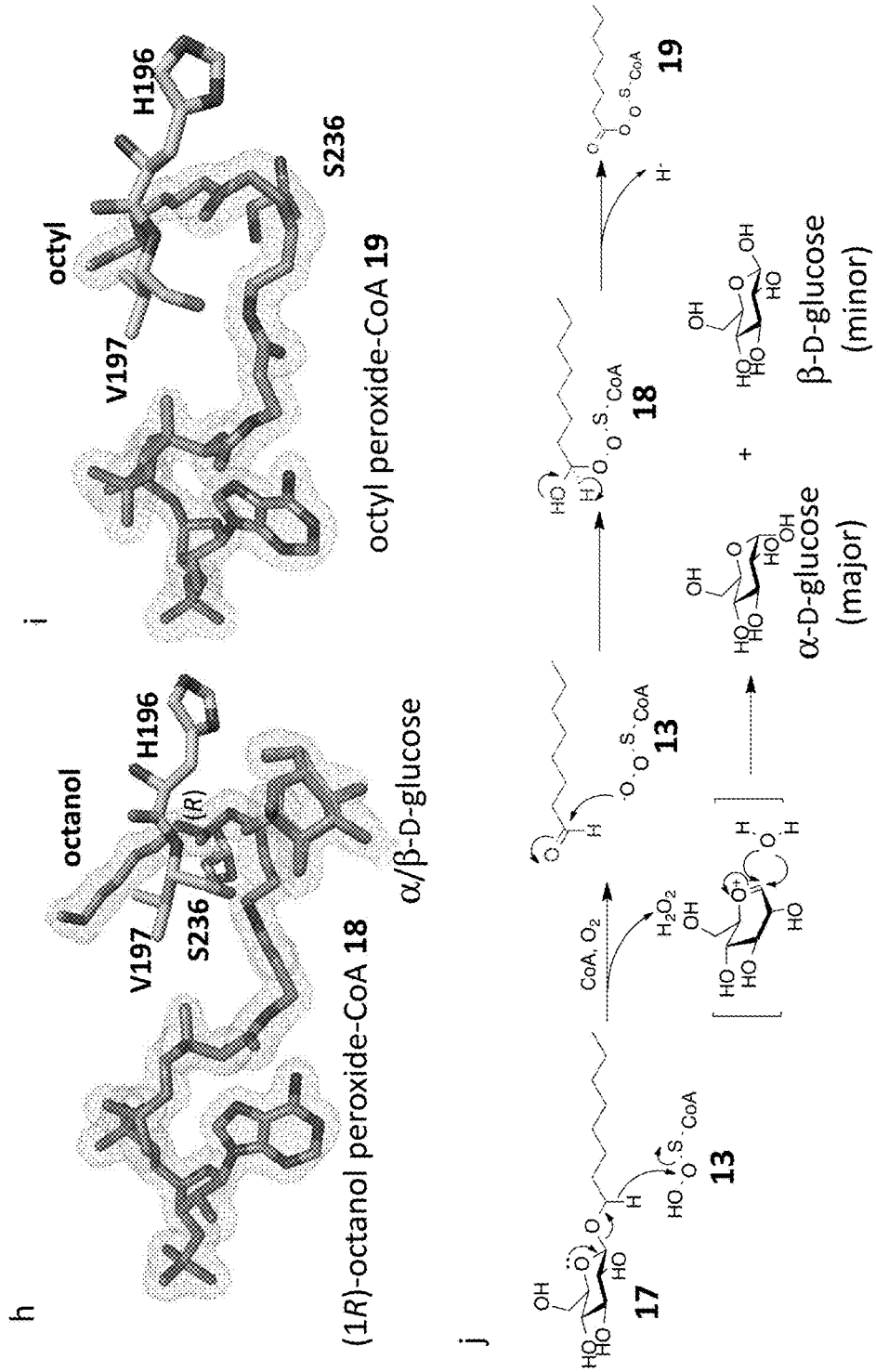
Figure 5:
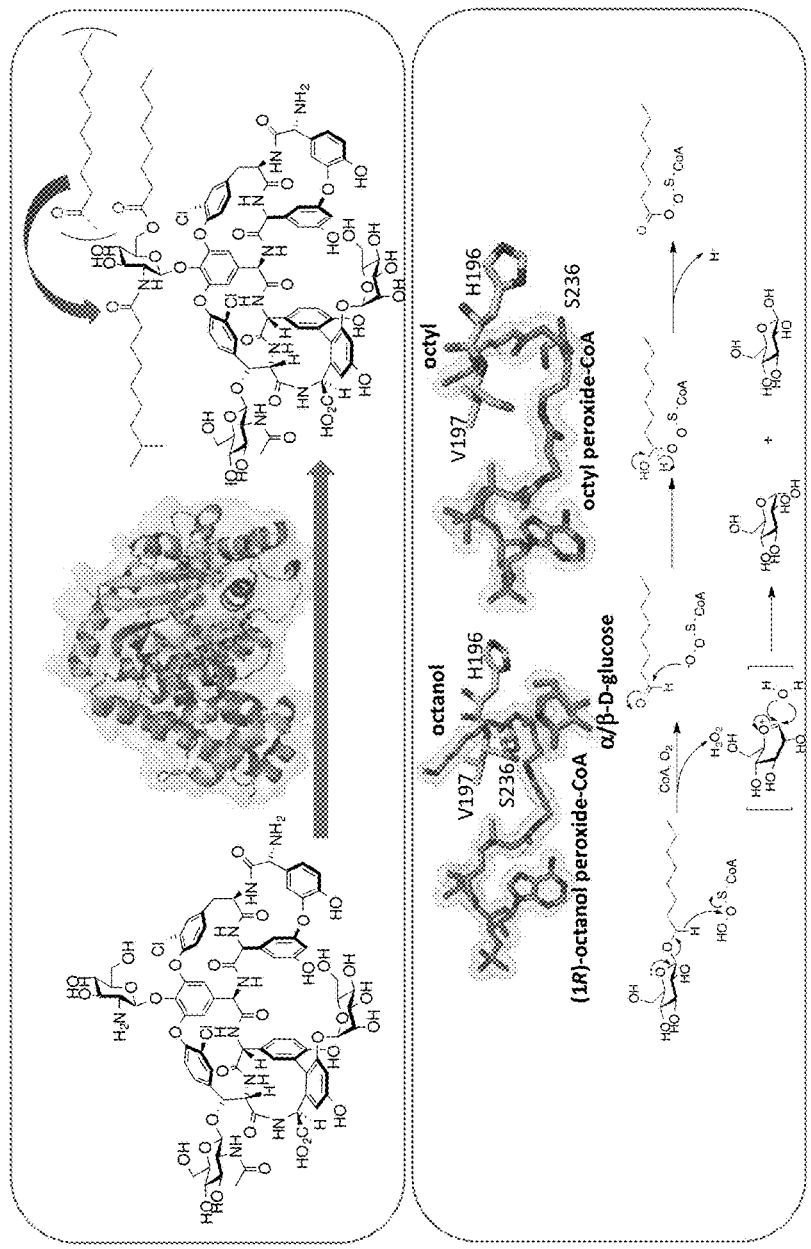

It was further noted that CoA-disulfide 12 is generated considerably in the Orf11*/Dbv8 catalytic reactions (FIGS. 4a,b, traces vii, viii). This oddness prompted revisiting the decanoyl-CoA-containing binary structures from collated data sets to glean clues on this oxidation proclivity. A ternary structure in complex with decanoic acid and CoA was first observed, wherein the thioester scissile bond is broken suggesting that acyl-CoA can undergo a hydrolysis half reaction without presence of Tei pseudoaglycone 3 (FIG. 3c). CoA-disulfide was also found in a second structure (FIG. 5a), suggesting that the enzyme in a way fosters sulfhydryl oxidation of CoA Likely unstable sulfurperoxide-CoA 13, sulfenyl-CoA 14 and decanoylperoxide 15 were further identified in different structures (FIGS. 5b-d), signifying that formation of CoA-disulfide 12 is enzyme-assisted. It was reasoned that the sulfhydryl of CoA 5 is subject to $O_2$ oxidation to form sulfurperoxide-CoA 13, which could undergo lysis to form sulfenyl-CoA 14. Sulfenyl-CoA then reacts with a second molecule of CoA 5 to form the CoA-disulfide 12 (FIG. 5e). However, the formation of decanoylperoxide 15 is still rather perplexing. A decanoyl peroxide-sulfane species 16 was identified in a structure (FIG. 5f). The formation of the product hinted the origin of decanoylperoxide 15. Albeit other routes, such as the radical mechanism, are possible, it was proposed that $O_2$ likely reacts with the soft sulphur atom of acyl-CoA to form a peroxide-sulfonium anion, which attacks the carbonyl carbon of the acyl moiety and then rearranges into the decanoyl peroxide-sulfane species 16 (FIG. 5g).

Provided that the reactive superoxide/sulfenyl-CoA can be formed in the enzyme, further examined was the reaction in the presence of CoA 5 and β-octyl glucoside (β-OG) 17, an N-acyl glucosamine mimic with an alkyl ether linkage to the anomeric carbon of glucose. Since the peroxide/sulfenyl products are too unstable to detect, we also took advantage of x-ray crystallography in a hope to snapshot possible ligand-complexed structures. An (1R)-octanol peroxide-sulfane 18 and an octyl peroxide-sulfane 19 species in the active site of two individual structures were spotted (FIG. 5h,i), assuming a similar conformation as that of decanolyperoxide-CoA (FIG. 5f). This outcome is unexpected as breakage of the β-ether linkage of octanol from β-OG 17 via compound 18 to compound 19 is a net 4-electron oxidation process. D-Glucose was also found adopting both α and β configurations with the former dominant, suggesting that the half-chair oxonium ion is a possible intermediate. Furthermore, the formation of hydrogen peroxide in the enzyme reaction was detected, suggesting that molecular oxygen serves as the electron acceptor in addition to the oxidant. A possible mechanism is likely for this CoA-sulfur-peroxide mediated oxidation, whereby the CoA-sulfur-peroxide plays dual roles as an electrophile as well as a nucleophile in an acid-base disproportionation manner (FIG. 5j).

The development of new chemical entities for antibacterial applications remains a pressing and challenging goal. The elucidation of the ligand-complexed structures of Orf11*/Dbv8 has detailed the intriguing catalytic mechanism at the molecular level.

Example 2

Bioactivity of Teicoplanin Analogs

The preliminary ED50 (potency) of the 2-decanoyl,6-octanoyl teicoplanin analog was determined as follows. 6-8 weeks BALB/c female mice were purchased from the National Laboratory Animal Breeding and Research Center, Taipei, Taiwan. Mice with average body weight of 25 to 30 g were subjected to infection via intraperitoneal (i.p.) injection with $1 \times 10^{10}$ cfu/mouse of E. faecalis (ATCC 51559) at day 0. For the treatment study, mice were randomly assigned into five groups at the start of the experiment and administered different amount of either vancomycin, teicoplanin, 2-$C_{10}$-6-$C_8$-Teicoplanin, or saline (as a blank control) by i.v. twice a day for two days (from day 1 to day 2, a total of 4 doses). The $ED_{50}$ was determine by the concentration of compounds sufficient to rescue 50% infected mice. The results are shown in the table below:

| | ED50 against ATCC 51559 (mg/kg) |
|---|---|
| Vancomycin | >128 |
| Teicoplanin | >128 |
| 2-$C_{10}$-6-$C_8$-Teicoplanin | 2 |

The results obtained from this study indicate that 2-$C_{10}$-6-$C_8$-Teicoplanin is much more effective in inhibiting bacterial infection.

Figure 26:
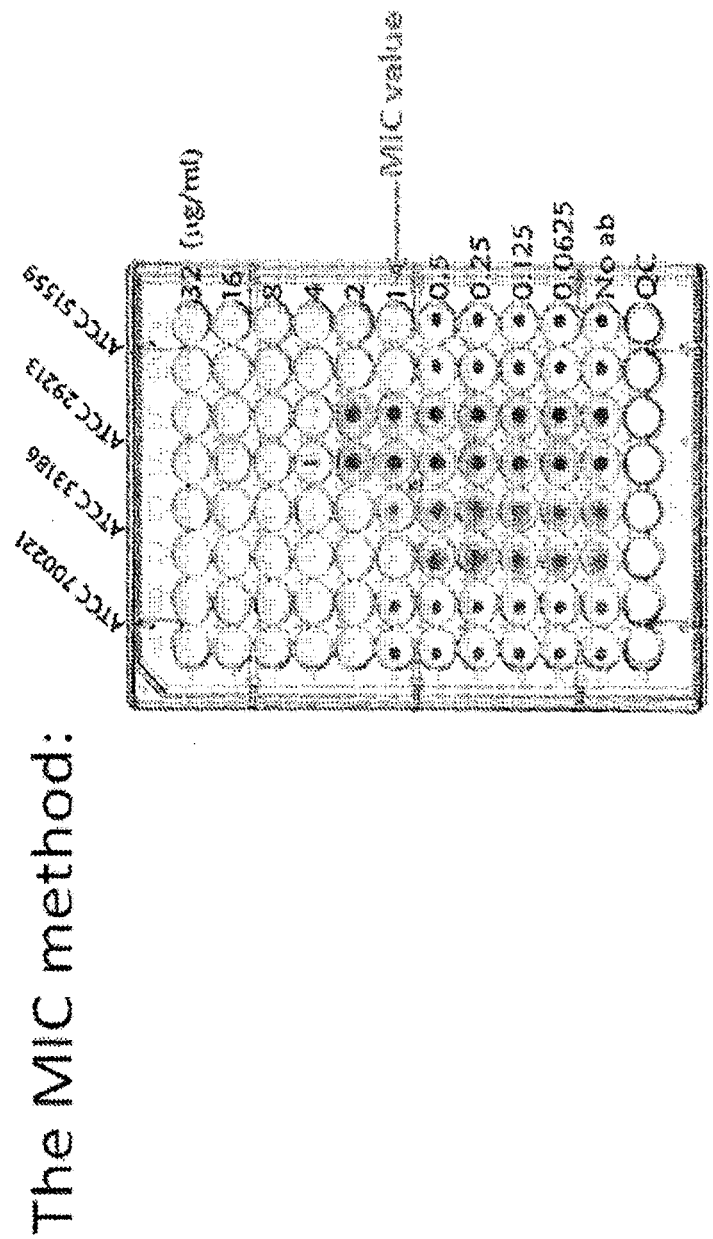
FIG. 26 is a photo showing the MIC values determined by the broth microdilution method, as recommended by the National Committee for Clinical Laboratory Standards (NC-CLS).

The MIC values were determined by the broth microdilution method, as recommended by the National Committee for Clinical Laboratory Standards (NCCLS). Briefly, overnight cultures of tested bacteria were suspended to a turbidity of 0.1 OD units (1~5×$10^8$ CFU/ml). Microtiter plates containing serial dilutions of each antimicrobial agent (0, 1, 2, 4, 8, 16, 32, 64, and 128 μg/ml) were inoculated with each organism to yield the appropriate density (1~5×$10^5$ CFU/ml) in a 200 μL final volume. The plates were incubated for 18~22 h at 37° C. The MIC for all isolates was defined as the lowest concentration of antimicrobial agent that completely inhibited the growth of the organism, as detected with an unaided eye (FIG. 26).

MICs were determined as concentrations at which no growth was observed against the strain tested. Experiments were performed in double duplicate. ATCC 29302/ATCC 33186: a standard strain; ATCC 51299: a low-level vancomycin-resistant (VanB type); ATCC 51559: a multidrug-resistant strain (ampicillin, ciprofloxacin, gentamicin, rifampin, teicoplanin and vancomycin, VanA type VRE); ATCC 700221: a strain resistant to vancomycin, VanA type VRE. ATCC 700802 is a strain resistant to gentamicins and vancomycin. The results are shown in the table below:

| MIC (μg/ml) | Bacteria | | | | | |
|---|---|---|---|---|---|---|
| | ATCC 29302 | ATCC 33186 | ATCC 51299 | ATCC 51559 | ATCC 700221 | ATCC 700802 |
| 2-$C_{10}$-6-$C_8$-Teicoplanin | 1 | 1 | 2 | 1 | 2 | 2 |
| Vancomycin | 1 | 4 | >64 | 1024 | >128 | 64 |
| Teicoplanin | 0.25 | 0.25 | 0.5 | 256 | >128 | 0.5 |

The structure of 2-$C_{10}$-6-$C_8$-Teicoplanin is as follows:

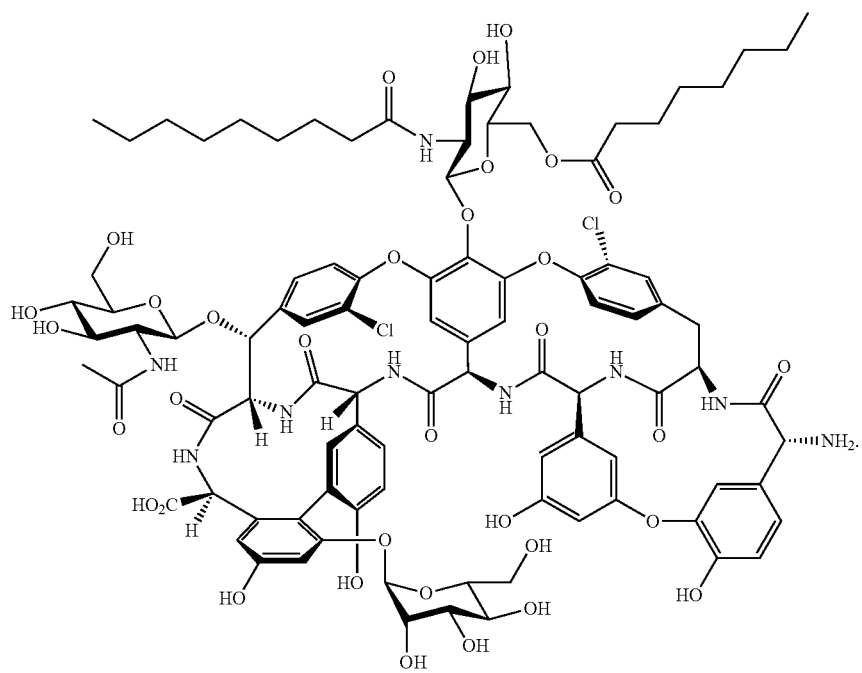

REFERENCES

1 Nicolaou, K. C., Boddy, C. N., Brase, S. & Winssinger, N. Chemistry, Biology, and Medicine of the Glycopeptide Antibiotics. *Angew Chem Int Ed Engl* 38, 2096-2152 (1999).
2 Li, T. L. et al. Biosynthetic gene cluster of the glycopeptide antibiotic teicoplanin: characterization of two glycosyltransferases and the key acyltransferase. *Chem Biol* 11, 107-119, doi:10.1016/j.chembiol.2004.01.001 (2004).
3 Howard-Jones, A. R. et al. Kinetic analysis of teicoplanin glycosyltransferases and acyltransferase reveal ordered tailoring of aglycone scaffold to reconstitute mature teicoplanin. *J Am Chem Soc* 129, 10082-10083, doi: 10.1021/ja0735857 (2007).
4 Kahne, D., Leimkuhler, C., Lu, W. & Walsh, C. Glycopeptide and lipoglycopeptide antibiotics. *Chem Rev* 105, 425-448, doi:10.1021/cr030103a (2005).
5 Kruger, R. G. et al. Tailoring of glycopeptide scaffolds by the acyltransferases from the teicoplanin and A-40,926 biosynthetic operons. *Chem Biol* 12, 131-140, doi: 10.1016/j.chembiol.2004.12.005 (2005).
6 Lin, Y., Fletcher, C. M., Zhou, J., Allis, C. D. & Wagner, G. Solution structure of the catalytic domain of GCN5 histone acetyltransferase bound to coenzyme A. *Nature* 400, 86-89, doi:10.1038/21922 (1999).

7. Rojas, J. R. et al. Structure of Tetrahymena GCN5 bound to coenzyme A and a histone H3 peptide. *Nature* 401, 93-98, doi:10.1038/43487 (1999).
8. Syntichaki, P., Topalidou, I. & Thireos, G. The GcnS bromodomain co-ordinates nucleosome remodelling. *Nature* 404, 414-417, doi: 10.1038/35006136 (2000).
9. Vetting, M. W. et al. Structure and functions of the GNAT superfamily of acetyltransferases. *Arch Biochem Biophys* 433, 212-226, doi:10.1016/j.abb.2004.09.003 (2005).
10. Dyda, F., Klein, D. C. & Hickman, A. B. GCN5-related N-acetyltransferases: a structural overview. *Annu Rev Biophys Biomol Struct* 29, 81-103, doi:10.1146/annurev.biophys.29.1.81 (2000).
11. Marmorstein, R. Structure of histone acetyltransferases. *J Mol Biol* 311, 433-444, doi:10.1006/jmbi.2001.4859 (2001).
12. Marmorstein, R. & Roth, S. Y. Histone acetyltransferases: function, structure, and catalysis. *Curr Opin Genet Dev* 11, 155-161 (2001).
13. Hanson, P. I. & Whiteheart, S. W. AAA+ proteins: have engine, will work. *Nat Rev Mol Cell Biol* 6, 519-529, doi:10.1038/nrm1684 (2005).
14. Das, C., Lucia, M. S., Hansen, K. C. & Tyler, J. K. CBP/p300-mediated acetylation of histone H3 on lysine 56. *Nature* 459, 113-117, doi:10.1038/nature07861 (2009).
15. Verstraeten, N., Fauvart, M., Versees, W. & Michiels, J. The universally conserved prokaryotic GTPases. *Microbiol Mol Biol Rev* 75, 507-542, second and third pages of table of contents, doi:10.1128/MMBR.00009-11 (2011).
16. Chan, H. C. et al. Regioselective deacetylation based on teicoplanin-complexed Orf2* crystal structures. *Mol Biosyst* 7, 1224-1231, doi:10.1039/cOmb00320d (2011).
17. Liu, Y. C. et al. Interception of teicoplanin oxidation intermediates yields new antimicrobial scaffolds. *Nat Chem Biol* 7, 304-309, doi:10.1038/nchembio.556 (2011).
18. Li, T. L., Liu, Y. C. & Lyu, S. Y. Combining biocatalysis and chemoselective chemistries for glycopeptide antibiotics modification. *Curr Opin Chem Biol* 16, 170-178, doi:10.1016/j.cbpa.2012.01.017 (2012).
19. Svetitsky, S., Leibovici, L. & Paul, M. Comparative Efficacy and Safety of Vancomycin versus Teicoplanin: Systematic Review and Meta-Analysis. *Antimicrob Agents Ch* 53, 4069-4079, doi:Doi 10.1128/Aac.00341-09 (2009).
20. Li, Y. S. et al. A unique flavin mononucleotide-linked primary alcohol oxidase for glycopeptide A40926 maturation. *J Am Chem Soc* 129, 13384-13385, doi:10.1021/ja075748x (2007).
21. Huang, Y. T. et al. In vitro characterization of enzymes involved in the synthesis of nonproteinogenic residue (2S,3S)-beta-methylphenylalanine in glycopeptide antibiotic mannopeptimycin. *Chembiochem* 10, 2480-2487, doi:10.1002/cbic.200900351 (2009).
22. Li, T. L., Spiteller, D. & Spencer, J. B. Identification of a pentaketide stilbene produced by a type III polyketide synthase from *Pinus sylvestris* and characterisation of free coenzyme A intermediates. *Chembiochem* 10, 896-901, doi:10.1002/cbic.200800840 (2009).
23. Otwinowski, Z. & Minor, W. Processing of X-ray diffraction data collected in oscillation mode. *Method Enzymol* 276, 307-326, doi:Doi 10.1016/S0076-6879(97)76066-X (1997).
24. Kantardjieff, K. A. & Rupp, B. Matthews coefficient probabilities: Improved estimates for unit cell contents of proteins, DNA, and protein-nucleic acid complex crystals. *Protein Science* 12, 1865-1871, doi:Doi 10.1110/Ps.0350503 (2003).
25. Ness, S. R., de Graaff, R. A. G., Abrahams, J. P. & Pannu, N. S. CRANK: New methods for automated macromolecular crystal structure solution. *Structure* 12, 1753-1761, doi:DOI 10.1016/j.str.2004.07.018 (2004).
26. de Graaff, R. A. G., Hilge, M., van der Plas, J. L. & Abrahams, J. P. Matrix methods for solving protein substructures of chlorine and sulfur from anomalous data. *Acta Crystallogr D* 57, 1857-1862, doi:Doi 10.1107/S0907444901016535 (2001).
27. Pannu, N. S. & Read, R. J. The application of multivariate statistical techniques improves single-wavelength anomalous diffraction phasing. *Acta Crystallogr D* 60, 22-27, doi:Doi 10.1107/S0907444903020808 (2004).
28. Abrahams, J. P. & Leslie, A. G. W. Methods used in the structure determination of bovine mitochondrial F-1 ATPase. *Acta Crystallogr D* 52, 30-42, doi:Doi 10.1107/S0907444995008754 (1996).
29. Cowtan, K. The Buccaneer software for automated model building. 1. Tracing protein chains. *Acta Crystallogr D* 62, 1002-1011, doi:Doi 10.1107/S0907444906022116 (2006).
30. Cowtan, K. Fitting molecular fragments into electron density. *Acta Crystallogr D* 64, 83-89, doi:Doi 10.1107/S0907444907033938 (2008).
31. Emsley, P. & Cowtan, K. Coot: model-building tools for molecular graphics. *Acta crystallographica. Section D, Biological crystallography* 60, 2126-2132, doi:10.1107/S0907444904019158 (2004).
32. Emsley, P., Lohkamp, B., Scott, W. G. & Cowtan, K. Features and development of Coot. *Acta crystallographica. Section D, Biological crystallography* 66, 486-501, doi:10.1107/S0907444910007493 (2010).
33. Murshudov, G. N., Vagin, A. A. & Dodson, E. J. Refinement of macromolecular structures by the maximum-likelihood method. *Acta Crystallogr D* 53, 240-255, doi:Doi 10.1107/S0907444996012255 (1997).
34. Goodsell, D. S. & Olson, A. J. Automated Docking of Substrates to Proteins by Simulated Annealing. *Proteins* 8, 195-202, doi:DOI 10.1002/prot.340080302 (1990).
35. Brooks, B. R. et al. Charmm—a Program for Macromolecular Energy, Minimization, and Dynamics Calculations. *J Comput Chem* 4, 187-217, doi:DOI 10.1002/jcc.540040211 (1983).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous the indole compounds of this invention also can be made, screened for their anti-cancer activities, and used to practice this invention. Thus, other embodiments are also within the claims.

What is claimed is:

1. A compound of Formula (I-a):

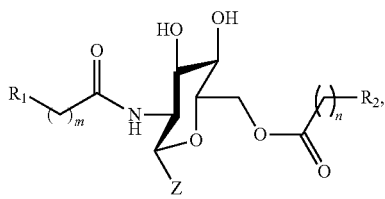

or a pharmaceutically acceptable salt thereof, wherein

Z is of Formula (iii):

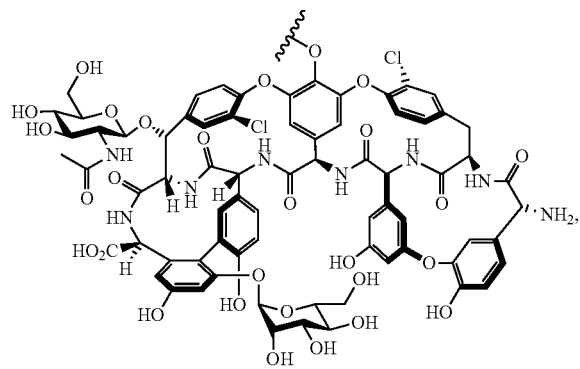

or a derivative thereof;

R₂ is optionally substituted alkyl, optionally substituted alkenyl, optionally substituted carbocyclyl, optionally substituted heterocyclyl, optionally substituted aryl, optionally substituted heteroaryl, C(=O)R$^C$,

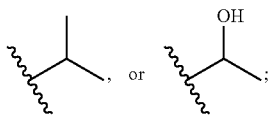

R₁ is optionally substituted alkyl, optionally substituted alkynyl, optionally substituted carbocyclyl, optionally substituted heterocyclyl, optionally substituted aryl, optionally substituted heteroaryl, —C(=O)R$^C$,

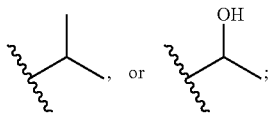

each instance of R$^C$ is independently optionally substituted alkyl, optionally substituted alkenyl, optionally substituted alkynyl, optionally substituted carbocyclyl, optionally substituted heterocyclyl, optionally substituted aryl, optionally substituted heteroaryl, or —OR$^O$;
each instance of R$^O$ is independently hydrogen, optionally substituted alkyl, or an oxygen protecting group;

m is 0 or an integer of 1 to 15, inclusive; and n is 0 or an integer of 1 to 15, inclusive.

2. The compound of claim 1, wherein m is an integer of 1 to 10, inclusive.

3. The compound of claim 1, wherein n is an integer of 1 to 10, inclusive.

4. The compound of claim 1, wherein R₂ is unsubstituted methyl, optionally substituted C$_{1-15}$ alkenyl, optionally substituted aryl, or —C(=O)R$^C$.

5. The compound of claim 1, wherein R₂ is unsubstituted methyl.

6. The compound of claim 1, wherein R₂ is optionally substituted C$_{1-15}$ alkylaryl, substituted C$_{1-15}$ alkylalkynyl, or optionally substituted C$_{1-15}$ alkylhydroxyl.

7. The compound of claim 1, wherein R₂ is of one of the following formulae:

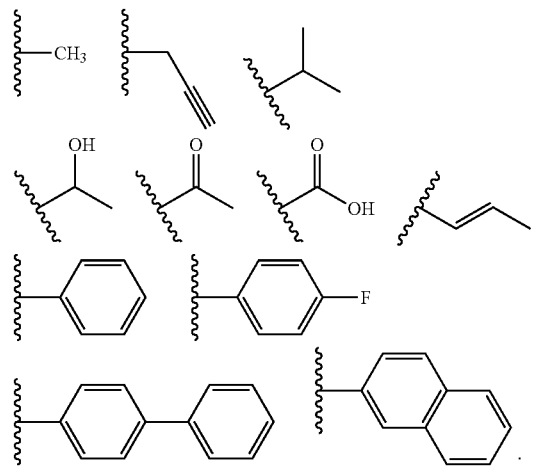

8. The compound of claim 1, wherein

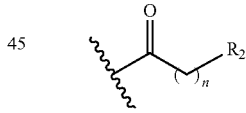

is of one of the following formulae:

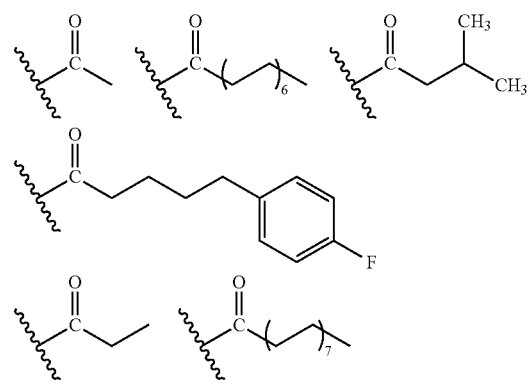

-continued
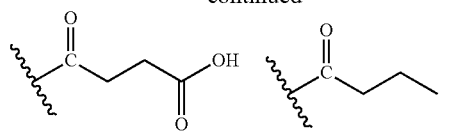
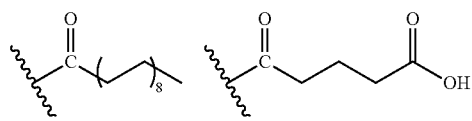
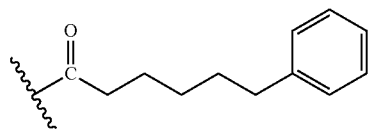
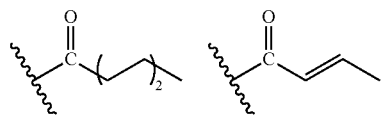
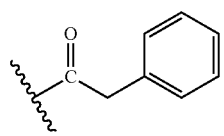
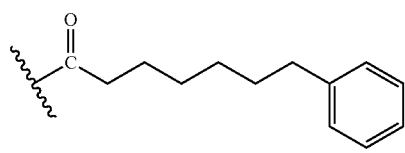
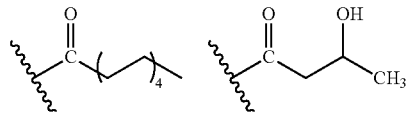
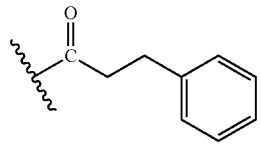
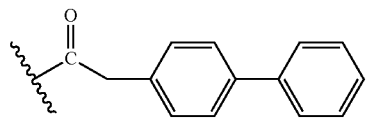
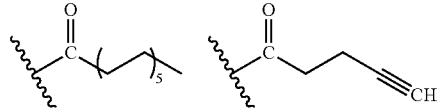
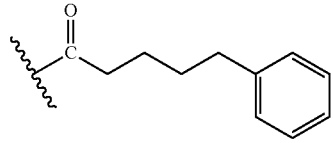
-continued
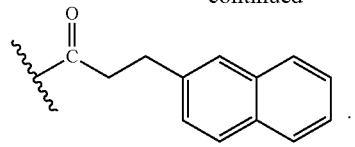
9. The compound of claim 1, wherein
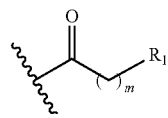
is of one of the following formulae:
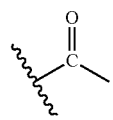 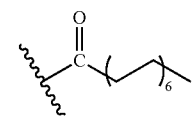 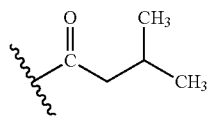
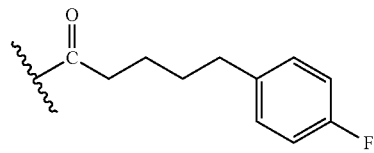
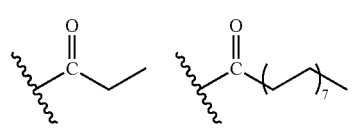
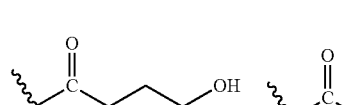
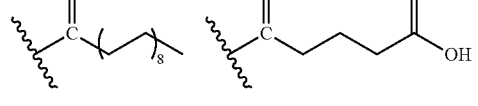
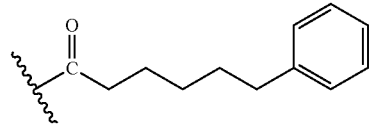
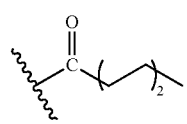
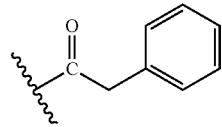

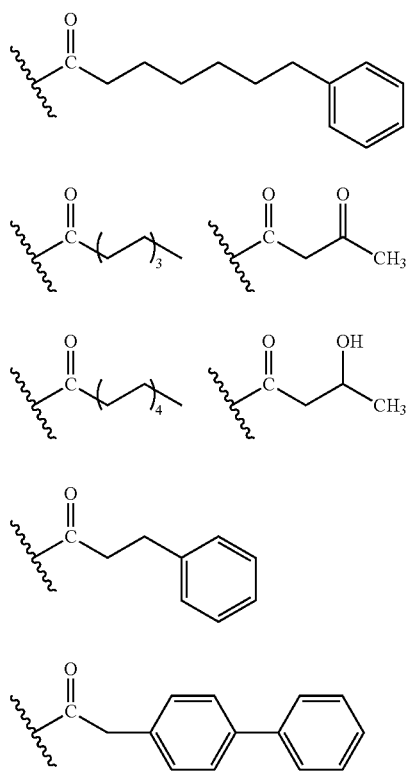
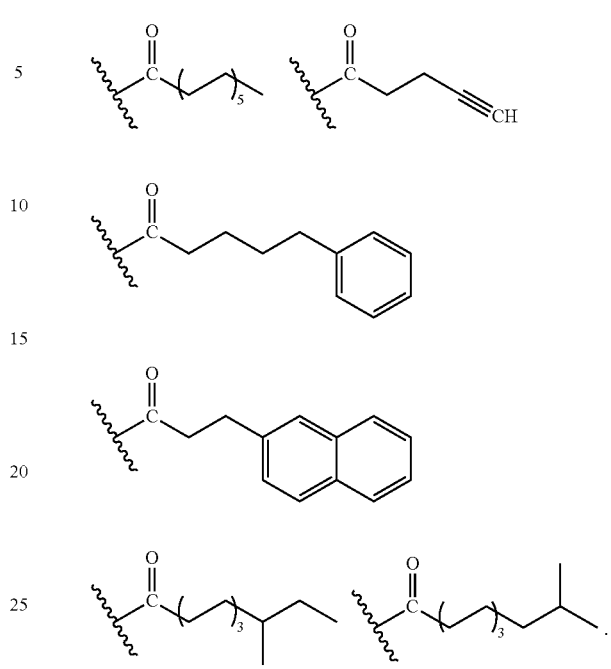
10. The compound of claim 1, which is selected from the group consisting of Compounds 20 and a compound of formula
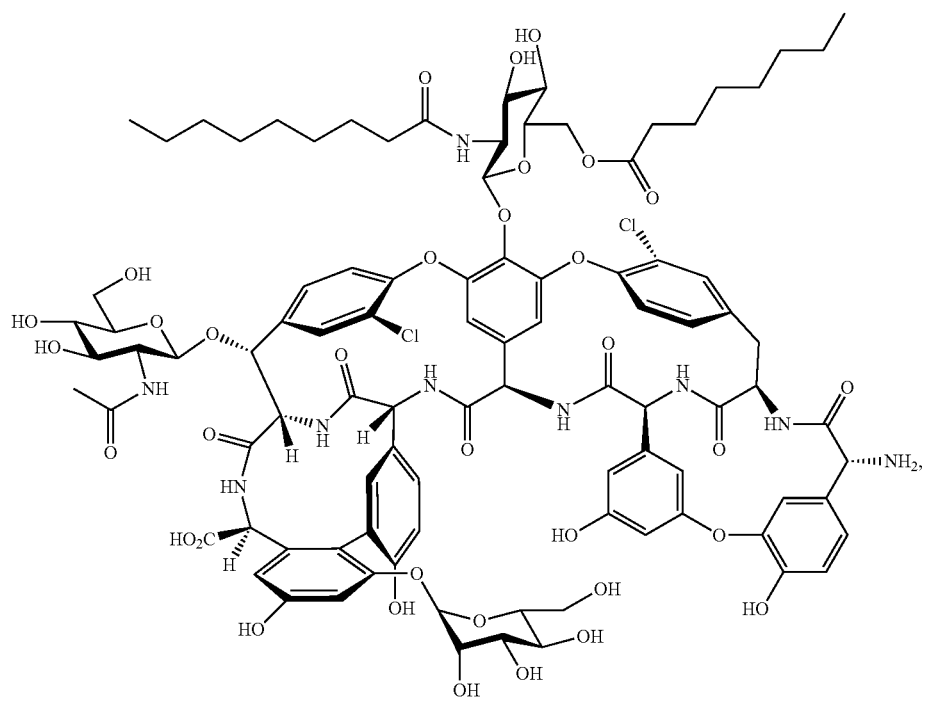
or a pharmaceutically acceptable salt thereof.
11. A pharmaceutical composition comprising a compound of claim 1 and a pharmaceutically acceptable carrier.
12. The compound of claim 1, wherein Z is of Formula (iii):

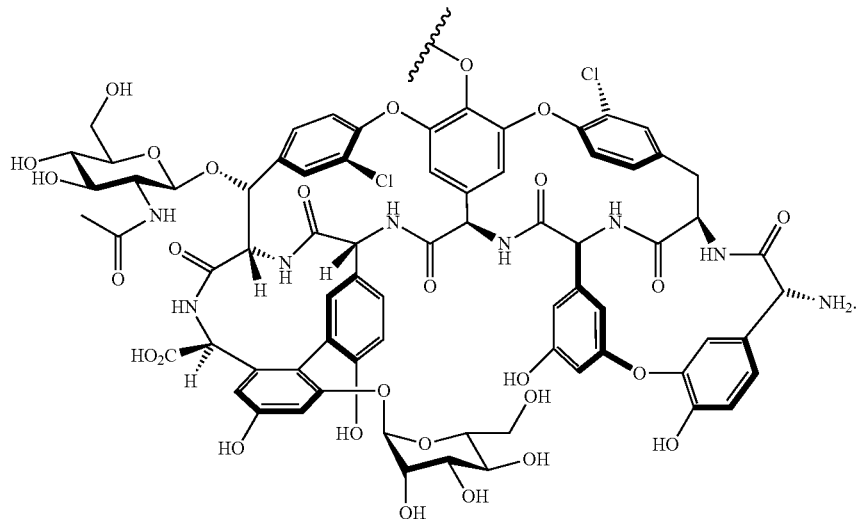

(iii)

13. The compound of claim 1, wherein m is an integer of 1 to 10, inclusive.

14. The compound of claim 1, wherein R² is optionally substituted phenyl.

15. The compound of claim 9, wherein

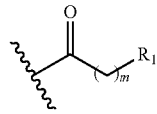

is of the formula

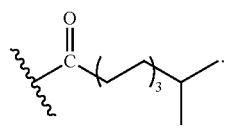

16. A method for inhibiting a bacterium growth comprising contacting the bacterium with an effective amount of the compound of claim 1.

17. A method for treating or preventing a bacterial infection comprising administering an effective amount of the compound of claim 1.

18. The method of claim 16, wherein the bacterium is a Gram-positive bacterium.

19. The method of claim 18, wherein the bacterium is selected from the group consisting of *Staphylococcus* sp., *Enterococcus* sp., *Escherichia coli*, *Bacillus* sp., *Salmonella* sp., and *Mycobacterium* sp.

20. The method of claim 17, wherein the bacterium is of a drug-resistant strain.

21. The method of claim 20, wherein the bacterium is methicillin-resistant *Staphylococcus Aureus* (MRSA), methicillin-resistant *Staphylococcus Epidermidis* (MRSE), penicillin-resistant *Streptococcus pneumonia*, quinolone-resistant *Staphylococcus Aureus* (QRSA), vancomycin-resistant *Staphylococcus Aureus* (VRSA), vancomycin-resistant Enterococci (VRE), or multi-drug resistant *Mycobacterium tuberculosis*.

\* \* \* \* \*